(12) United States Patent
Dixon et al.

(10) Patent No.: US 10,932,908 B2
(45) Date of Patent: Mar. 2, 2021

(54) HEART VALVE SEALING DEVICES AND DELIVERY DEVICES THEREFOR

(71) Applicant: Edwards Lifesciences Corporation, Irvine, CA (US)

(72) Inventors: Eric Robert Dixon, Villa Park, CA (US); Jensen Chen, Walnut, CA (US); Guillermo W. Moratorio, Carlsbad, CA (US); Hengchu Cao, Irvine, CA (US); Douglas Thomas Dominick, Irvine, CA (US); Sergio Delgado, Irvine, CA (US); Lauren R. Freschauf, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 15/914,143

(22) Filed: Mar. 7, 2018

(65) Prior Publication Data

US 2018/0296329 A1 Oct. 18, 2018

Related U.S. Application Data

(60) Provisional application No. 62/486,835, filed on Apr. 18, 2017.

(51) Int. Cl.
*A61F 2/24* (2006.01)
*A61B 17/128* (2006.01)
(Continued)

(52) U.S. Cl.
CPC .......... *A61F 2/246* (2013.01); *A61B 17/1227* (2013.01); *A61B 17/1285* (2013.01); *A61F 2/2403* (2013.01); *A61F 2/2436* (2013.01); *A61F 2/2466* (2013.01); *A61B 2017/00243* (2013.01); *A61B 2017/00349* (2013.01); *A61B 2017/00783* (2013.01);
(Continued)

(58) Field of Classification Search
CPC ........................................................ A61F 2/24
See application file for complete search history.

(56) References Cited

U.S. PATENT DOCUMENTS 3,874,388 A 4/1975 King et al.
4,340,091 A 7/1982 Skelton et al.
(Continued)

FOREIGN PATENT DOCUMENTS

CN 1142351 A 2/1997
EP 0098100 A2 1/1984
(Continued)

OTHER PUBLICATIONS

Al-Khaja et al., "Eleven Years' Experience with Carpentier-Edwards Biological Valves in Relation to Survival and Complications", European Journal of Cardio-thoracic Surgery 3: pp. 305-311, 1989.
(Continued)

*Primary Examiner* — Matthew W Schall
(74) *Attorney, Agent, or Firm* — Thomas C. Richardson

(57) ABSTRACT

An implantable prosthetic has a coaption portion, paddles, and clasps. The paddles are extendable from a folded closed position to an open position. A clasp has a fixed arm attached to the paddle. The clasps also have a moveable arm having a barbed portion and an end that is rounded. A hinge portion connects the fixed arm to the moveable arm.

40 Claims, 76 Drawing Sheets

(51) Int. Cl.
*A61B 17/122* (2006.01)
*A61B 17/00* (2006.01)
*A61B 17/064* (2006.01)
*A61F 2/00* (2006.01)

(52) U.S. Cl.
CPC .......... *A61B 2017/00876* (2013.01); *A61B 2017/0641* (2013.01); *A61F 2/0077* (2013.01); *A61F 2210/0014* (2013.01); *A61F 2220/0008* (2013.01); *A61F 2220/0016* (2013.01); *A61F 2220/0033* (2013.01); *A61F 2220/0041* (2013.01); *A61F 2220/0075* (2013.01); *A61F 2220/0091* (2013.01); *A61F 2230/0006* (2013.01); *A61F 2230/0008* (2013.01); *A61F 2230/0013* (2013.01); *A61F 2230/0045* (2013.01); *A61F 2230/0069* (2013.01)

(56) References Cited

U.S. PATENT DOCUMENTS

| | | |
|---|---|---|
| 4,506,669 A | 3/1985 | Blake, III |
| 4,590,937 A | 5/1986 | Deniega |
| 4,693,248 A | 9/1987 | Failla |
| 4,803,983 A | 2/1989 | Siegel |
| 5,125,895 A | 6/1992 | Buchbinder et al. |
| 5,171,252 A | 12/1992 | Friedland |
| 5,195,962 A | 3/1993 | Martin et al. |
| 5,292,326 A | 3/1994 | Green et al. |
| 5,327,905 A | 7/1994 | Avitall |
| 5,363,861 A | 11/1994 | Edwards et al. |
| 5,370,685 A | 12/1994 | Stevens |
| 5,389,077 A | 2/1995 | Melinyshyn et al. |
| 5,411,552 A | 5/1995 | Andersen |
| 5,450,860 A | 9/1995 | O'Connor |
| 5,456,400 A | 10/1995 | Shichman et al. |
| 5,456,674 A | 10/1995 | Bos et al. |
| 5,474,057 A | 12/1995 | Makower et al. |
| 5,478,353 A | 12/1995 | Yoon |
| 5,487,746 A | 1/1996 | Yu et al. |
| 5,565,004 A | 10/1996 | Christoudias |
| 5,607,462 A | 3/1997 | Imran |
| 5,609,598 A | 3/1997 | Laufer et al. |
| 5,611,794 A | 3/1997 | Sauer et al. |
| 5,626,607 A | 5/1997 | Malecki et al. |
| 5,695,504 A | 12/1997 | Gifford, III et al. |
| 5,716,417 A | 2/1998 | Girard et al. |
| 5,727,569 A | 3/1998 | Benetti et al. |
| 5,741,297 A | 4/1998 | Simon |
| 5,782,746 A | 7/1998 | Wright |
| 5,797,960 A | 8/1998 | Stevens et al. |
| 5,836,311 A | 11/1998 | Borst et al. |
| 5,843,076 A | 12/1998 | Webster, Jr. et al. |
| 5,855,590 A | 1/1999 | Malecki et al. |
| 5,885,271 A | 3/1999 | Hamilton et al. |
| 5,888,247 A | 3/1999 | Benetti |
| 5,891,017 A | 4/1999 | Swindle et al. |
| 5,891,112 A | 4/1999 | Samson |
| 5,894,843 A | 4/1999 | Benetti et al. |
| 5,921,979 A | 7/1999 | Kovac et al. |
| 5,944,738 A | 8/1999 | Amplatz et al. |
| 5,957,835 A | 9/1999 | Anderson et al. |
| 5,972,020 A | 10/1999 | Carpentier et al. |
| 5,980,534 A | 11/1999 | Gimpelson |
| 6,004,329 A | 12/1999 | Myers et al. |
| 6,010,531 A | 1/2000 | Donlon et al. |
| 6,017,358 A | 1/2000 | Yoon et al. |
| 6,086,600 A | 7/2000 | Kortenbach |
| 6,120,496 A | 9/2000 | Whayne et al. |
| 6,132,370 A | 10/2000 | Furnish et al. |
| 6,162,239 A | 12/2000 | Manhes |
| 6,165,183 A | 12/2000 | Kuehn et al. |
| 6,182,664 B1 | 2/2001 | Cosgrove |
| 6,193,732 B1 | 2/2001 | Frantzen et al. |
| 6,193,734 B1 | 2/2001 | Bolduc et al. |
| 6,200,315 B1 | 3/2001 | Gaiser et al. |
| 6,241,743 B1 | 6/2001 | Levin et al. |
| 6,269,819 B1 | 8/2001 | Oz et al. |
| 6,269,829 B1 | 8/2001 | Chen et al. |
| 6,312,447 B1 | 11/2001 | Grimes |
| 6,458,153 B1 | 10/2002 | Bailey et al. |
| 6,461,366 B1 | 10/2002 | Seguin |
| 6,468,285 B1 | 10/2002 | Hsu et al. |
| 6,508,806 B1 | 1/2003 | Hoste |
| 6,508,825 B1 | 1/2003 | Selmon et al. |
| 6,530,933 B1 | 3/2003 | Yeung et al. |
| 6,537,290 B2 | 3/2003 | Adams et al. |
| 6,544,215 B1 | 4/2003 | Bencini et al. |
| 6,575,971 B2 | 6/2003 | Hauck et al. |
| 6,626,930 B1 | 9/2003 | Allen et al. |
| 6,629,534 B1 | 10/2003 | St. Goar et al. |
| 6,695,866 B1 | 2/2004 | Kuehn et al. |
| 6,719,767 B1 | 4/2004 | Kimblad |
| 6,752,813 B2 | 6/2004 | Goldfarb et al. |
| 6,764,510 B2 | 7/2004 | Vidlund et al. |
| 6,770,083 B2 | 8/2004 | Seguin |
| 6,837,867 B2 | 1/2005 | Kortelling |
| 6,855,137 B2 | 2/2005 | Bon |
| 6,875,224 B2 | 4/2005 | Grimes |
| 6,913,614 B2 | 7/2005 | Marino et al. |
| 6,939,337 B2 | 9/2005 | Parker et al. |
| 6,945,956 B2 | 9/2005 | Waldhauser et al. |
| 7,011,669 B2 | 3/2006 | Kimblad |
| 7,048,754 B2 | 5/2006 | Martin et al. |
| 7,101,395 B2 | 9/2006 | Tremulis et al. |
| 7,112,207 B2 | 9/2006 | Allen et al. |
| 7,125,421 B2 | 10/2006 | Tremulis et al. |
| 7,226,467 B2 | 6/2007 | Lucatero et al. |
| 7,288,097 B2 | 10/2007 | Seguin |
| 7,371,210 B2 | 5/2008 | Brock et al. |
| 7,464,712 B2 | 12/2008 | Oz et al. |
| 7,509,959 B2 | 3/2009 | Oz et al. |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,704,269 B2 | 4/2010 | St. Goar et al. |
| 7,731,706 B2 | 6/2010 | Potter |
| 7,736,388 B2 | 6/2010 | Goldfarb et al. |
| 7,744,609 B2 | 6/2010 | Allen et al. |
| 7,748,389 B2 | 7/2010 | Salahieh et al. |
| 7,753,923 B2 | 7/2010 | St. Goar et al. |
| 7,753,932 B2 | 7/2010 | Gingrich et al. |
| 7,758,596 B2 | 7/2010 | Oz et al. |
| 7,780,723 B2 | 8/2010 | Taylor |
| 7,803,185 B2 | 9/2010 | Gabbay |
| 7,811,296 B2 | 10/2010 | Goldfarb et al. |
| 7,824,443 B2 | 11/2010 | Salahieh et al. |
| 7,981,123 B2 | 7/2011 | Seguin |
| 7,988,724 B2 | 8/2011 | Salahieh et al. |
| 7,998,151 B2 | 8/2011 | St. Goar et al. |
| 8,029,518 B2 | 10/2011 | Goldfarb et al. |
| 8,052,592 B2 | 11/2011 | Goldfarb et al. |
| 8,052,749 B2 | 11/2011 | Salahieh et al. |
| 8,052,750 B2 | 11/2011 | Tuval et al. |
| 8,057,493 B2 | 11/2011 | Goldfarb et al. |
| 8,070,805 B2 | 12/2011 | Vidlund et al. |
| 8,096,985 B2 | 1/2012 | Legaspi et al. |
| 8,104,149 B1 | 1/2012 | McGarity |
| 8,123,703 B2 | 2/2012 | Martin et al. |
| 8,133,239 B2 | 3/2012 | Oz et al. |
| 8,147,542 B2 | 4/2012 | Maisano et al. |
| 8,172,856 B2 | 5/2012 | Eigler et al. |
| 8,187,299 B2 | 5/2012 | Goldfarb et al. |
| 8,206,437 B2 | 6/2012 | Bonhoeffer et al. |
| 8,216,256 B2 | 7/2012 | Raschdorf, Jr. et al. |
| 8,216,301 B2 | 7/2012 | Bonhoeffer et al. |
| 8,303,608 B2 | 11/2012 | Goldfarb et al. |

(56) References Cited

U.S. PATENT DOCUMENTS

| | | |
|---|---|---|
| 8,303,653 B2 | 11/2012 | Bonhoeffer et al. |
| 8,313,525 B2 | 11/2012 | Tuval et al. |
| 8,323,334 B2 | 12/2012 | Deem et al. |
| 8,343,174 B2 | 1/2013 | Goldfarb et al. |
| 8,348,995 B2 | 1/2013 | Tuval et al. |
| 8,348,996 B2 | 1/2013 | Tuval et al. |
| 8,409,273 B2 | 4/2013 | Thornton et al. |
| 8,414,643 B2 | 4/2013 | Tuval et al. |
| 8,425,404 B2 | 4/2013 | Wilson et al. |
| 8,449,599 B2 | 5/2013 | Chau et al. |
| 8,449,606 B2 | 5/2013 | Eliasen et al. |
| 8,460,368 B2 | 6/2013 | Taylor et al. |
| 8,470,028 B2 | 6/2013 | Thornton et al. |
| 8,480,730 B2 | 7/2013 | Maurer et al. |
| 8,500,761 B2 | 8/2013 | Goldfarb et al. |
| 8,540,767 B2 | 9/2013 | Zhang |
| 8,579,965 B2 | 11/2013 | Bonhoeffer et al. |
| 8,585,756 B2 | 11/2013 | Bonhoeffer et al. |
| 8,652,202 B2 | 2/2014 | Alon et al. |
| 8,668,733 B2 | 3/2014 | Haug et al. |
| 8,721,665 B2 | 5/2014 | Oz et al. |
| 8,734,505 B2 | 5/2014 | Goldfarb et al. |
| 8,740,918 B2 | 6/2014 | Seguin |
| 8,740,920 B2 | 6/2014 | Goldfarb et al. |
| 8,747,460 B2 | 6/2014 | Tuval et al. |
| 8,771,345 B2 | 7/2014 | Tuval et al. |
| 8,771,346 B2 | 7/2014 | Tuval et al. |
| 8,771,347 B2 | 7/2014 | DeBoer et al. |
| 8,778,017 B2 | 7/2014 | Eliasen et al. |
| 8,834,564 B2 | 9/2014 | Tuval et al. |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,926,691 B2 | 1/2015 | Chau et al. |
| 8,945,177 B2 | 2/2015 | Dell et al. |
| 8,992,608 B2 | 3/2015 | Haug et al. |
| 9,011,468 B2 | 4/2015 | Ketai et al. |
| 9,034,032 B2 | 5/2015 | McLean et al. |
| 9,044,246 B2 | 6/2015 | Goldfarb et al. |
| 9,060,858 B2 | 6/2015 | Thornton et al. |
| 9,138,312 B2 | 9/2015 | Tuval et al. |
| 9,155,619 B2 | 10/2015 | Liu et al. |
| 9,198,757 B2 | 12/2015 | Schroeder et al. |
| 9,220,507 B1 | 12/2015 | Patel et al. |
| 9,259,317 B2 | 2/2016 | Wilson et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,387,071 B2 | 7/2016 | Tuval et al. |
| 9,414,918 B2 | 8/2016 | Chau et al. |
| 9,427,237 B2 | 8/2016 | Oz et al. |
| 9,427,327 B2 | 8/2016 | Parrish |
| 9,439,763 B2 | 9/2016 | Geist et al. |
| 9,510,829 B2 | 12/2016 | Goldfarb et al. |
| 9,510,837 B2 | 12/2016 | Seguin |
| 9,510,946 B2 | 12/2016 | Chau et al. |
| 9,539,092 B2 | 1/2017 | Bourang et al. |
| 9,572,660 B2 | 2/2017 | Braido et al. |
| 9,642,704 B2 | 5/2017 | Tuval et al. |
| 9,700,445 B2 | 7/2017 | Martin et al. |
| 9,775,963 B2 | 10/2017 | Miller |
| D809,139 S | 1/2018 | Marsot et al. |
| 9,889,002 B2 | 2/2018 | Bonhoeffer et al. |
| 9,949,824 B2 | 4/2018 | Bonhoeffer et al. |
| 10,076,327 B2 | 9/2018 | Ellis et al. |
| 10,076,415 B1 | 9/2018 | Metchik et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0173811 A1 | 11/2002 | Tu et al. |
| 2002/0183787 A1 | 12/2002 | Wahr et al. |
| 2003/0050693 A1 | 3/2003 | Quijano et al. |
| 2003/0069593 A1 | 4/2003 | Tremulis et al. |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goer et al. |
| 2004/0034365 A1 | 2/2004 | Lentz et al. |
| 2004/0039442 A1 | 2/2004 | St. Goar et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0097979 A1 | 5/2004 | Svanidze et al. |
| 2004/0127981 A1 | 7/2004 | Randert et al. |
| 2004/0127982 A1 | 7/2004 | Machold et al. |
| 2004/0147943 A1 | 7/2004 | Kobayashi |
| 2004/0167539 A1 | 8/2004 | Kuehn et al. |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2005/0010287 A1 | 1/2005 | Macoviak et al. |
| 2005/0033446 A1 | 2/2005 | Deem et al. |
| 2005/0049618 A1 | 3/2005 | Masuda et al. |
| 2005/0137686 A1 | 6/2005 | Salahieh et al. |
| 2005/0137690 A1 | 6/2005 | Salahieh et al. |
| 2005/0143767 A1 | 6/2005 | Kimura et al. |
| 2005/0165429 A1 | 7/2005 | Douglas et al. |
| 2005/0216039 A1 | 9/2005 | Lederman |
| 2005/0240219 A1 | 10/2005 | Kahle et al. |
| 2005/0251183 A1 | 11/2005 | Buckman et al. |
| 2005/0267493 A1 | 12/2005 | Schreck et al. |
| 2005/0277959 A1 | 12/2005 | Cosgrove et al. |
| 2005/0288786 A1 | 12/2005 | Chanduszko |
| 2006/0020275 A1 | 1/2006 | Goldfarb et al. |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0178700 A1 | 8/2006 | Quinn |
| 2006/0224169 A1 | 10/2006 | Weisenburgh et al. |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0038293 A1 | 2/2007 | St.Goar et al. |
| 2007/0093857 A1 | 4/2007 | Rogers et al. |
| 2007/0093890 A1 | 4/2007 | Eliasen et al. |
| 2007/0100356 A1 | 5/2007 | Lucatero et al. |
| 2007/0129737 A1 | 6/2007 | Goldfarb et al. |
| 2007/0156197 A1 | 7/2007 | Root et al. |
| 2007/0191154 A1 | 8/2007 | Genereux |
| 2007/0197858 A1 | 8/2007 | Goldfarb et al. |
| 2007/0198038 A1 | 8/2007 | Cohen et al. |
| 2007/0265700 A1 | 11/2007 | Eliasen et al. |
| 2007/0282414 A1 | 12/2007 | Soltis et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0167713 A1 | 7/2008 | Bolling |
| 2008/0167714 A1 | 7/2008 | St. Goar et al. |

(56) References Cited

U.S. PATENT DOCUMENTS

| | | |
|---|---|---|
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281411 A1 | 11/2008 | Berreklouw |
| 2008/0287862 A1 | 11/2008 | Weitzner et al. |
| 2008/0294247 A1 | 11/2008 | Yang et al. |
| 2006/0319455 | 12/2008 | Harris et al. |
| 2008/0312506 A1 | 12/2008 | Spivey et al. |
| 2008/0312664 A1 | 12/2008 | Bardsley et al. |
| 2009/0005863 A1 | 1/2009 | Goetz et al. |
| 2009/0024110 A1 | 1/2009 | Heideman et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0275902 A1 | 11/2009 | Heeps et al. |
| 2009/0287304 A1 | 11/2009 | Dahlgren |
| 2010/0022823 A1 | 1/2010 | Goldfarb et al. |
| 2010/0057192 A1 | 3/2010 | Celermaier |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0217283 A1 | 8/2010 | St. Goar et al. |
| 2010/0249497 A1 | 9/2010 | Peine et al. |
| 2010/0324595 A1 | 12/2010 | Linder et al. |
| 2011/0004227 A1 | 1/2011 | Goldfarb et al. |
| 2011/0082538 A1 | 4/2011 | Dahlgren et al. |
| 2011/0137410 A1 | 6/2011 | Hacohen |
| 2011/0245855 A1 | 10/2011 | Matsuoka et al. |
| 2011/0257723 A1 | 10/2011 | McNamara |
| 2011/0257734 A1 | 10/2011 | Chalekian |
| 2011/0295281 A1 | 12/2011 | Mizurnoto et al. |
| 2012/0022633 A1 | 1/2012 | Olson et al. |
| 2012/0041453 A1 | 2/2012 | Klingenbeck |
| 2012/0046741 A1 | 2/2012 | Tuval et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0123327 A1 | 5/2012 | Miller |
| 2012/0209318 A1 | 8/2012 | Qadeer |
| 2012/0277853 A1 | 11/2012 | Rothstein |
| 2013/0018372 A1 | 1/2013 | Sims et al. |
| 2013/0035759 A1 | 2/2013 | Gross et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0190798 A1 | 7/2013 | Kapadia |
| 2013/0190861 A1 | 7/2013 | Chau et al. |
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0325110 A1 | 12/2013 | Khalil et al. |
| 2014/0031928 A1 | 1/2014 | Murphy et al. |
| 2014/0039608 A1 | 2/2014 | Eidenschink |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0066693 A1 | 3/2014 | Goldfarb et al. |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0277404 A1 | 9/2014 | Wilson et al. |
| 2014/0277411 A1 | 9/2014 | Bortlein et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0094804 A1 | 4/2015 | Bonhoeffer et al. |
| 2015/0100116 A1 | 4/2015 | Mohl et al. |
| 2015/0105804 A1 | 4/2015 | Dell et al. |
| 2015/0105808 A1 | 4/2015 | Gordon et al. |
| 2015/0105857 A1 | 4/2015 | Bonhoeffer et al. |
| 2015/0148896 A1 | 5/2015 | Karapetian et al. |
| 2015/0157268 A1 | 6/2015 | Winshtein et al. |
| 2015/0230919 A1 | 6/2015 | Chau et al. |
| 2015/0182223 A1 | 7/2015 | Ketai et al. |
| 2015/0196390 A1 | 7/2015 | Ma et al. |
| 2015/0223793 A1 | 8/2015 | Goldfarb et al. |
| 2015/0238313 A1 | 8/2015 | Spence et al. |
| 2015/0257677 A1 | 9/2015 | Hernandez |
| 2015/0257756 A1 | 9/2015 | Sauer |
| 2015/0257757 A1 | 9/2015 | Powers et al. |
| 2015/0257883 A1 | 9/2015 | Basucie et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008129 A1 | 1/2016 | Siegel |
| 2016/0008131 A1 | 1/2016 | Christianson et al. |
| 2016/0022970 A1 | 1/2016 | Forcucci et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0287387 A1 | 10/2016 | Wei |
| 2016/0317290 A1 | 11/2016 | Chau et al. |
| 2016/0324634 A1 | 11/2016 | Gabbay |
| 2016/0331523 A1 | 11/2016 | Chau et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100236 A1 | 4/2017 | Robertson et al. |
| 2017/0143330 A1 | 5/2017 | Basude et al. |
| 2017/0156725 A1 | 6/2017 | Hemmann |
| 2017/0231755 A1 | 8/2017 | Gloss et al. |
| 2017/0239048 A1 | 8/2017 | Goldfarb et al. |
| 2017/0252154 A1 | 9/2017 | Tubishevitz et al. |
| 2017/0281330 A1 | 10/2017 | Liljegren et al. |
| 2017/0348102 A1 | 12/2017 | Cousins et al. |
| 2018/0000582 A1 | 1/2018 | Tuval et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0078271 A1 | 3/2018 | Thrasher, III |
| 2018/0126124 A1 | 5/2018 | Winston et al. |
| 2018/0133008 A1 | 5/2018 | Kizuka et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |

(56) References Cited

U.S. PATENT DOCUMENTS

| | | | |
|---|---|---|---|
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029610 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2020/0113683 A1 | 4/2020 | Dale et al. |

FOREIGN PATENT DOCUMENTS

| | | |
|---|---|---|
| EP | 0879069 B1 | 8/2003 |
| EP | 1281375 A3 | 12/2003 |
| EP | 1301235 B1 | 10/2004 |
| EP | 1583577 B1 | 5/2007 |
| EP | 1408850 B1 | 9/2009 |
| EP | 0930845 B1 | 10/2009 |
| EP | 1624810 B1 | 3/2011 |
| EP | 1804686 B1 | 9/2015 |
| EP | 2428169 B1 | 10/2016 |
| EP | 2266503 B1 | 1/2017 |
| EP | 2266504 B1 | 3/2017 |
| FR | 2146050 A5 | 2/1973 |
| FR | 9711600 | 3/1997 |
| FR | 2 768 324 A1 | 3/1999 |
| JP | 2014000417 A | 1/2014 |
| WO | 9802103 A1 | 1/1998 |
| WO | 9900059 A1 | 1/1999 |
| WO | 9913777 A1 | 3/1999 |
| WO | 0060995 A3 | 4/2001 |
| WO | 03001893 A2 | 1/2003 |
| WO | 2004103162 A2 | 12/2004 |
| WO | 2004103434 A2 | 12/2004 |
| WO | 2005112792 A2 | 12/2005 |
| WO | 2006086434 A1 | 8/2006 |
| WO | 2006116558 A2 | 11/2006 |
| WO | 2006138173 A3 | 3/2007 |
| WO | 2006047709 A3 | 7/2007 |
| WO | 2008147964 A1 | 12/2008 |
| WO | 2008150529 A1 | 12/2008 |
| WO | 2009024859 A3 | 5/2009 |
| WO | 2009108942 A1 | 9/2009 |
| WO | 2009053952 A3 | 12/2009 |
| WO | 2009116041 A3 | 3/2010 |
| WO | 2010098804 A1 | 9/2010 |
| WO | 2010128502 A1 | 11/2010 |
| WO | 2011034628 A1 | 3/2011 |
| WO | 2013059747 A1 | 4/2013 |
| WO | 2016110760 A1 | 7/2016 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |

OTHER PUBLICATIONS

Almagor et al., "Balloon Expandable Stent Implantation in Stenotic Right Heart Valved Conduits", Journal of the American College of Cardiology, vol. 16, No. 6, pp. 1310-1314, Nov. 15, 1990.

Al Zaibag et al., "Percutaneous Balloon Valvotomy in Tricuspid Stenosis", British Heart Journal, vol. 57, No. 1, Jan. 1987.

Andersen, H.R. "History of Percutaneous Aortic Valve Prosthesis," Herz No. 34. pp. 343-346. 2009.

Benchimol et al., "Simultaneous Left Ventricular Echocardiography and Aortic Blood Velocity During Rapid Right Ventricular Pacing in Man", The American Journal of the Medical Sciences, vol. 273, No. 1, pp. 55-62, 1977.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, pp. 654-670, 1964.

Kolata, Gina "Device that Opens Clogged Arteries Gets a Failing Grade in a New Study", The New York Times, http://www.nytimes.com/1991/01/03/health/device-that-opens-clogged-arteries-gets-a-faili . . . , pp. 1-2, wrriten Jan. 3, 199, web page access Jul. 29, 2009.

Inoune, M.D., Kanji, et al., "Clinical Application of Transvenous Mitral Commissurotomy by a New Balloon catheter," The Journal of Thoracic and Cardiovascular Surgery 87:394-402, 1984.

Lawrence, Jr., et al., "Percutaneous Endovascular Graft: Experimental Evaluation", Cardiovascular Radiology 163, pp. 357-360, May 1987.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann et al., "Der Verschluβ des Ductus Arteriosus Persistens Ohne Thorakotomie", Thoraxchirurgie Vaskuläre Chirurgie, Band 15, Heft 2, Stuttgart, im Apr. 1967, pp. 199-203.

Rashkind et al., "Creation of an Atrial Septal Defect Without Thoracotomy: A Pallative Approach to Complete Transposition of the Great Arteries", The Journal of the American Medical Association, vol. 196, No. 11, pp. 173-174, Jun. 13, 1956.

Rashkind et al., "Historical Aspects of Interventional Cardiology: Past, Present, and Future", Texas Heart Institute Journal, Interventional Cardiology, pp. 363-367.

Rosch, M.D., Josef, "The Birth, Early Years and Future of Interventional Radiology," J Vasc Interv Radiol 2003; 14:841-853.

Ross, D.N, "Aortic Valve Surgery", Surgery of the Aortic Valves, Guy's Hospital, London, pp. 192-197.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Selby et al., "Experience with New Retrieval Forceps for Foreign Body Removal in the Vascular, Urinary, and Biliary Systems", Radiology: 176. pp. 535-538, 1990.

(56) References Cited

OTHER PUBLICATIONS

Serruys et al., "Stenting of Coronary Arteries. Are we the Sorcerer's Apprentice?", European Heart Journal, 10, 774-782, pp. 37-45, 1989.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Uchida et al., "Modifications of Gianturco Expandable Wire Stents", Technical Note, American Roentgen Ray Society, pp. 1185-1187, May 1988.

Urban, Philip MD, "Coronary Artery Stenting", Editions Medecine et Hygiene, Geneve, pp. 1-47, 1991.

Watt et al., "Intravenous Adenosine in the Treatment of Supraventricular Tachycardia: A Dose-Ranging Study and Interaction with Dipyridamole", Br. J. Clin. Pharmac. 21, pp. 227-230, 1986.

Wheatley, David J., "Valve Prosthesis", Rob & Smith's Operative Surgery, pp. 415-424, 1986.

Andersen, et al., "Transluminal implantation of artificial heart valves. Description of a new expandable aortic valve and initial results with implantation by catheter technique in closed chest pigs." European Heart Journal (1992), 13, 704-708.

Praz et al., "Compassionate use of the PASCAL transcatheter mitral valve repair system for patients with severe mitral regurgitation: a multicentre, prospective, observational, first-in-man study," Lancet vol. 390, pp. 773-780, 2017.

Umaña JP et al., Bow-tie 'mitral valve repair: an adjuvant technique for ischemic mitral regurgitation', Ann Thorac Surg., vol. 66, Issue-6, pp. 1640-1646, Nov. 1998.

Maisano F et al., 'The edge-to-edge technique: a simplified method to correct mitral insufficiency', Eur J Cardiothorac Surg., vol. 13, Issue-3, pp. 240-245, Mar. 1998.

Fucci et al., "Improved results with mitral valve repair using new surgical techniques", Eur J Cardiothorac Surg. 1995;Issue 9, vol. 11, pp. 621-626.

Beall AC Jr. et al.,"Clinical experience with a dacron velour-covered teflon-disc mitral-valve prosthesis", Ann Thorac Surg., vol. 5, Issue 5, pp. 402-410, May 1968.

Batista RJ et al., "Partial left ventriculectomy to treat end-stage heart disease", Ann Thorac Surg., vol. 64, Issue-3, pp. 634-638, Sep. 1997.

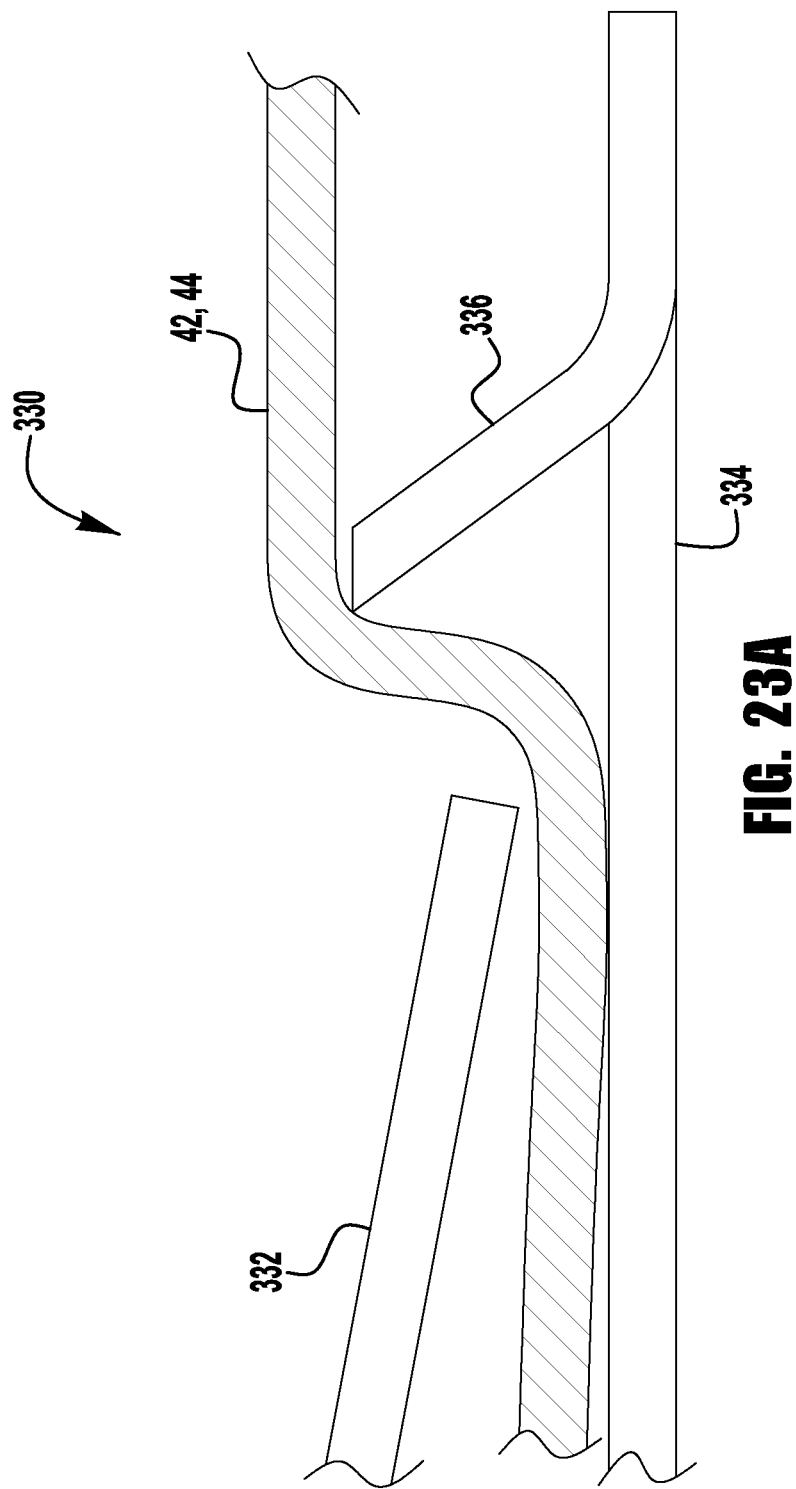

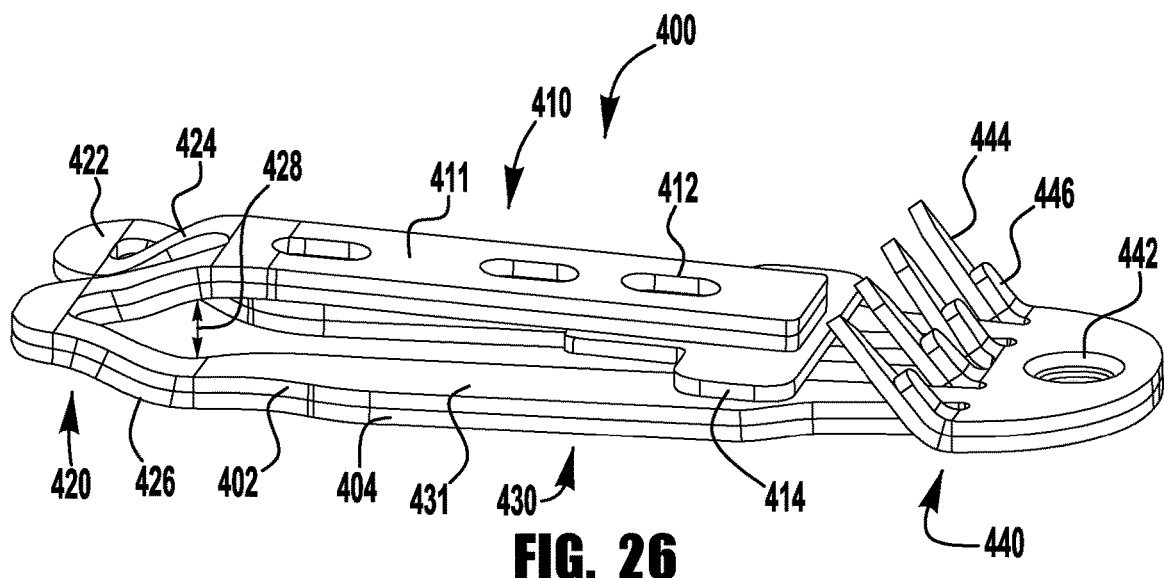

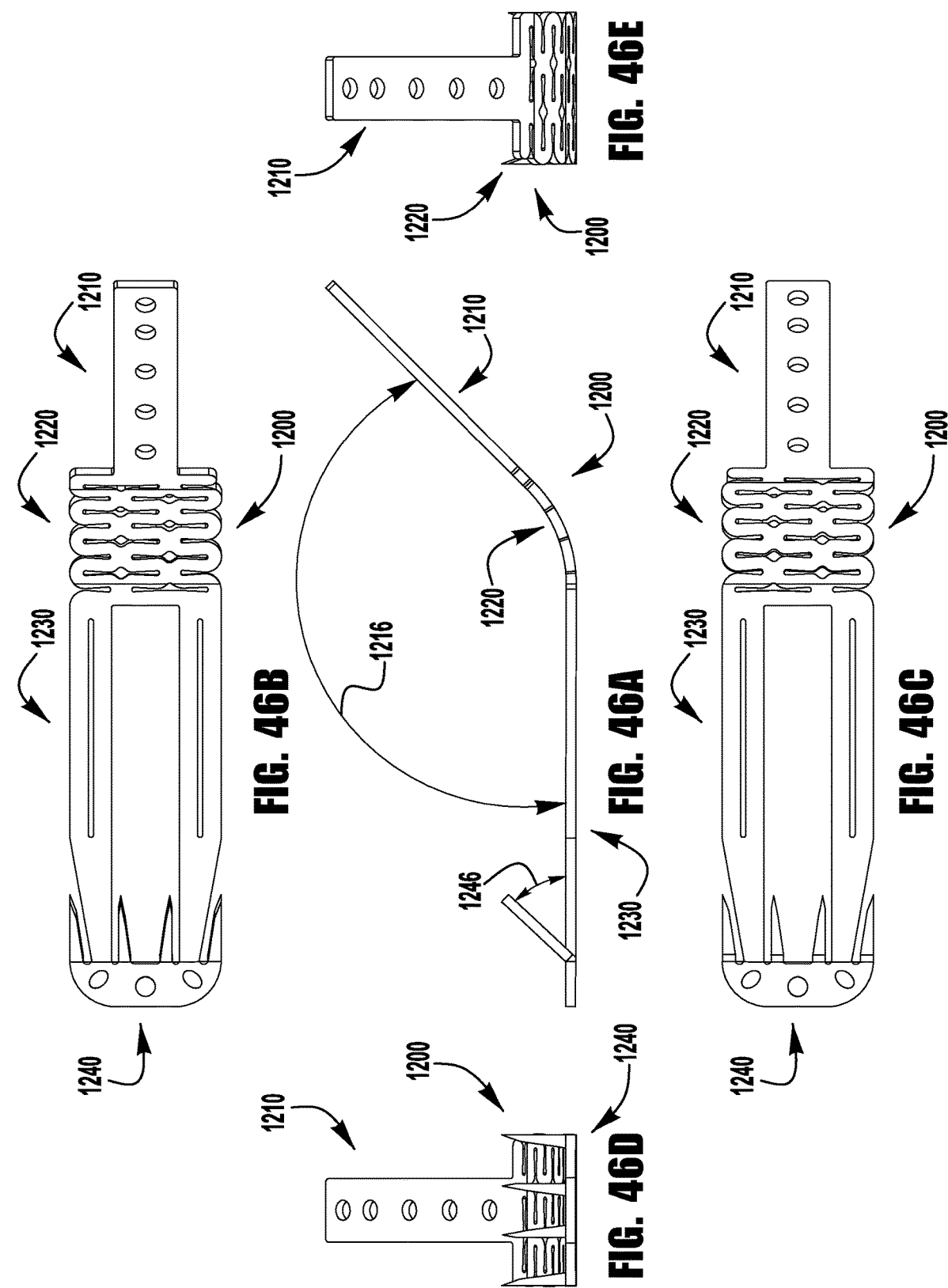

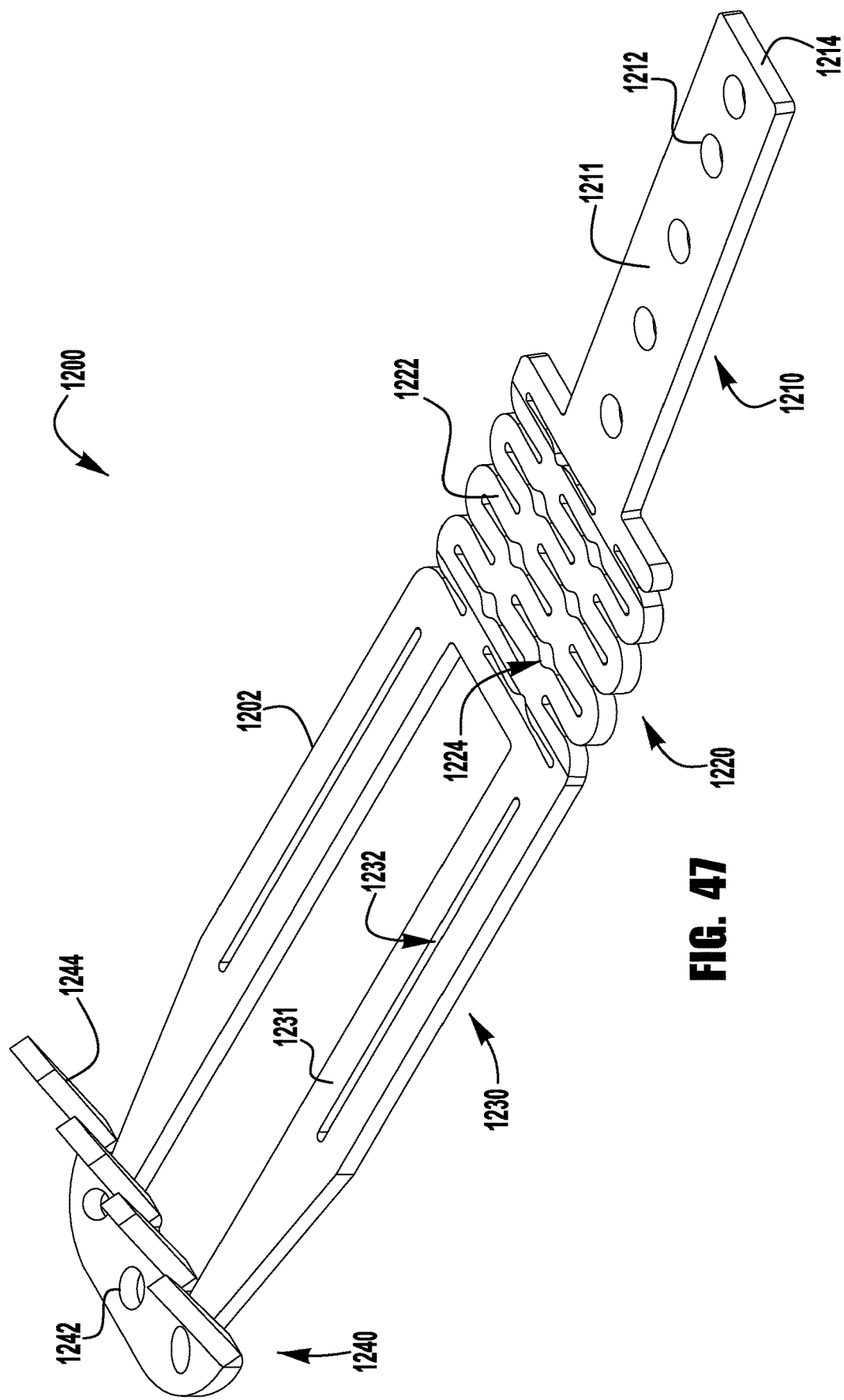

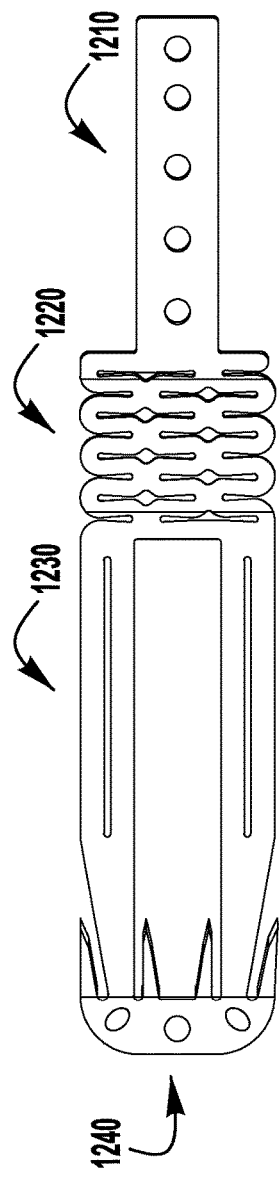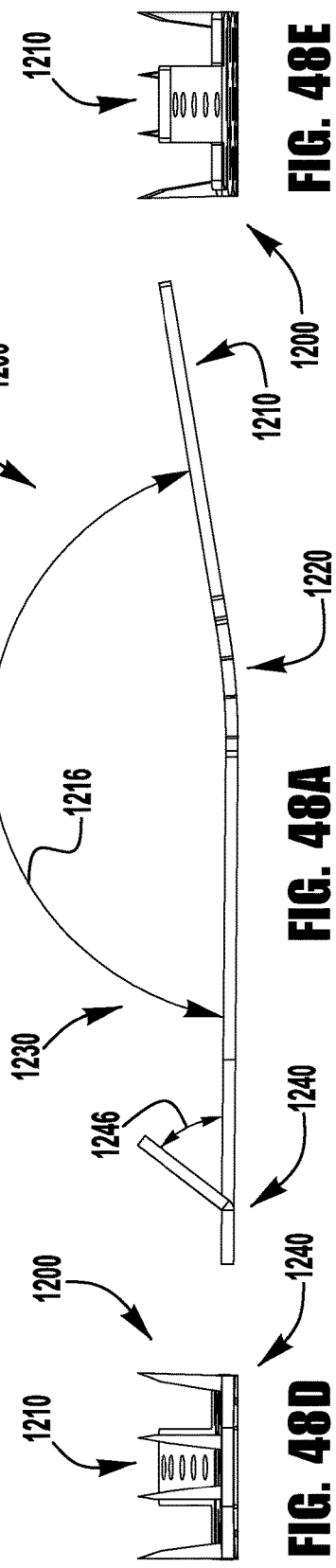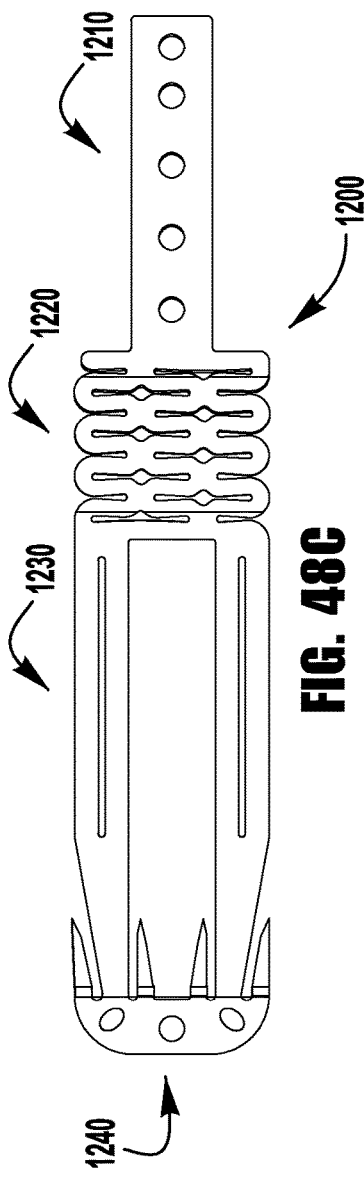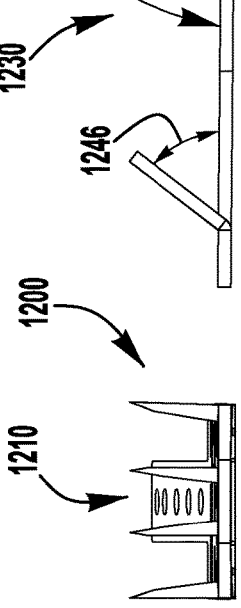

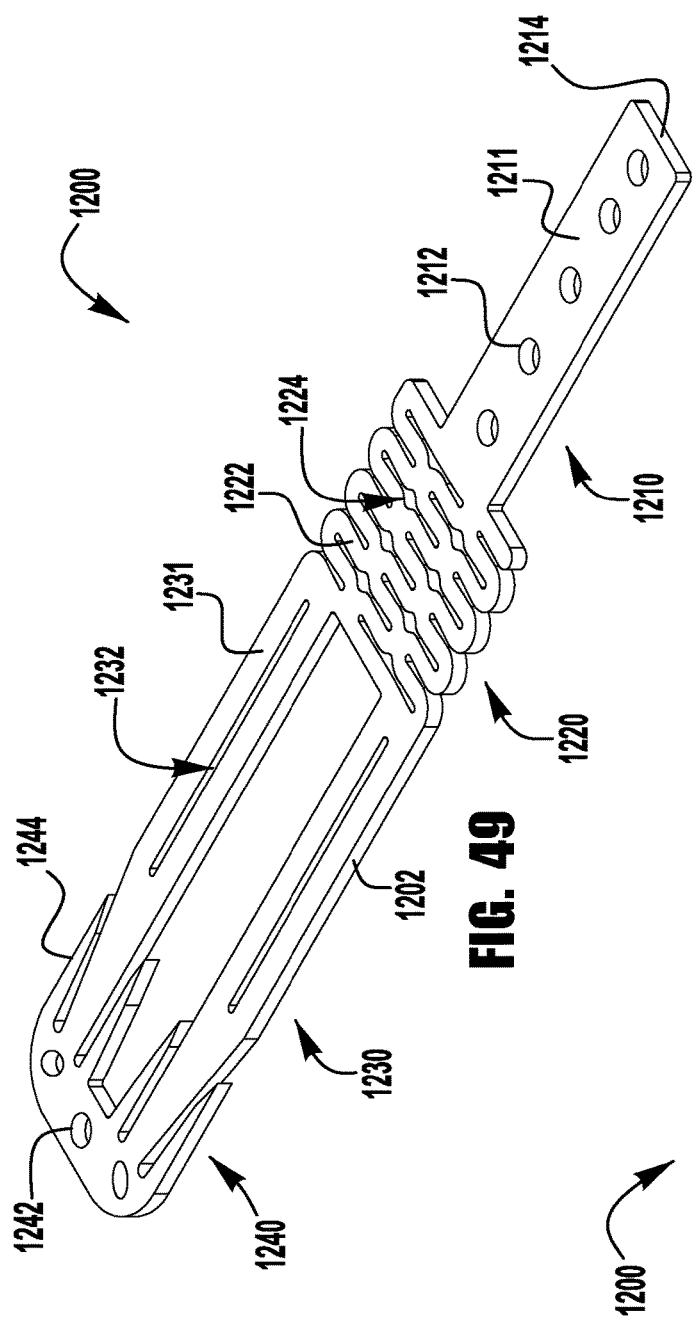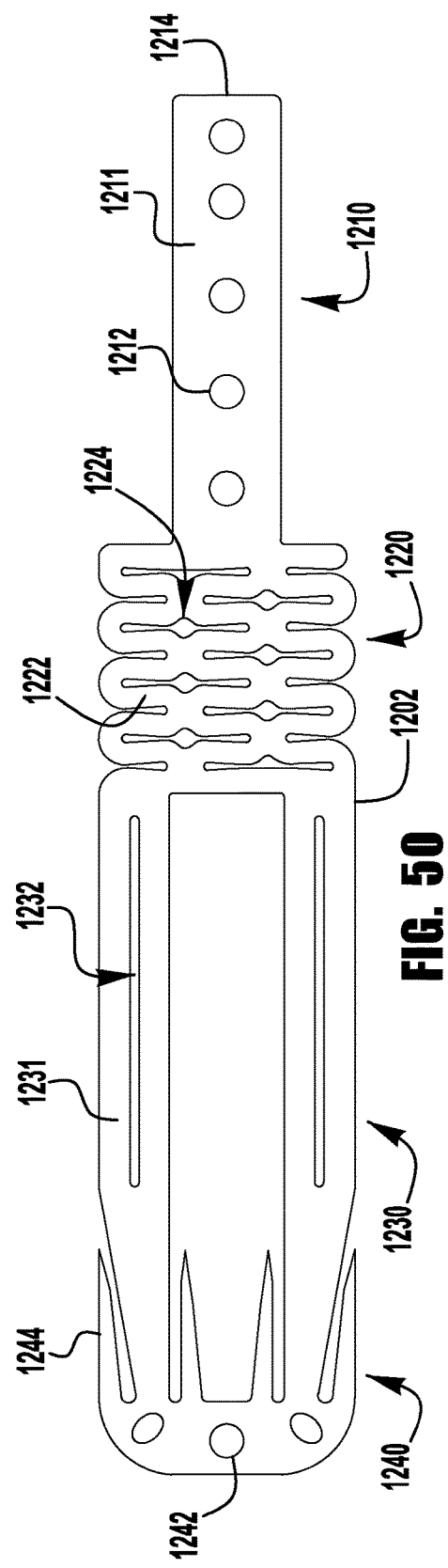

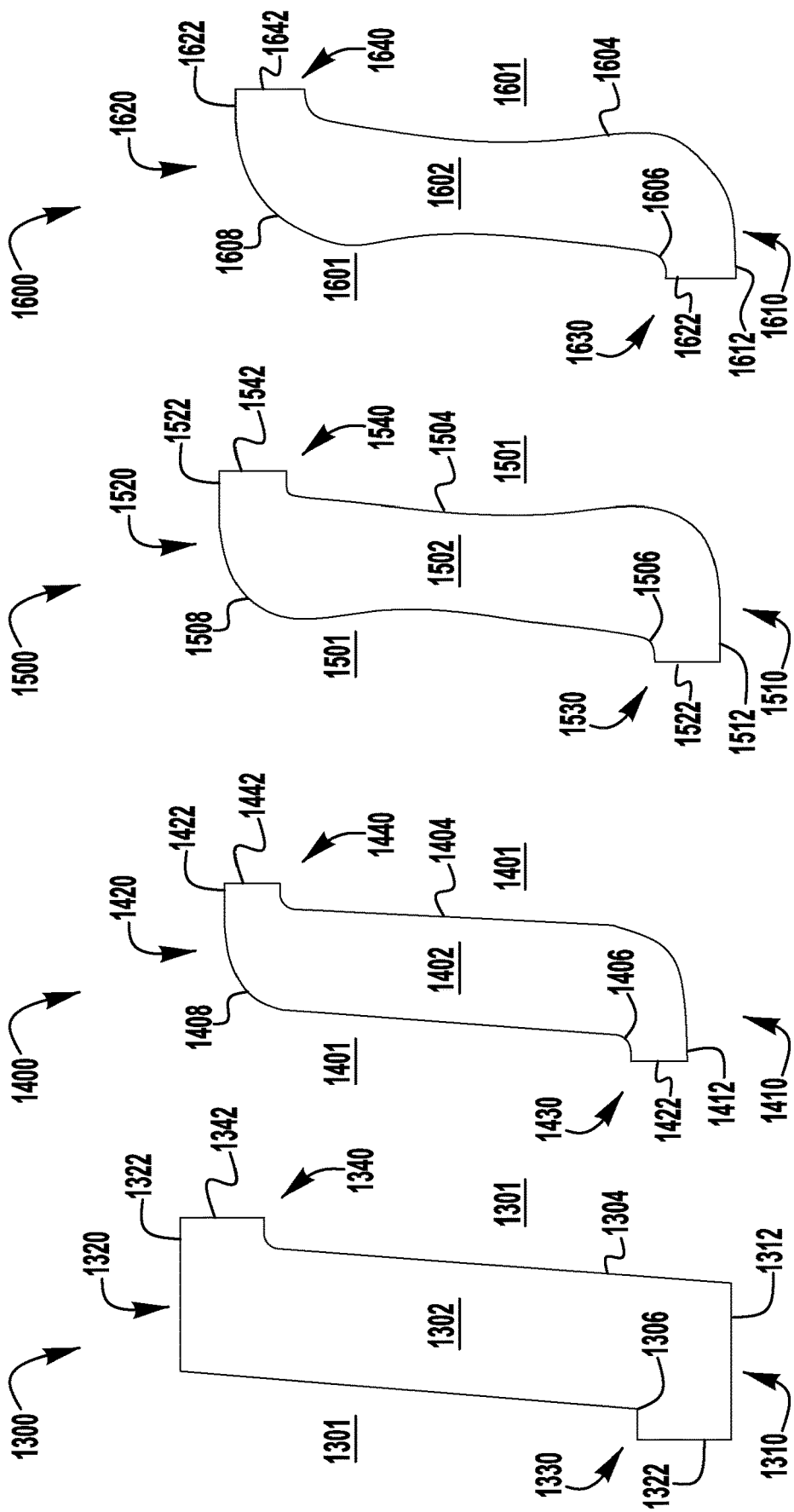

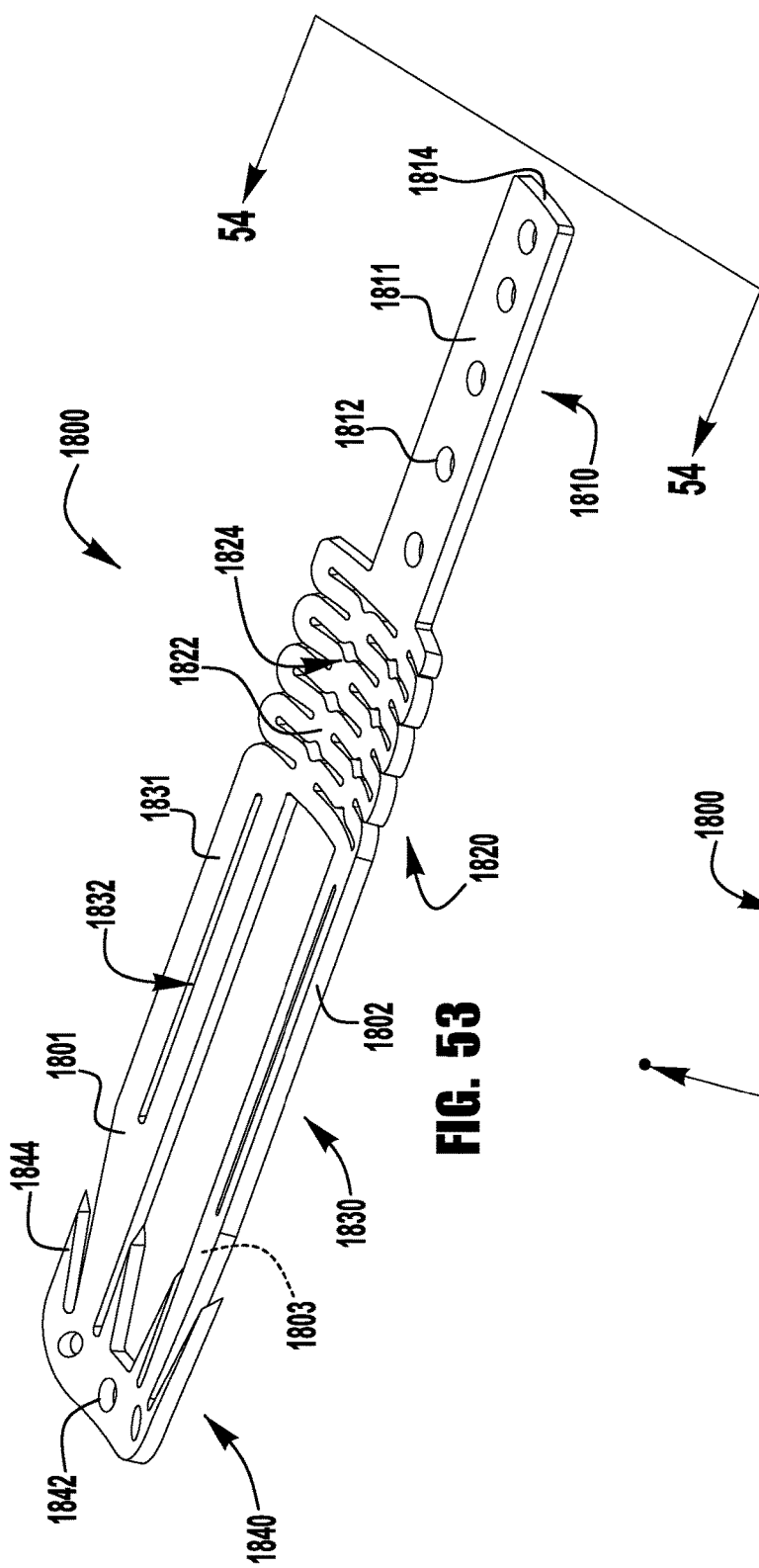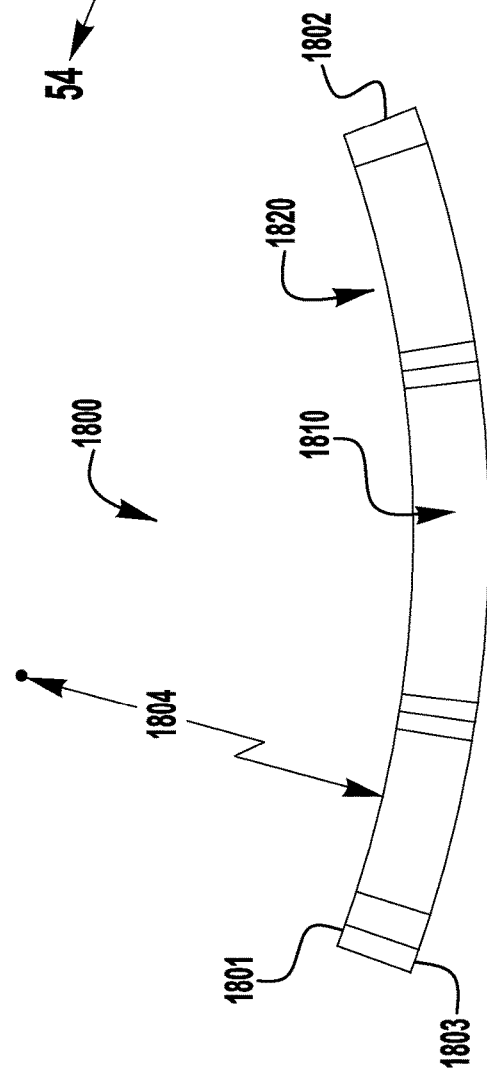

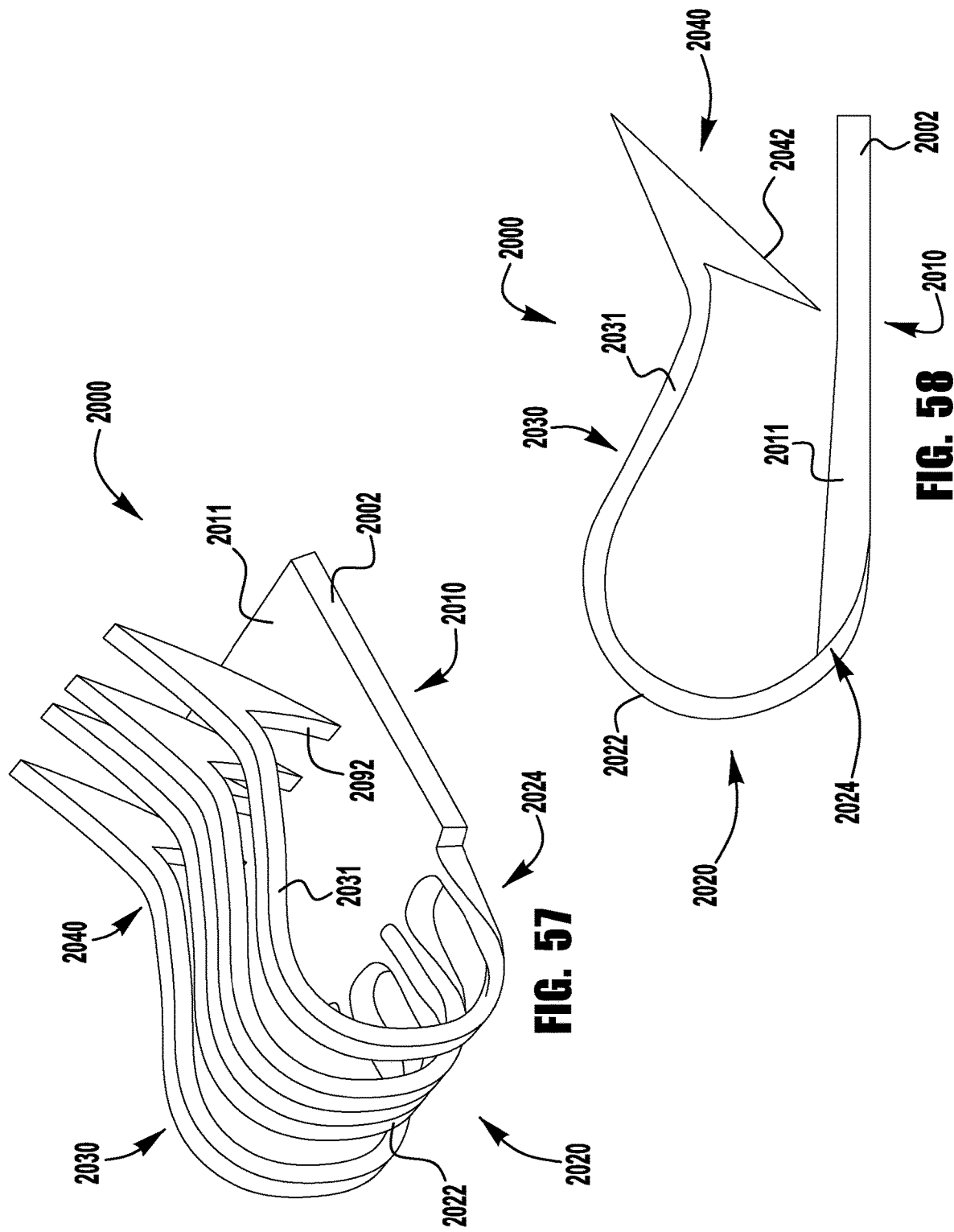

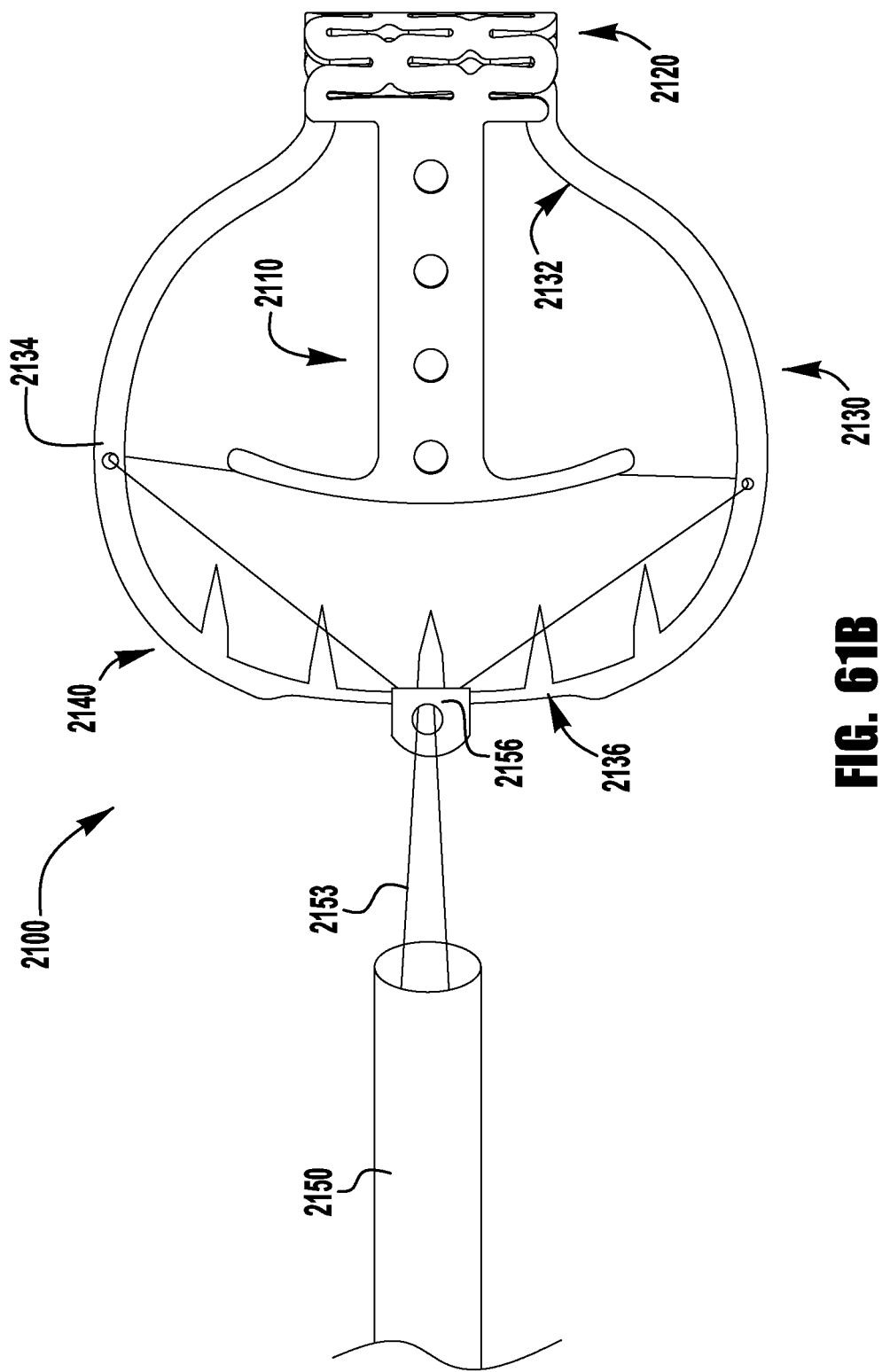

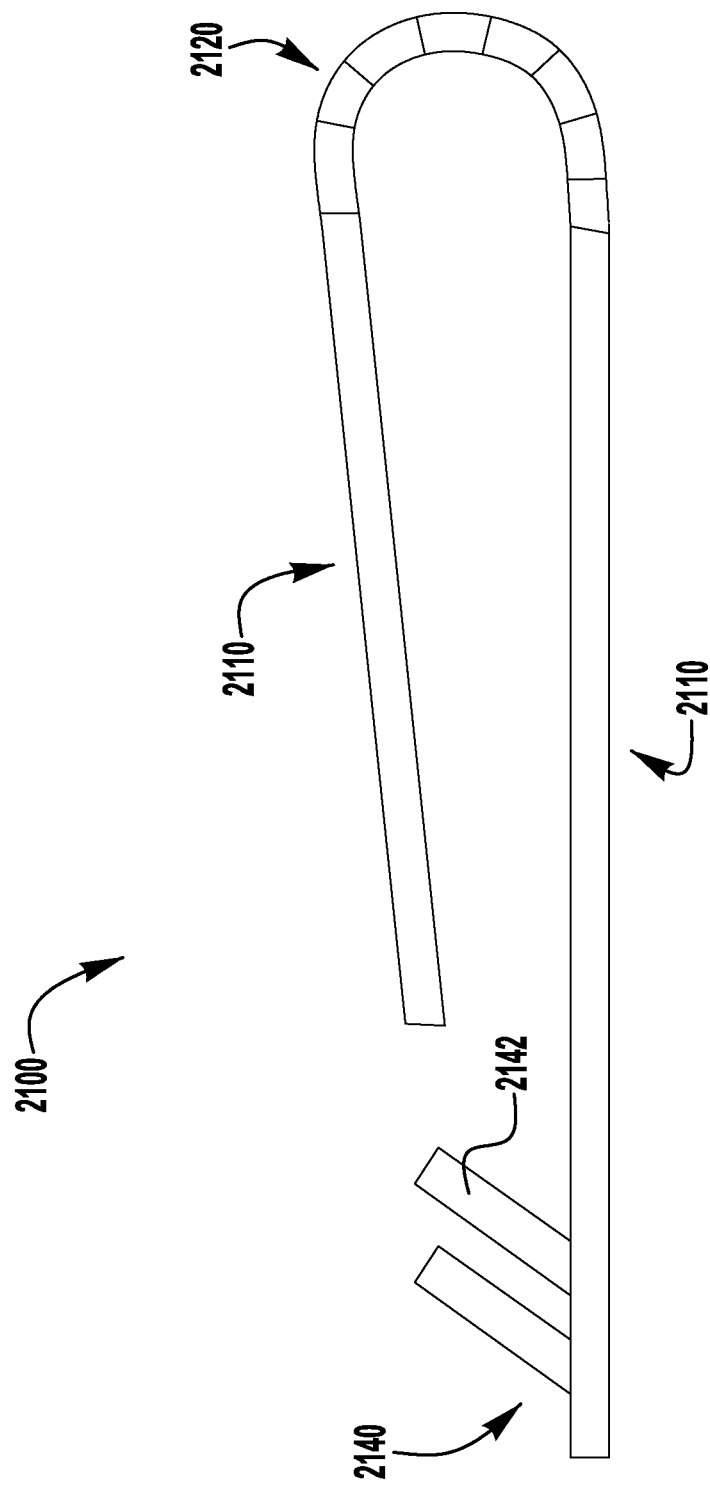

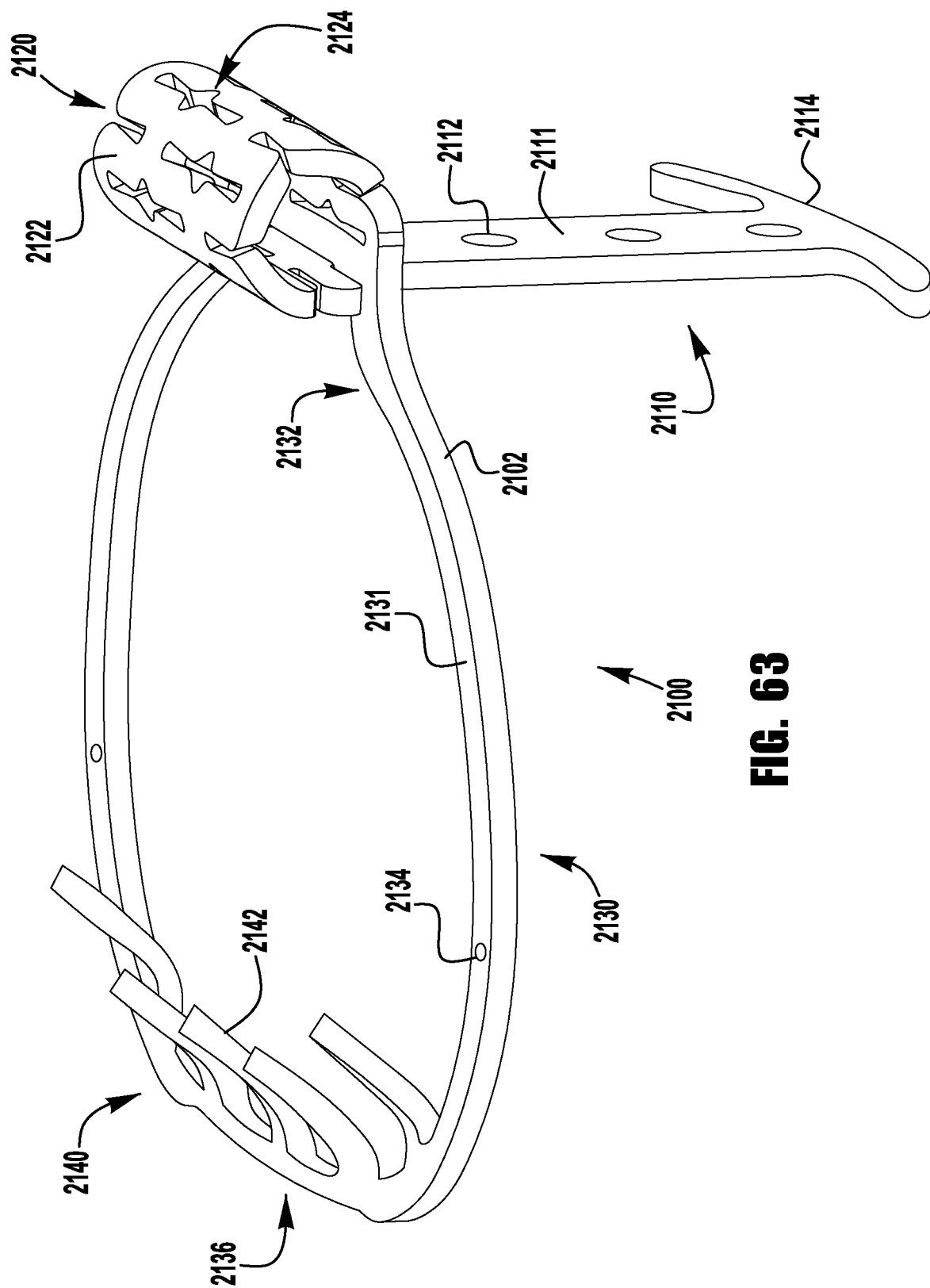

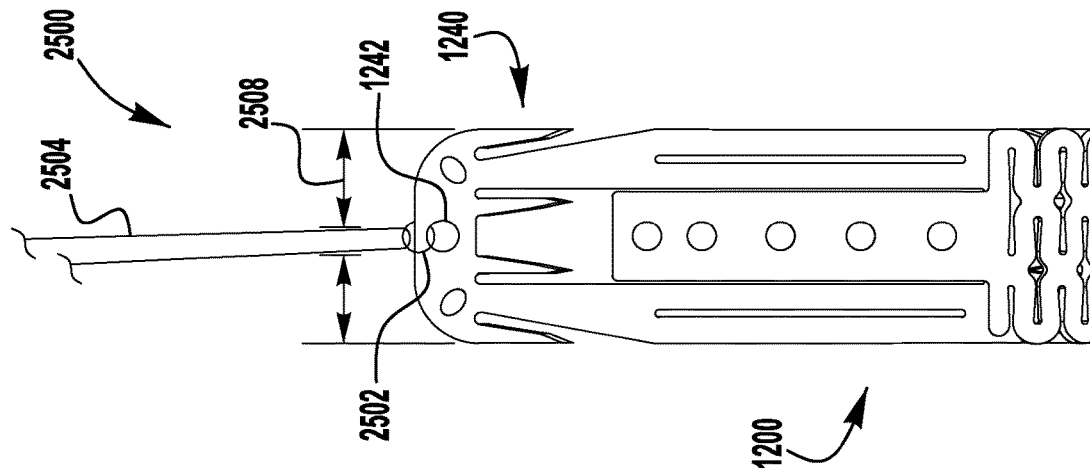
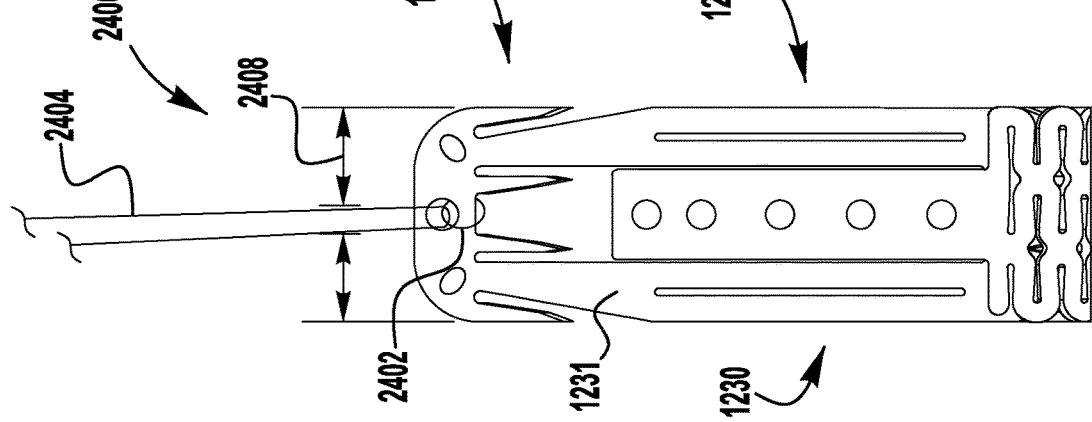
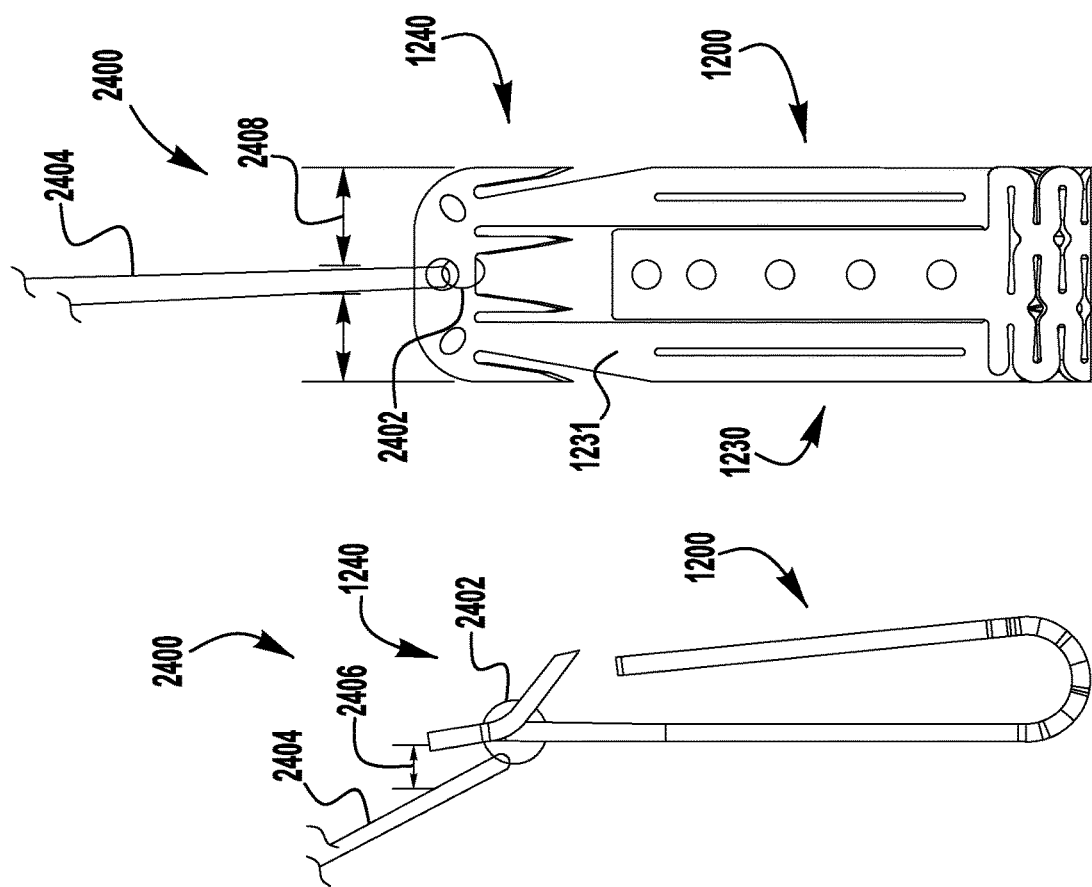

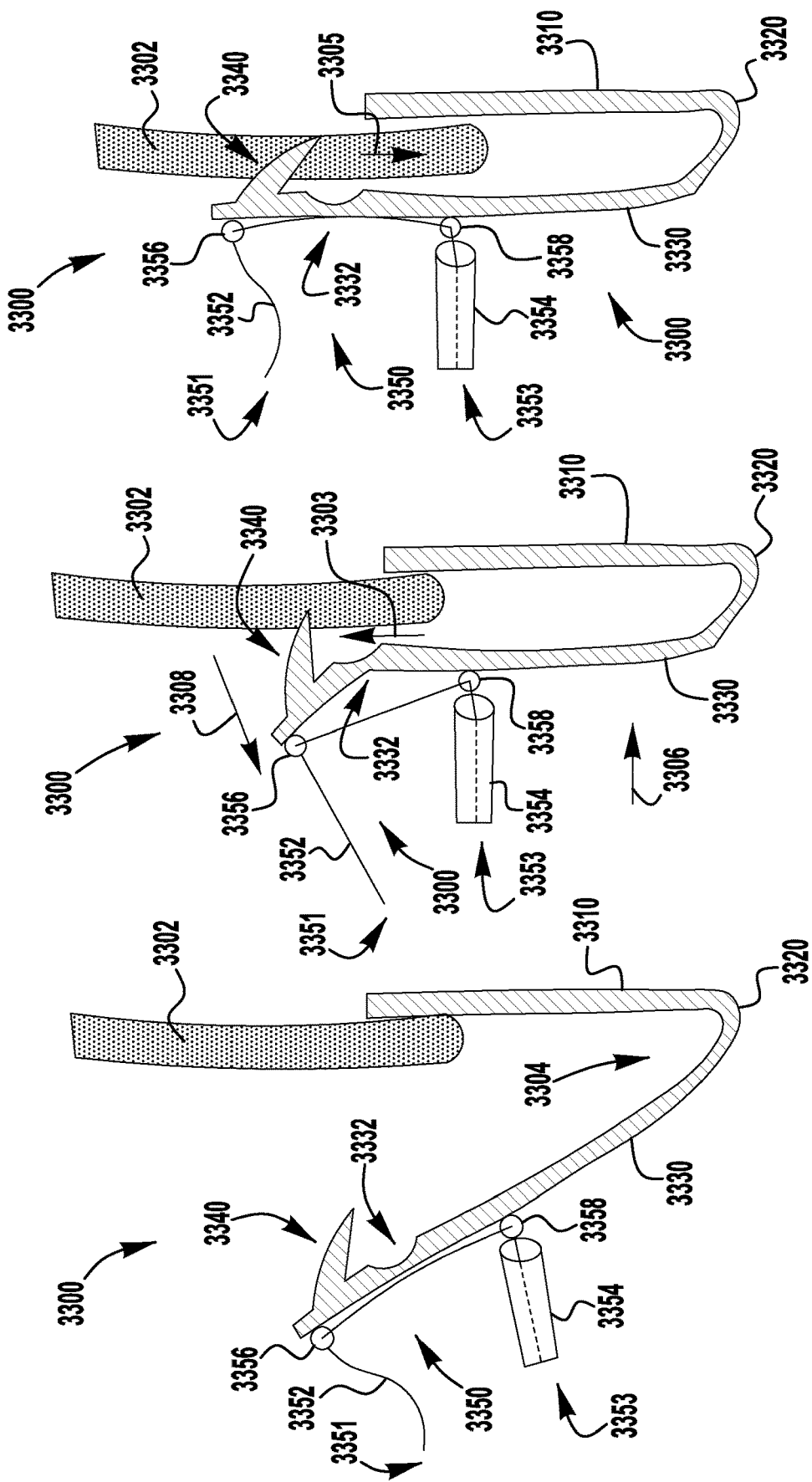

HEART VALVE SEALING DEVICES AND DELIVERY DEVICES THEREFOR

CROSS-REFERENCE TO RELATED APPLICATIONS

The present application is related to and claims any benefit of U.S. Provisional Application Ser. No. 62/486,835, filed on Apr. 18, 2017, titled HEART VALVE SEALING DEVICES AND DELIVERY DEVICES THEREFOR, the disclosure of which is incorporated herein by reference in its entirety.

TECHNICAL FIELD

The present application relates generally to prosthetic devices and related methods for helping to seal native heart valves and prevent or reduce regurgitation therethrough, as well as devices and related methods for implanting such prosthetic devices.

BACKGROUND OF THE INVENTION

The native heart valves (i.e., the aortic, pulmonary, tricuspid, and mitral valves) serve critical functions in assuring the forward flow of an adequate supply of blood through the cardiovascular system. These heart valves can be damaged, and thus rendered less effective, by congenital malformations, inflammatory processes, infectious conditions, or disease. Such damage to the valves can result in serious cardiovascular compromise or death. For many years the definitive treatment for such damaged valves was surgical repair or replacement of the valve during open heart surgery. However, open heart surgeries are highly invasive and are prone to many complications. Therefore, elderly and frail patients with defective heart valves often went untreated. More recently, transvascular techniques have been developed for introducing and implanting prosthetic devices in a manner that is much less invasive than open heart surgery. One particular transvascular technique that is used for accessing the native mitral and aortic valves is the trans-septal technique. The trans septal technique comprises inserting a catheter into the right femoral vein, up the inferior vena cava and into the right atrium. The septum is then punctured and the catheter passed into the left atrium.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets, extending downward from the annulus into the left ventricle. The mitral valve annulus can form a "D"-shaped, oval, or otherwise out-of-round cross-sectional shape having major and minor axes. The anterior leaflet can be larger than the posterior leaflet, forming a generally "C"-shaped boundary between the abutting free edges of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Mitral regurgitation occurs when the native mitral valve fails to close properly and blood flows into the left atrium from the left ventricle during the systolic phase of heart contraction. Mitral regurgitation is the most common form of valvular heart disease. Mitral regurgitation has different causes, such as leaflet prolapse, dysfunctional papillary muscles and/or stretching of the mitral valve annulus resulting from dilation of the left ventricle. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation. Central jet regurgitation occurs when the edges of the leaflets do not meet in the middle and thus the valve does not close and regurgitation is present.

Some prior techniques for treating mitral regurgitation in patients include surgically stitching the edges of the native mitral valve leaflets directly to one another. A catheter delivered clip has been used to attempt to clip the edges of the leaflets together, similar to the surgical stitching method. However, this clip has shortcomings, since it can only be used to clip the middle edges of the leaflets where they overlap by about 2 mm or more. Alternately, attempts have been made to use multiple clips on the commissures of the mitral valve, where there may be more overlap of the leaflets. This technique results in a longer operation time and also joins the patient's leaflets at the sides, restricting blood flow. Additionally, both the surgical and clip treatments are thought to create stress on patient leaflets.

Despite these prior techniques, there is a continuing need for improved devices and methods for treating mitral valve regurgitation.

SUMMARY

An implantable prosthetic has a coaption portion, paddles, and clasps. The paddles are extendable from a folded closed position to an open position. A clasp has a fixed arm attached to the paddle. The clasps also have a moveable arm having a barbed portion and an end that is rounded. A hinge portion connects the fixed arm to the moveable arm.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

These and other features and advantages of the present invention will become better understood with regard to the following description and accompanying drawings in which:

FIG. 23A shows a portion of mitral valve tissue captured by a barbed clasp;

FIG. 26 shows a barbed clasp for an implantable prosthetic device according to one embodiment;

FIG. 27 shows a barbed clasp for an implantable prosthetic device according to a second embodiment;

FIGS. 37-52 show a barbed clasp for an implantable prosthetic device according to a ninth embodiment;

FIGS. 53-55 show a barbed clasp for an implantable prosthetic device according to a tenth embodiment;

FIGS. 57-58 show a barbed clasp for an implantable prosthetic device according to a twelfth embodiment;

FIGS. 59-63 show a barbed clasp for an implantable prosthetic device according to a thirteenth embodiment;

FIGS. 69-73B show exemplary arrangements for securing actuating lines to an exemplary barbed clasp for an implantable prosthetic;

FIG. 81A-81C shows a barbed clasp for an implantable device according to a nineteenth embodiment;

DETAILED DESCRIPTION

Figure 1:
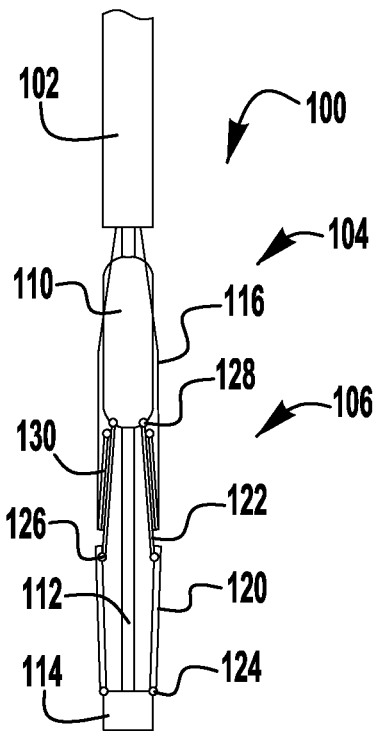
FIGS. 1-6 show an implantable prosthetic device according to a first embodiment, in various stages of deployment.

As described herein, when one or more components are described as being connected, joined, affixed, coupled, attached, or otherwise interconnected, such interconnection may be direct as between the components or may be indirect such as through the use of one or more intermediary components. Also as described herein, reference to a "member," "component," or "portion" shall not be limited to a single structural member, component, or element but can include an assembly of components, members, or elements. Also as described herein, the terms "substantially" and "about" are defined as at least close to (and includes) a given value or state (preferably within 10% of, more preferably within 1% of, and most preferably within 0.1% of).

A prosthetic device has a coaptation means or coaption element and at least one anchoring means or anchor. The coaption element is configured to be positioned within the native heart valve orifice to help form a more effective seal between the native leaflets, thereby reducing or preventing regurgitation. The coaption element can have a structure that is impervious to blood and that allows the native leaflets to close together on each side of the coaption element during ventricular systole to block blood from flowing from the left or right ventricle back into the left or right atrium, respectively. The prosthetic device can be configured to seal against two or three native valve leaflets; that is, the device may be used in the native mitral (bicuspid) and tricuspid valves. The coaption element is sometimes referred to herein as a spacer because the coaption element can fill a space between improperly functioning native mitral or tricuspid leaflets that do not close completely.

The coaption element can have various shapes. In some embodiments, the coaption element can have an elongated cylindrical shape having a round cross-sectional shape. In other embodiments, the coaption element can have an oval cross-sectional shape, a crescent cross-sectional shape, or various other non-cylindrical shapes. The coaption element can have an atrial or upper end positioned in or adjacent to the left atrium, a ventricular or lower end positioned in or adjacent to the left ventricle, and a side surface that extends between the native mitral leaflets. In embodiments configured for use in the tricuspid valve, the atrial or upper end is positioned in or adjacent to the right atrium, and the ventricular or lower end is positioned in or adjacent to the right ventricle, and the side surface that extends between the native tricuspid leaflets.

The anchor can be configured to secure the device to one or both of the native mitral leaflets such that the coaption element is positioned between the two native leaflets. In embodiments configured for use in the tricuspid valve, the anchor is configured to secure the device to one, two, or three of the tricuspid leaflets such that the coaption element is positioned between the three native leaflets. In some embodiments, the anchor can attach to the coaption element at a location adjacent the ventricular end of the coaption element. In some embodiments, the anchor can attach to an actuation means such as a shaft or actuation wire, to which the coaption element is also attached. In some embodiments, the anchor and the coaption element can be positioned independently with respect to each other by separately moving each of the anchor and the coaption element along the longitudinal axis of the shaft or actuation wire. In some embodiments, the anchor and the coaption element can be positioned simultaneously by moving the anchor and the coaption element together along the longitudinal axis of the shaft or actuation wire. The anchor can be configured to be positioned behind a native leaflet when implanted such that the leaflet is captured by the anchor.

The prosthetic device can be configured to be implanted via a delivery means such as a delivery sheath. The coaption element and the anchor can be compressible to a radially compressed state and can be self-expandable to a radially expanded state when compressive pressure is released. The device can be configured for the anchor to be expanded radially away from the still-compressed coaption element initially in order to create a gap between the coaption element and the anchor. A native leaflet can then be positioned in the gap. The coaption element can be expanded radially, closing the gap between the coaption element and the anchor and capturing the leaflet between the coaption element and the anchor. In some embodiments, the anchor and coaption element are optionally configured to self-expand. The implantation methods for various embodiments can be different, and are more fully discussed below with respect to each embodiment. Additional information regarding these and other delivery methods can be found in U.S. Pat. No. 8,449,599 and U.S. Patent Application Publication Nos. 2014/0222136, and 2014/0067052, 2016/0331523 each of which is incorporated herein by reference in its entirety.

The disclosed prosthetic devices are prevented from atrial embolization by having the anchor hooked to a leaflet, taking advantage of the tension from native chordae tendineae to resist high systolic pressure urging the device toward the left atrium. During diastole, the devices can rely on the compressive and retention forces exerted on the leaflet that is captured by the anchor to resist embolization into the left ventricle.

Referring now to FIGS. 1-6, an implantable prosthetic device 100 is shown in various stages of deployment. The device 100 is deployed from a delivery sheath 102 and includes a coaption portion 104 and an anchor portion 106. The coaption portion 104 of the device 100 includes a coaption element 110 that is adapted to be implanted between the leaflets of the native mitral valve and is slideably attached to an actuation wire or shaft 112. The anchor portion 106 is actuatable between open and closed conditions and can take a wide variety of forms, such as, for example, paddles, gripping elements, or the like. Actuation of the actuation wire 112 opens and closes the anchor portion 106 of the device 100 to capture the mitral valve leaflets during implantation. The actuation wire or shaft 112 may take a wide variety of different forms. For example, the actuation wire or shaft may be threaded such that rotation of the actuation wire or shaft moves the anchor portion 106 relative to the coaption portion 104. Or, the actuation wire or shaft may be unthreaded, such that pushing or pulling the actuation wire or shaft 112 moves the anchor portion 106 relative to the coaption portion 104.

The anchor portion 106 of the device 100 includes outer paddles or gripping elements 120 and inner paddles or gripping elements 122 that are connected between a cap 114 and the coaption element 110 by portions 124, 126, 128. The portions 124, 126, 128 may be hinged and/or flexible to move between all of the positions described below. The actuation wire 112 extends through the delivery sheath and the coaption element 110 to the cap 114 at the distal end of the anchor portion 106. Extending and retracting the actuation wire 112 increases and decreases the spacing between the coaption element 110 and the cap 114, respectively. An attaching means or collar (not shown) removably attaches the coaption element 110 to the delivery sheath 102 so that the coaption element 110 slides along the actuation wire 112 during actuation to open and close the paddles 120, 122 of the anchor portion 106.

Figure 3:
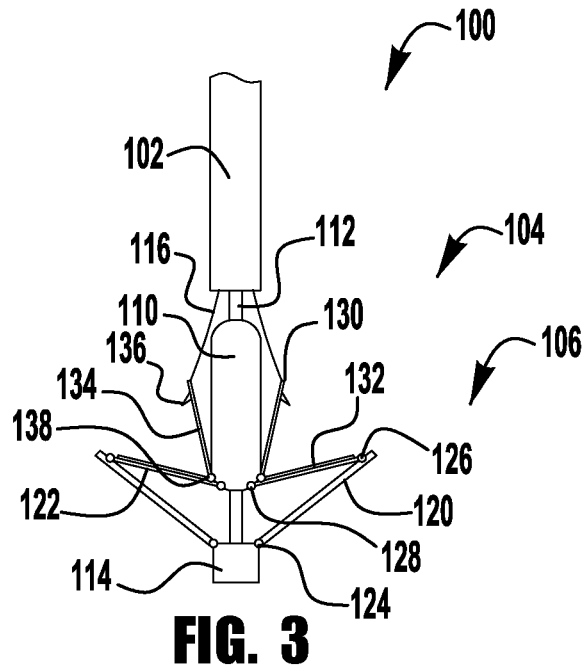

Referring to FIG. 3, the barbed clasps 130 include a base or fixed arm 132, a moveable arm 134, barbs 136, and a hinge portion 138. The fixed arms 132 are attached to the inner paddles 122, with the hinge portion 138 disposed proximate the coaption element 110. The hinge portion 138 provides a spring force between the fixed and moveable arms 132, 134 of the barbed clasp 130. The hinge portion 138 can be any suitable hinge, such as a flexible hinge, a spring hinge, a pivot hinge, or the like. In certain embodiments, the hinge portion 138 is a flexible piece of material integrally formed with the fixed and moveable arms 132, 134. The fixed arms 132 are attached to the inner paddles 122 and remain stationary relative to the inner paddles 122 when the moveable arms 134 are opened to open the barbed clasps 130 and expose the barbs 136. The barbed clasps 130 are opened by applying tension to actuation lines 116 attached to the ends of the moveable arms 134, thereby causing the moveable arms 134 to pivot on the hinge portions 138.

During implantation, the paddles 120, 122 are opened and closed to capture the native mitral valve leaflets between the paddles 120, 122 and the coaption element 110. The barbed clasps 130 further secure the native leaflets by engaging the leaflets with barbs 136 and pinching the leaflets between the moveable and fixed arms 134, 132. The barbs 136 of the barbed clasps 130 increase friction with the leaflets or may partially or completely puncture the leaflets. The actuation lines 116 can be actuated independently so that each barbed clasp 130 can be opened and closed independently. Independent operation allows one leaflet to be captured at a time, or for the repositioning of a clasp 130 on a leaflet that was insufficiently captured, without altering a successful grasp on the other leaflet. The barbed clasps 130 not only open and close independent from each other but can fully be opened and closed independent from the position of the inner paddle 122, thereby allowing leaflets to be captured in a variety of positions as the particular situation requires.

The barbed clasps 130 can be opened independently by pulling on an attached actuating means or actuation line 116 that extends through the delivery sheath 102 to the end of the barbed clasp 130. The actuation line 116 can take a wide variety of forms, such as, for example, a line, a suture, a wire, a rod, a catheter, or the like. The barbed clasps 130 can be spring loaded so that in the closed position the barbed clasps 130 continue to provide a pinching force on the captured native leaflet. This pinching force remains constant regardless of the position of the inner paddles 122. Barbs 136 of the barbed clasps 130 can pierce the native leaflets to further secure the native leaflets.

Referring now to FIG. 1, the device 100 is shown in an elongated or fully open condition for deployment from the delivery sheath. The device 100 is loaded in the delivery sheath in the fully open position, because the fully open position takes up the least space and allows the smallest catheter to be used (or the largest device 100 to be used for a given catheter size). In the elongated condition the cap 114 is spaced apart from the coaption element 110 such that the paddles 120, 122 of the anchor portion 106 are inverted or fully open. In some embodiments, an angle formed between the interior of the outer and inner paddles 120, 122 is approximately 180 degrees. The barbed clasps 130 are kept in a closed condition during deployment through the delivery sheath 102 so that the barbs 136 (FIG. 3) do not catch or damage the sheath or tissue in the patient's heart.

Figure 1A:
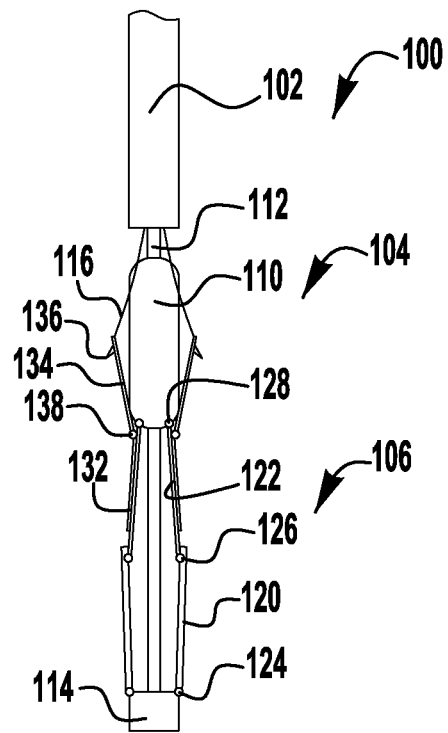

Referring now to FIG. 1A, the device 100 is shown in an elongated detangling condition, similar to FIG. 1, but with the barbed clasps 130 in a fully open position, ranging from about 140 degrees to about 200 degrees, to about 170 degrees to about 190 degrees, or about 180 degrees between fixed and moveable portions of the barbed clasps 130. Fully opening the device 100 and the clasps 130 has been found to improve ease of detanglement from anatomy of the patient during implantation of the device 100.

Figure 2:
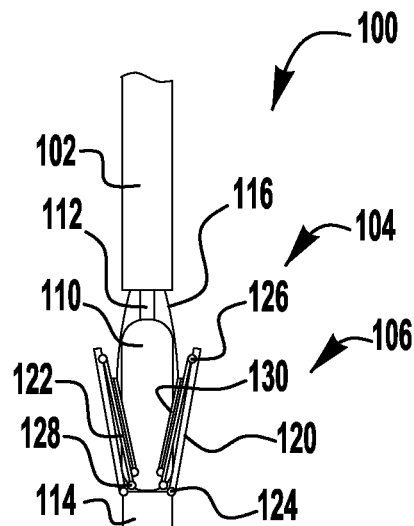

Referring now to FIG. 2, the device 100 is shown in a shortened or fully closed condition. The compact size of the device 100 in the shortened condition allows for easier maneuvering and placement within the heart. To move the device 100 from the elongated condition to the shortened condition, the actuation wire 112 is retracted to pull the cap 114 towards the coaption element 110. The hinges or flexible connections 126 between the outer paddle 120 and inner paddle 122 are limited in movement such that compression forces acting on the outer paddle 120 from the cap 114 being retracted towards the coaption element 110 cause the paddles or gripping elements 120, 122 to move radially outward. During movement from the open to closed position, the outer paddles 120 maintain an acute angle with the actuation wire 112. The outer paddles 120 can optionally be biased toward a closed position. The inner paddles 122 during the same motion move through a considerably larger angle as they are oriented away from the coaption element 110 in the open condition and collapse along the sides of the coaption element 110 in the closed condition. In certain embodiments, the inner paddles 122 are thinner and/or narrower than the outer paddles 120, and the hinge or flexible portions 126, 128 connected to the inner paddles 122 are thinner and/or more flexible to allow more movement than the hinge or flexible portion 124 connecting the outer paddle 124 to the cap 114.

Figure 4:
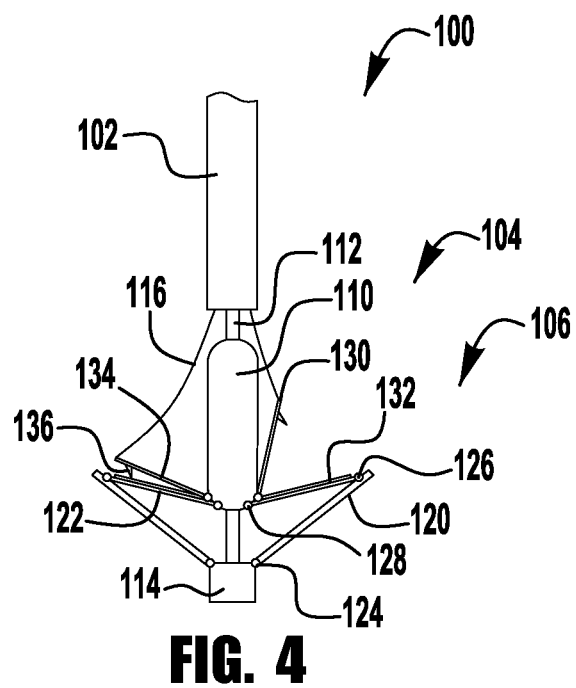
Figure 5:
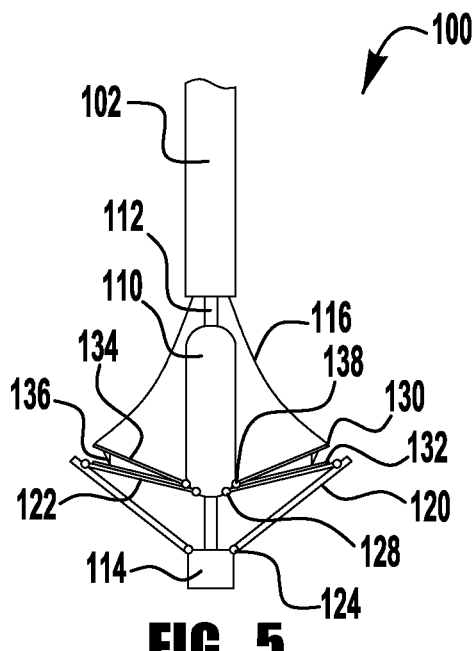

Referring now to FIGS. 3-5, the device 100 is shown in a partially open, capture-ready condition. To transition from the fully closed to the partially open condition, the actuation wire 112 is extended to push the cap 114 away from the coaption element 110, thereby pulling on the outer paddles 120, which in turn pulls on the inner paddles 122, causing the anchor portion 106 to partially unfold. The actuation lines 116 are also retracted to open the clasps 130 so that the leaflets can be captured.

Referring now to FIG. 4, one of the actuation lines 116 is extended to allow one of the clasps 130 to close. Referring now to FIG. 5, the other actuation line 116 is extended to allow the other clasp 130 to close. Either or both of the actuation lines 116 may be repeatedly actuated to repeatedly open and close the barbed clasps 130.

Figure 6:
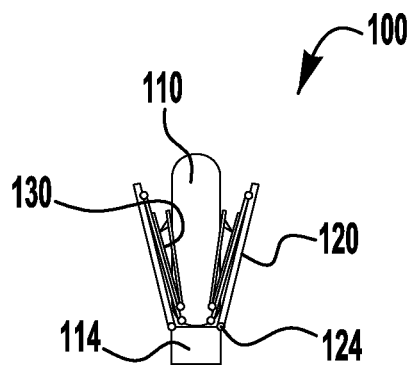

Referring now to FIG. 6, the device 100 is shown in a fully closed and deployed condition. The delivery sheath 102 and actuation wire 112 are retracted and the paddles 120, 122 and clasps 130 remain in a fully closed position. Once deployed, the device 100 may be maintained in the fully closed position with a mechanical latch or may be biased to remain closed through the use of spring materials, such as steel, other metals, plastics, composites, etc. or shape-memory alloys such as Nitinol. For example, the hinged or flexible portions 124, 126, 128, 138, and/or the inner and outer paddles 122, and/or an additional biasing component (see component 224 in FIG. 13) may be formed of metals such as steel or shape-memory alloy, such as Nitinol—produced in a wire, sheet, tubing, or laser sintered powder—and are biased to hold the outer paddles 120 closed around the coaption element 110 and the barbed clasps 130 pinched around native leaflets. Similarly, the fixed and moveable arms 132, 134 of the barbed clasps 130 are biased to pinch the leaflets. In certain embodiments, the hinge portions 124, 126, 128, 138, and/or the inner and outer paddles 122, and/or an additional biasing component (see component 224 in FIG. 13) may be formed of any other suitably elastic material, such as a metal or polymer material, to maintain the device in the closed condition after implantation.

Figure 7:
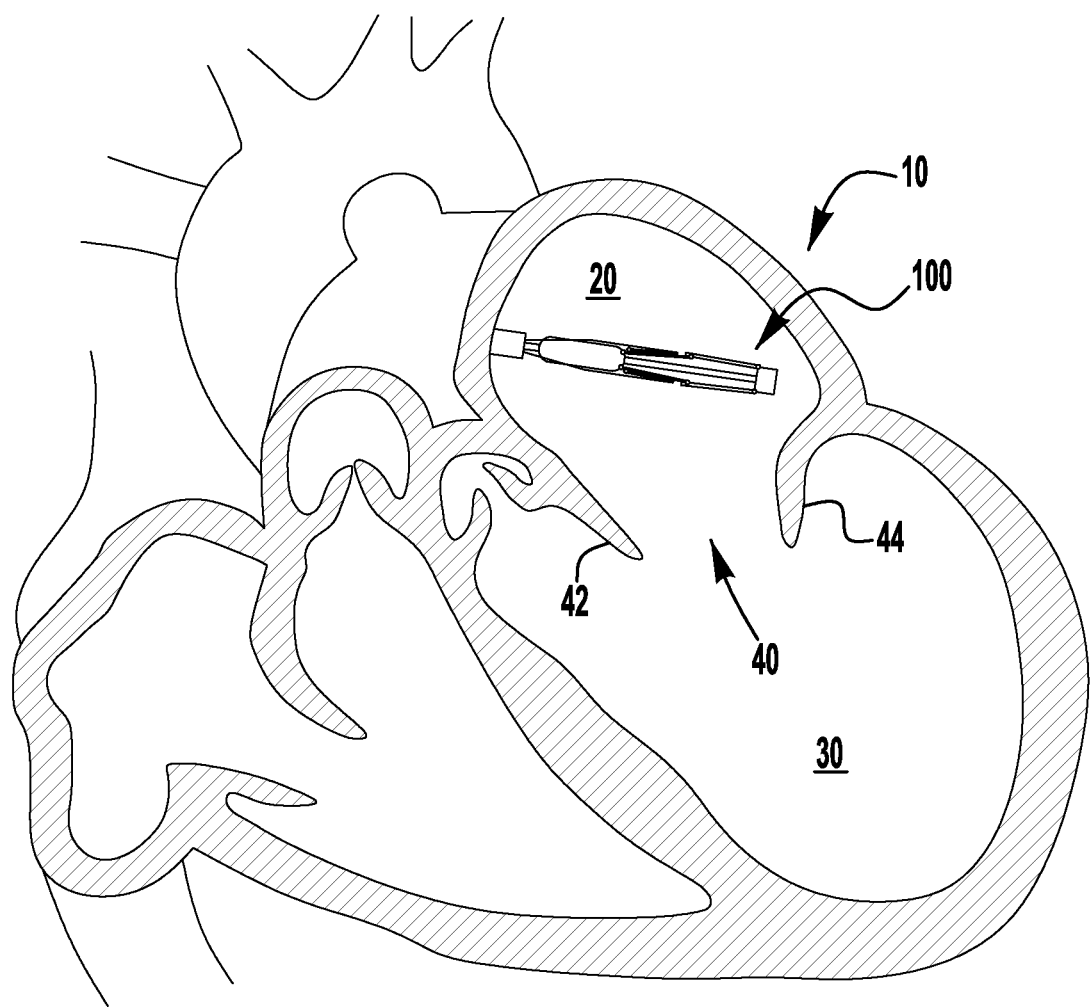
FIGS. 7-12 show the implantable prosthetic device of FIGS. 1-6 being delivered and implanted within the native mitral valve.
Figure 8:
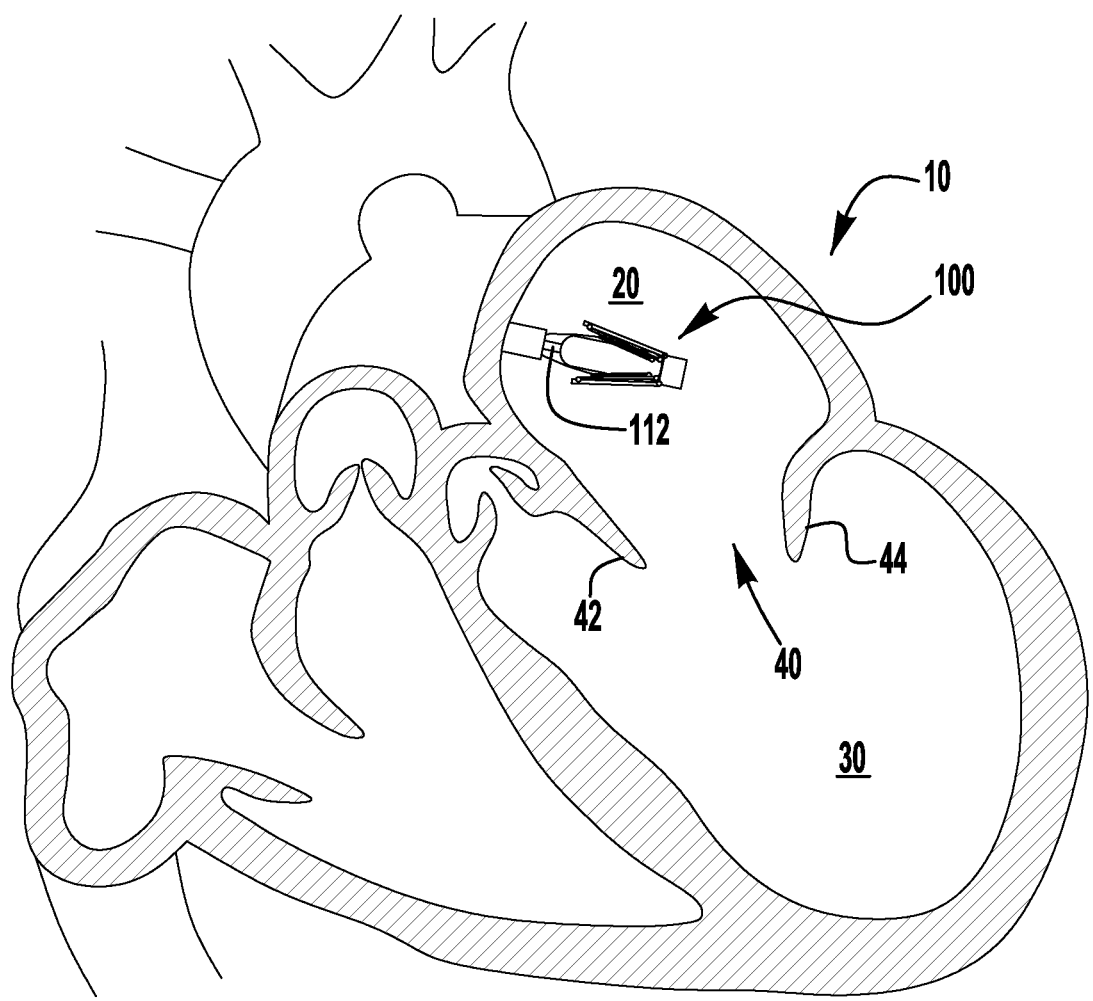
Figure 9:
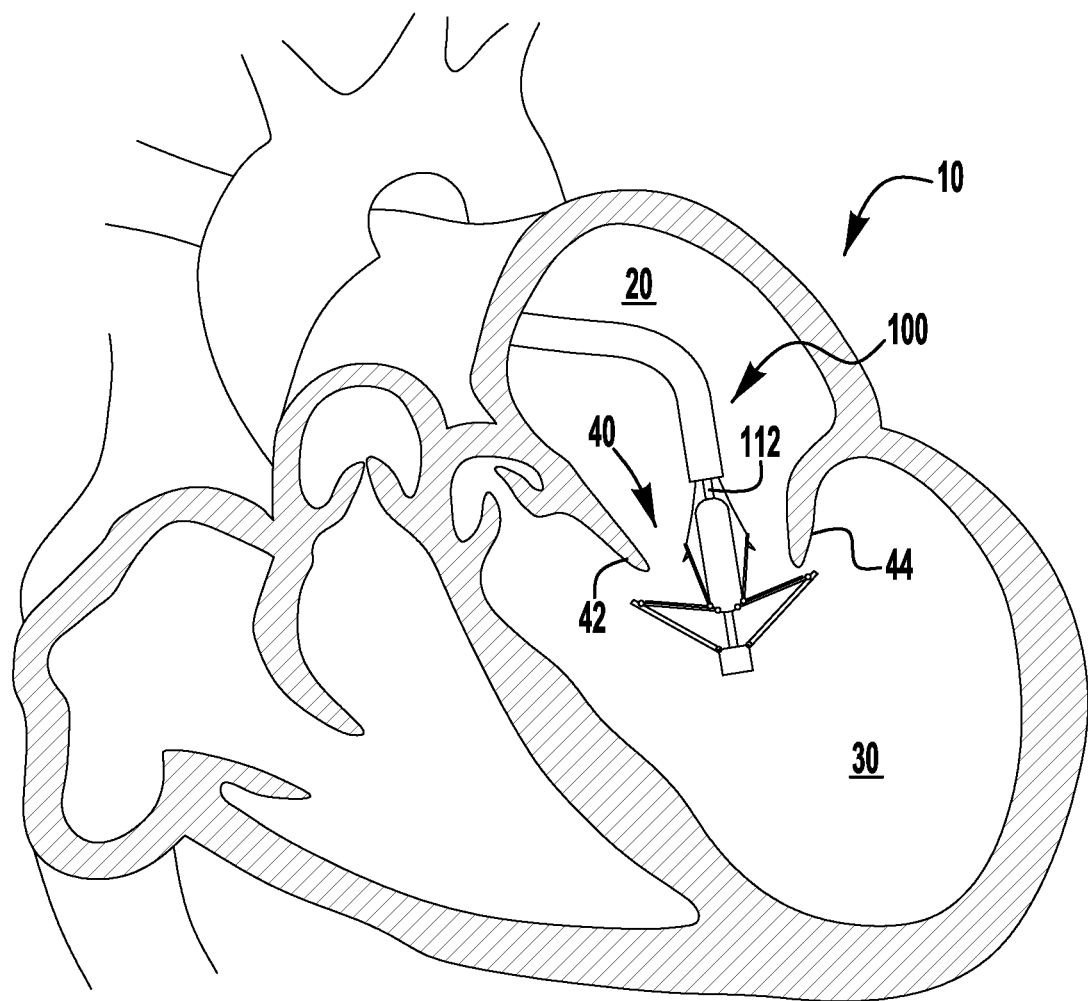
Figure 10:
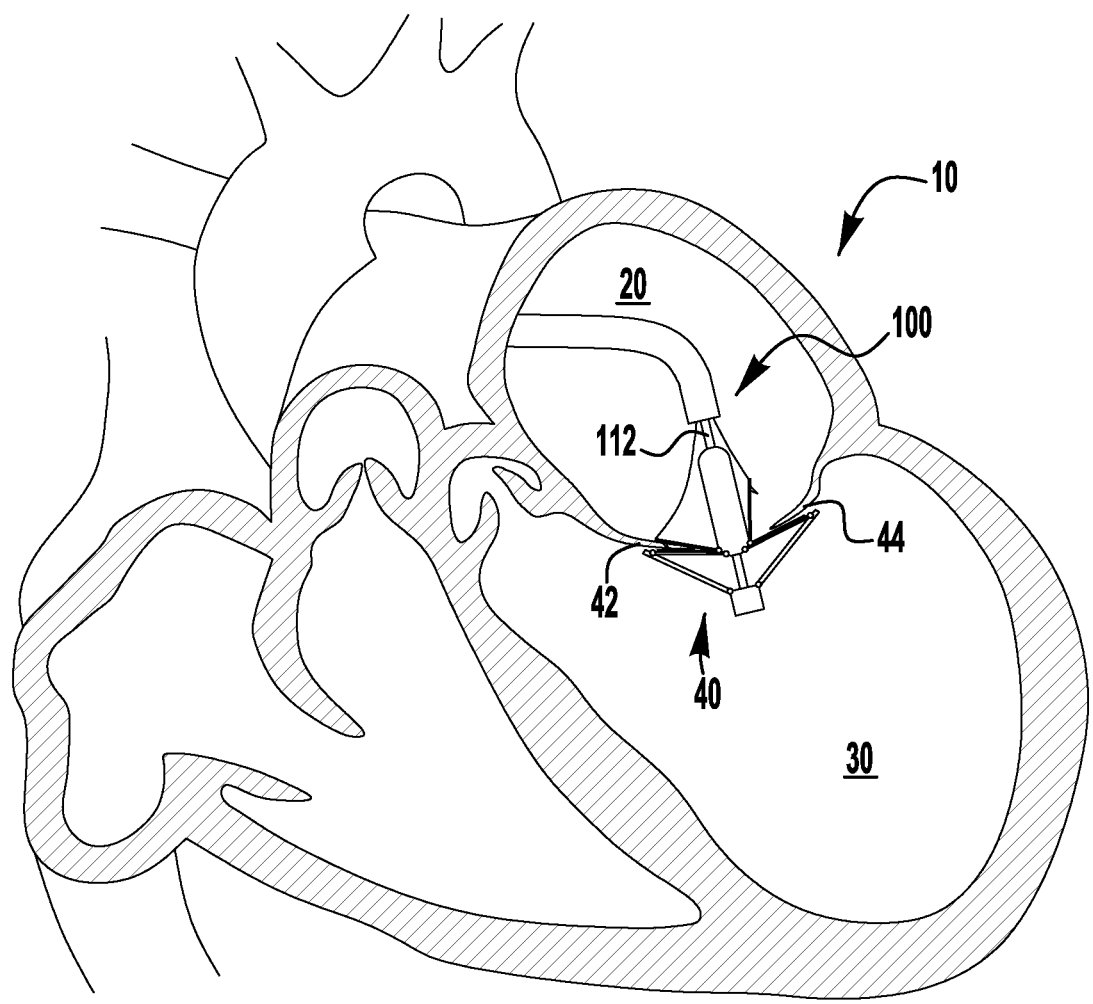
Figure 11:
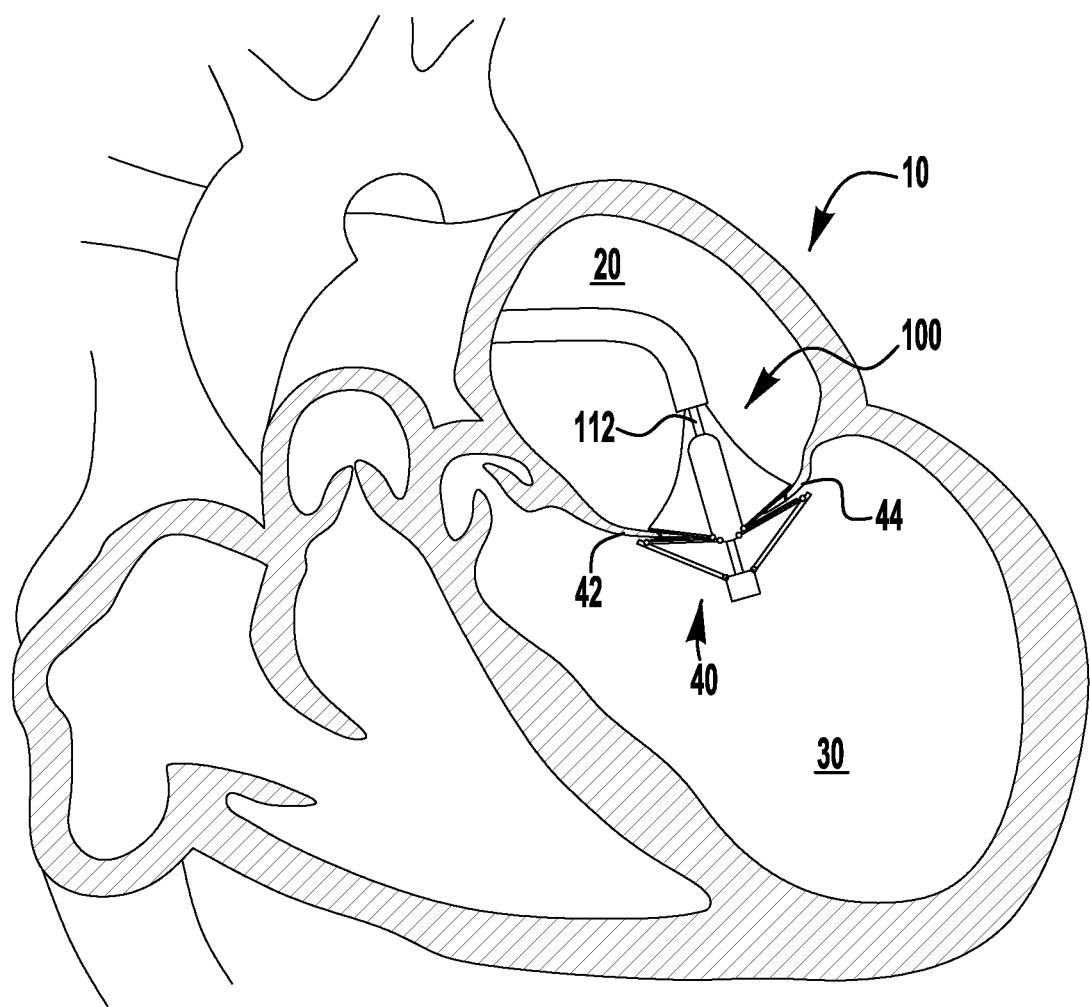
Figure 12:
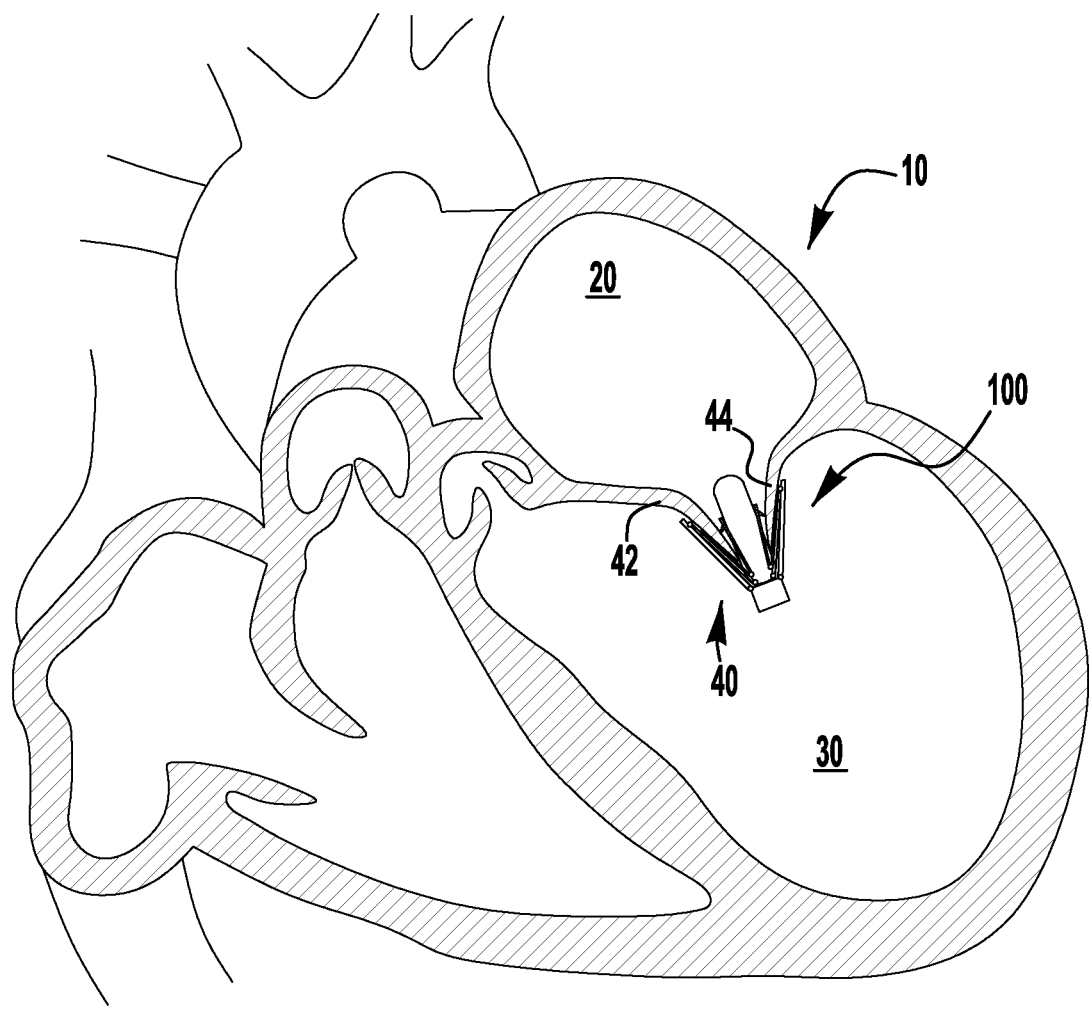

Referring now to FIGS. 7-12, the implantable device 100 of FIGS. 1-6 is shown being delivered and implanted within a native mitral valve 40 of a heart 10. Referring now to FIG. 7, the delivery sheath is inserted into the left atrium 20 through the septum and the device 100 is deployed from the delivery sheath in the fully open condition. The actuation wire 112 is then retracted to move the device 100 into the fully closed condition shown in FIG. 8. As can be seen in FIG. 9, the device 100 is moved into position within the mitral valve 40 into the ventricle 30 and partially opened so that the leaflets 42,44 can be captured. Referring now to FIG. 10, an actuation line 116 is extended to close one of the clasps 130, capturing a leaflet 42. FIG. 11 shows the other actuation line 116 being then extended to close the other clasp 130, capturing the remaining leaflet 44. Lastly, as can be seen in FIG. 12, the delivery sheath 102 and actuation wire 112 are then retracted and the device 100 is fully closed and deployed in the native mitral valve 400.

Figure 13:
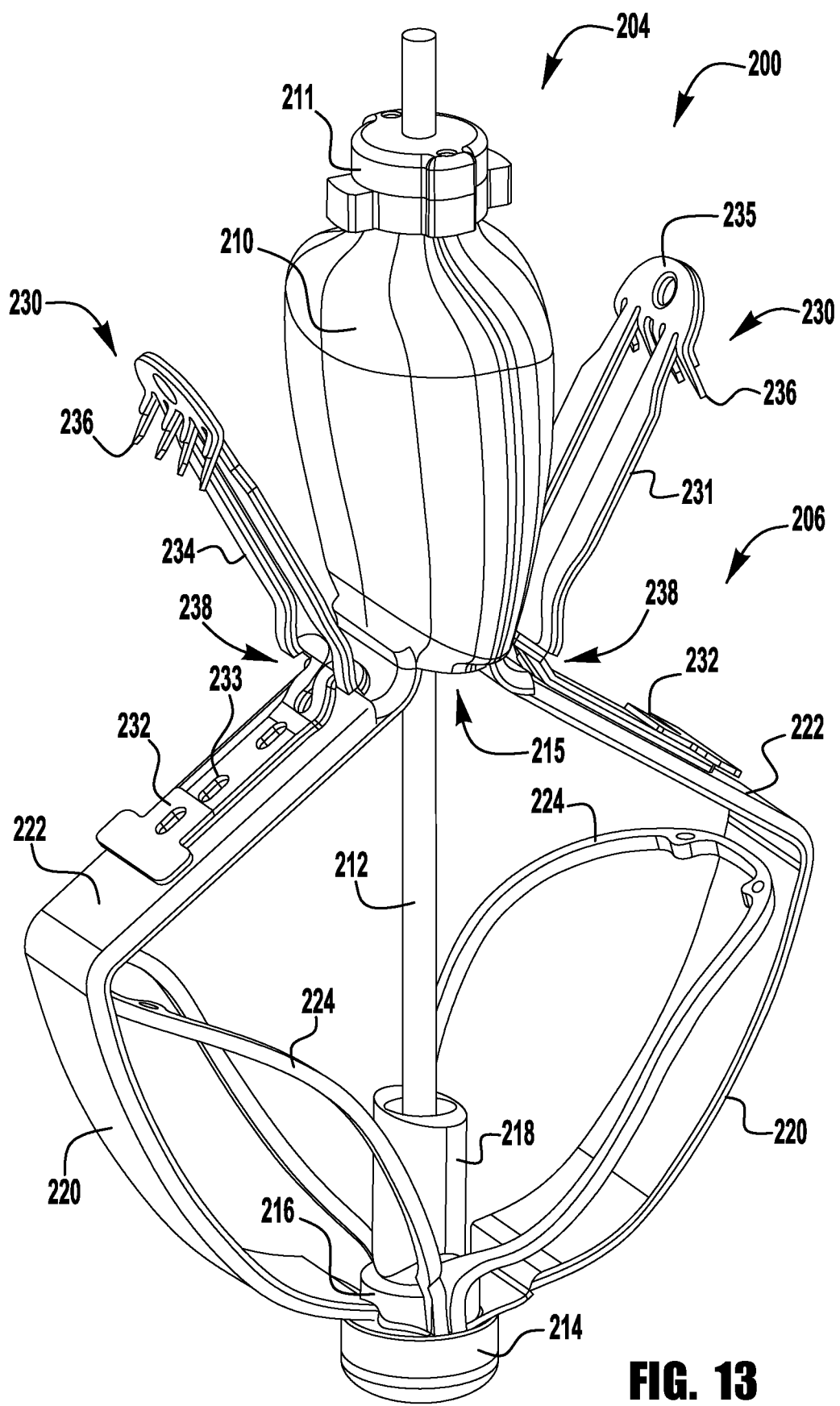
FIGS. 13-13A show another implantable prosthetic device according to a second embodiment.
Figure 13A:
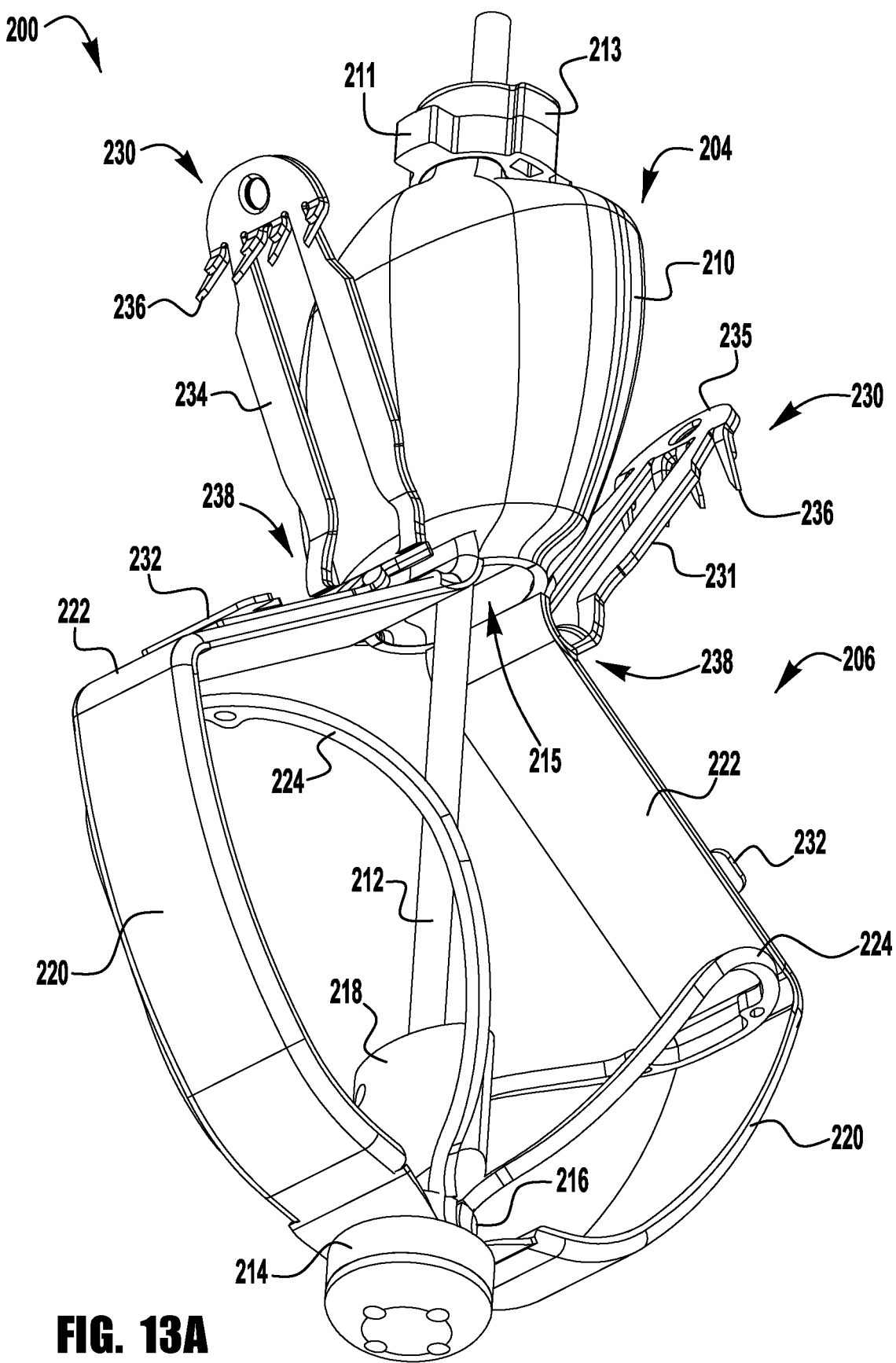

Referring now to FIG. 13, an implantable prosthetic device 200 is shown. The implantable device 200 is one of the many different configurations that the device 100 that is schematically illustrated in FIGS. 1-12 can take. The device 200 is deployed from a delivery sheath (not shown) and includes a coaption portion 204 and an anchor portion 206. The device 200 is loaded in the delivery sheath in the fully open position, because the fully open position takes up the least space and allows the smallest catheter to be used (or the largest device 200 to be used for a given catheter size). The coaption portion 204 of the device includes a coaption element 210 for implantation between the leaflets of the native mitral valve that is slideably attached to an actuation wire or shaft 212. Actuation of the actuation wire 212 opens and closes the anchor portion 206 of the device 200 to capture the mitral valve leaflets during implantation.

The anchor portion 206 of the device 200 includes outer paddles 220 and inner paddles 222 that are hingeably connected to the cap 214 and the coaption element 210. The actuation wire 212 extends through the delivery sheath (not shown), a collar 211, and the coaption element 210 to the cap 214 at the distal end of the anchor portion 206. Extending and retracting the actuation wire 212 increases and decreases the spacing between the coaption element 210 and the cap 214, respectively. The collar 211 optionally includes a collar seal 213 that forms a seal around the actuation wire or shaft 212 during implantation of the device 200, and that seals shut when the actuation wire 212 is removed to substantially close the device 200 to blood flow through the interior of the coaption element 210 after implantation. In some embodiments, the collar 2011 removably engages and attaches the coaption element 200 to the delivery sheath so that the coaption element 210 slides along the actuation wire 212 during actuation to open and close the paddles 220, 222 of the anchor portion 206. In some embodiments, the collar 2011 is held closed around the coaption element 2010 by the actuation wire 212, such that removal of the actuation wire 212 allows fingers (not shown) of the collar to open, releasing the coaption element 210. In some embodiments, the cap 2014 optionally includes a seal 216 and/or an insert 218 that fit inside an opening 215 of the coaption element 210, the coaption element 210 having a hollow interior. The seal 216 and/or insert 218 maintain the coaption element 210 substantially closed to blood flow when the actuation wire 212 is withdrawn and the device 200 is implanted.

The coaption element 210 and paddles 220, 222 are formed from a covering that may be a mesh, woven, braided, or formed in any other suitable way. The covering may be cloth, shape-memory alloy wire—such as Nitinol—to provide shape setting capability, or any other flexible material suitable for implantation in the human body. Paddle frames 224 provide additional pinching force between the outer paddles 222 and the coaption element 210, and assist in wrapping the leaflets around the sides of the coaption element 210 for a better seal between the coaption element 210 and the leaflets. In some embodiments, the covering extends around the paddle frames 224.

The barbed clasps 230 include a base or fixed arm 232, a moveable arm 234, barbs 236, and a hinge portion 238. The fixed arms 232 are attached to the inner paddles 222, with the hinge portion 238 disposed proximate the coaption element 210. The fixed arms 232 are attached to the inner paddles 222 through holes or slots 233 with sutures (not shown). The fixed arms 232 may be attached to the inner paddles 222 with any suitable means, such as screws or other fasteners, crimped sleeves, mechanical latches or snaps, welding, adhesive, or the like. The fixed arms 232 remain stationary relative to the inner paddles 222 when the moveable arms 234 are opened to open the barbed clasps 230 and expose the barbs 236. The barbed clasps 230 are opened by applying tension to actuation lines (not shown) attached to holes 235 disposed at ends of the moveable arms 234, thereby causing the moveable arms 234 to pivot on the hinge portions 238.

During implantation, the paddles 220, 222 are opened and closed to capture the native mitral valve leaflets between the paddles 220, 222 and the coaption element 210. The barbed clasps 230 further secure the native leaflets by engaging the leaflets with barbs 236 and pinching the leaflets between the moveable and fixed arms 234, 232. The barbs 236 of the barbed clasps 230 increase friction with the leaflets or may partially or completely puncture the leaflets. The actuation lines can be actuated independently so that each barbed clasp 230 can be opened and closed independently. Independent operation allows one leaflet to be captured at a time, or for the repositioning of a clasp 230 on a leaflet that was insufficiently captured, without altering a successful grasp on the other leaflet. The barbed clasps 230 not only open and close independent from each other but can be fully opened and closed independent from the position of the inner paddle 222, thereby allowing leaflets to be captured in a variety of positions as the particular situation requires.

Referring now to FIGS. 14-25, an implantable device 300 is shown being delivered and implanted within the native mitral valve 40 of the heart 10. The device 300 is similar to implantable device 200 of FIG. 13, though device 300 has a covering over the coaption element 310, clasps 330, inner paddles 322 and/or the outer paddles 320. The device 300 is deployed from a delivery sheath 302 and includes a coaption portion 304 and an anchor portion 306. The coaption portion 304 of the device includes a coaption element 310 for implantation between the leaflets of the native mitral valve that is slideably attached to an actuation wire or shaft 312. Actuation of the actuation wire or shaft 312 opens and closes the anchor portion 306 of the device 300 to capture the mitral valve leaflets during implantation.

The anchor portion 306 of the device 300 includes outer paddles 320 and inner paddles 322 that are flexibly connected to the cap 314 and the coaption element 310. The actuation wire 312 extends through a collar 303 (see FIG. 20), delivery sheath 302, and the coaption element 310 to the cap 314 at the distal end of the anchor portion 306. Extending and retracting the actuation wire 312 increases and decreases the spacing between the coaption element 310 and the cap 314, respectively. Fingers of the collar 303 removably attach the coaption element 310 to the delivery sheath 302 so that the coaption element 310 slides along the actuation wire 312 during actuation to open and close the paddles 320, 322 of the anchor portion 306. In some embodiments, the collar 303 is held closed around the coaption element 310 by the actuation wire 312, such that removal of the actuation wire 312 allows the fingers of the collar 303 to open, releasing the coaption element 310.

The coaption element 310 and paddles 320, 322 are formed from a flexible material that may be a mesh, woven, braided, or formed in any other suitable way. The flexible material may be cloth, shape-memory alloy wire—such as Nitinol—to provide shape setting capability, or any other flexible material suitable for implantation in the human body.

The barbed clasps 330 include a base or fixed arm 332, a moveable arm 334, barbs 336 (see FIG. 20), and a hinge portion 338. The fixed arms 332 are attached to the inner paddles 322, with the hinge portion 338 disposed proximate the coaption element 310. Sutures (not shown) attach the fixed arms 332 to the inner paddles 322. The fixed arms 332 may be attached to the inner paddles 322 with any suitable means, such as screws or other fasteners, crimped sleeves, mechanical latches or snaps, welding, adhesive, or the like. The fixed arms 332 remain stationary when the moveable arms 334 are opened to open the barbed clasps 330 and expose the barbs 336. The barbed clasps 330 are opened by applying tension to actuation lines 316 attached to the ends of the moveable arms 334, thereby causing the moveable arms 334 to pivot on the hinge portions 338.

During implantation, the paddles 320, 322 are opened and closed to capture the native mitral valve leaflets between the paddles 320, 322 and the coaption element 310. The outer paddles 320 have a wide curved shape that fits around the curved shape of the coaption element 310 to more securely grip the leaflets. The curved shape and rounded edges of the outer paddle 320 also prohibits tearing of the leaflet tissue. The barbed clasps 330 further secure the native leaflets by engaging the leaflets with barbs 336 and pinching the leaflets between the moveable and fixed arms 334, 332. The barbs 336 of the barbed clasps 330 increase friction with the leaflets or may partially or completely puncture the leaflets. The actuation lines can be actuated independently so that each barbed clasp 330 can be opened and closed independently. Independent operation allows one leaflet to be captured at a time, or for the repositioning of a clasp 330 on a leaflet that was insufficiently captured, without altering a successful grasp on the other leaflet. The barbed clasps 330 not only open and close independent from each other but can be fully opened and closed independent from the position of the inner paddle 322, thereby allowing leaflets to be captured in a variety of positions as the particular situation requires.

Figure 14:
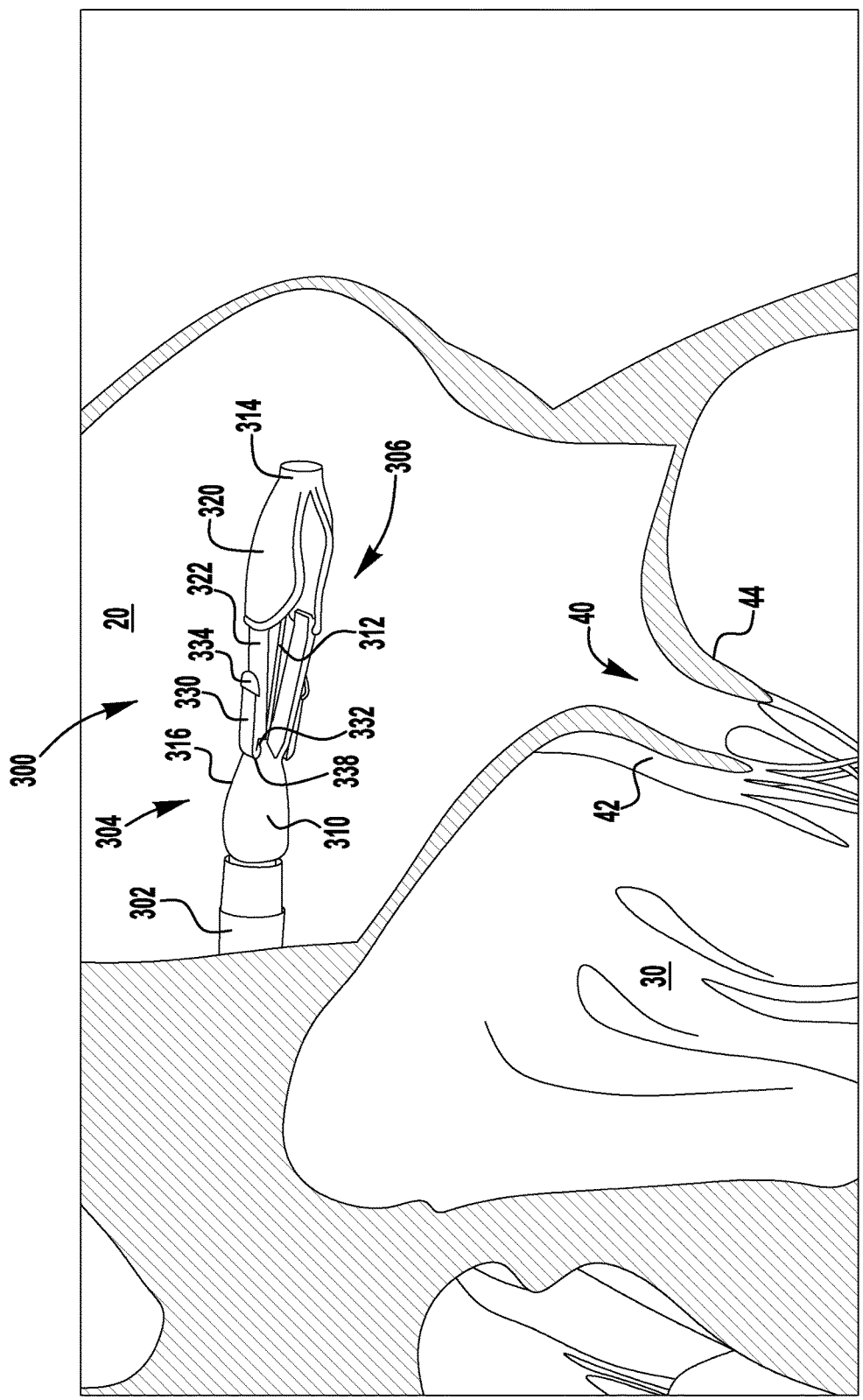
FIGS. 14-25 show another implantable prosthetic device according to a third embodiment being delivered and implanted within the native mitral valve.
Figure 15:
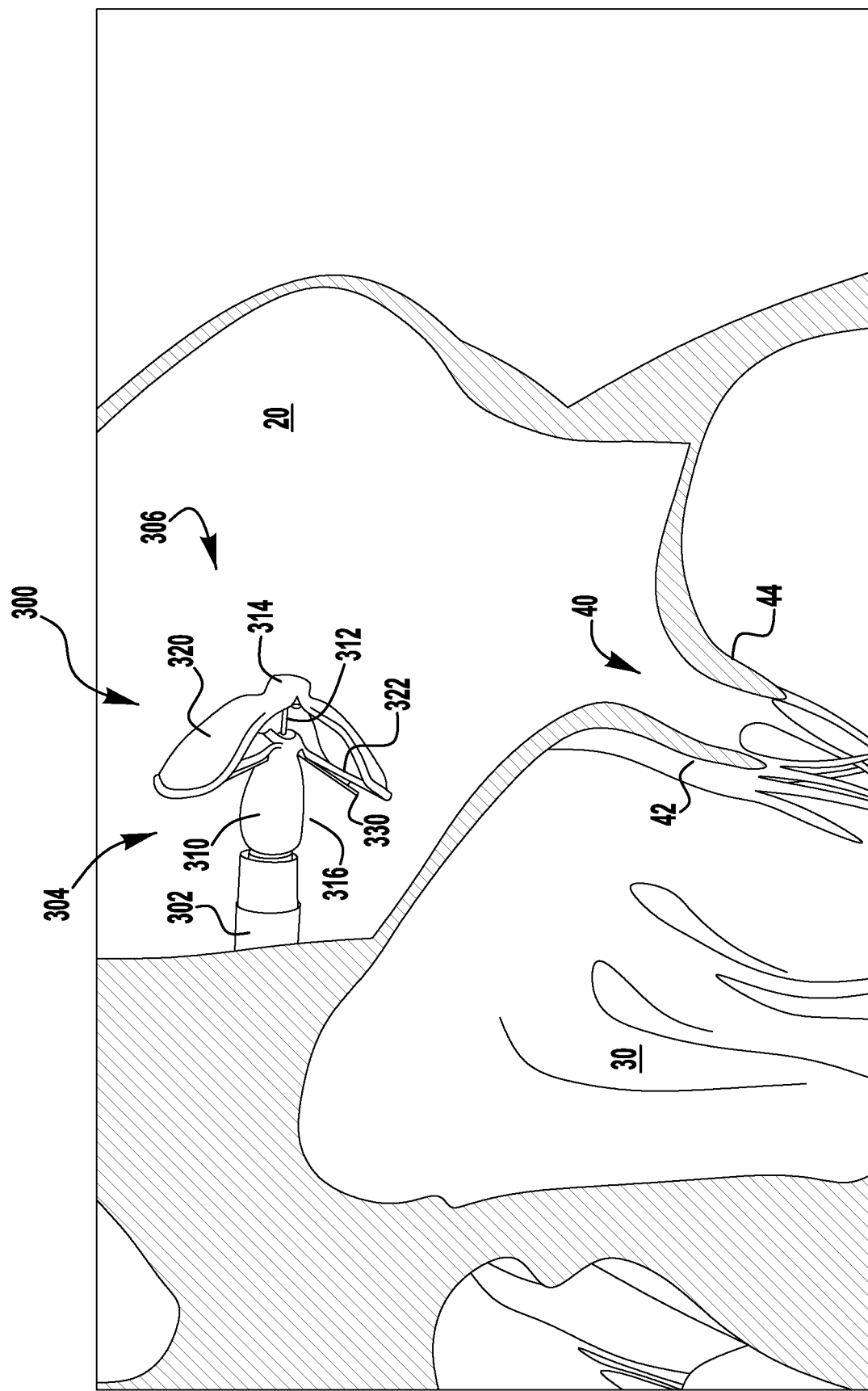
Figure 16:
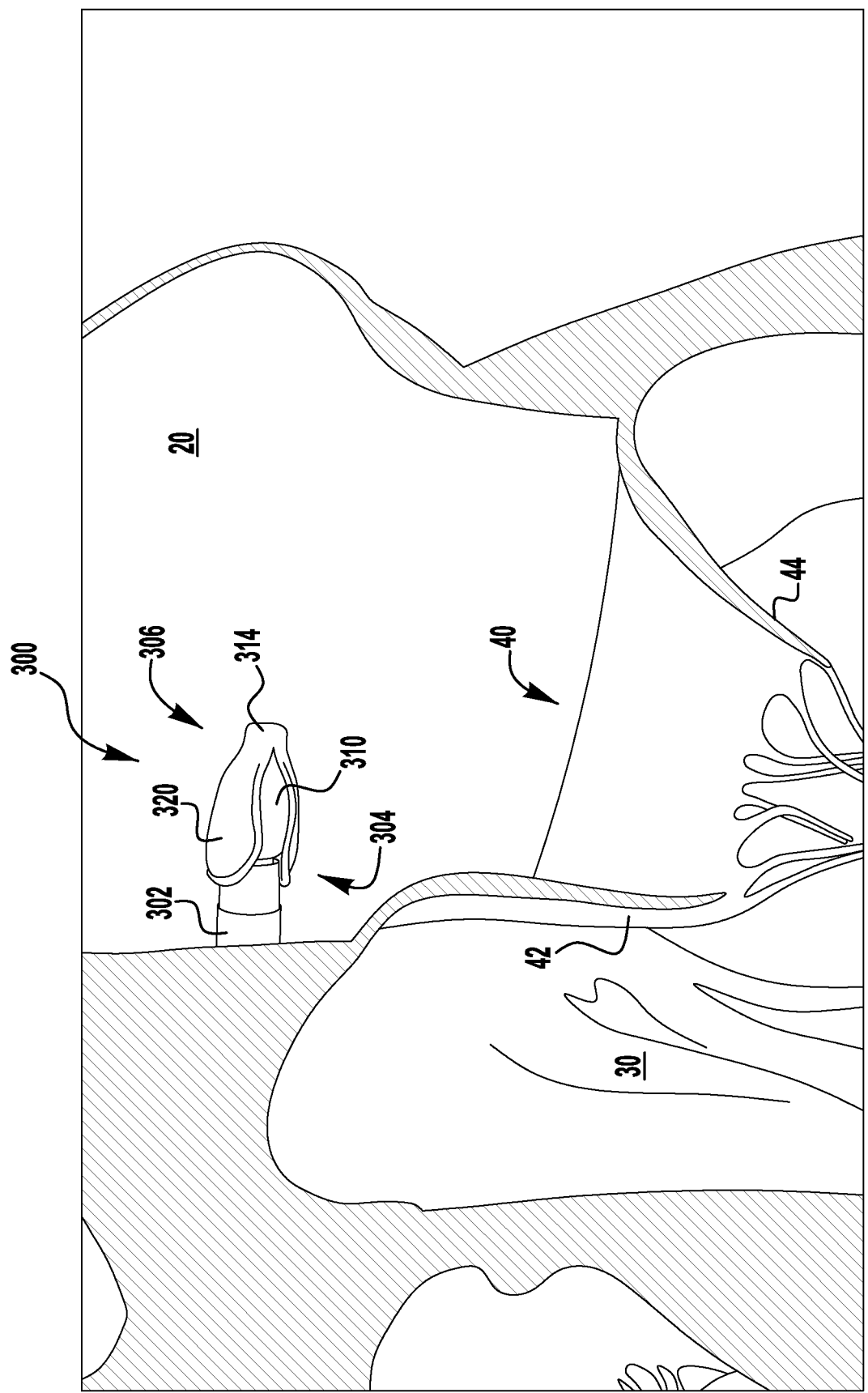
Figure 17:
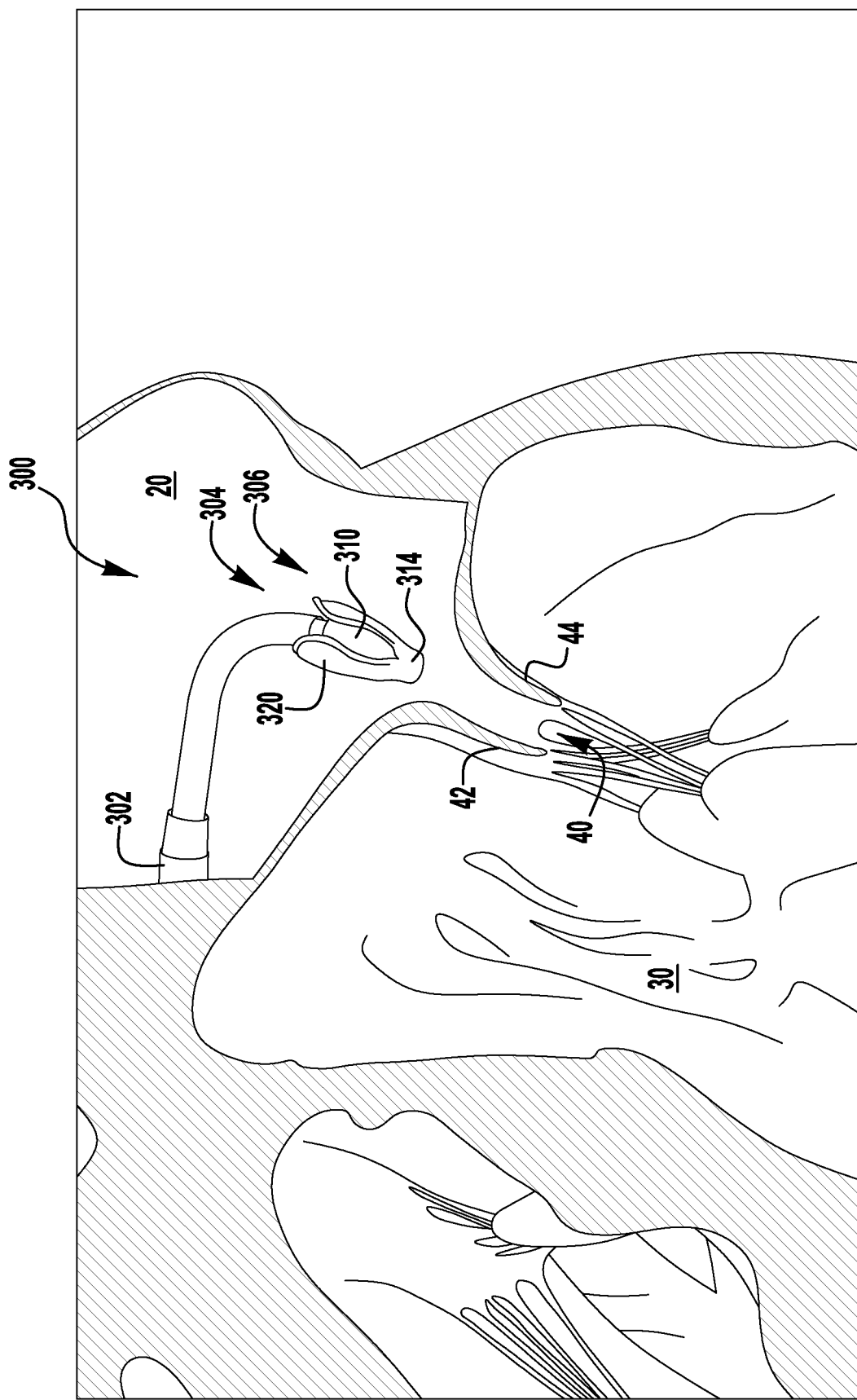
Figure 18:
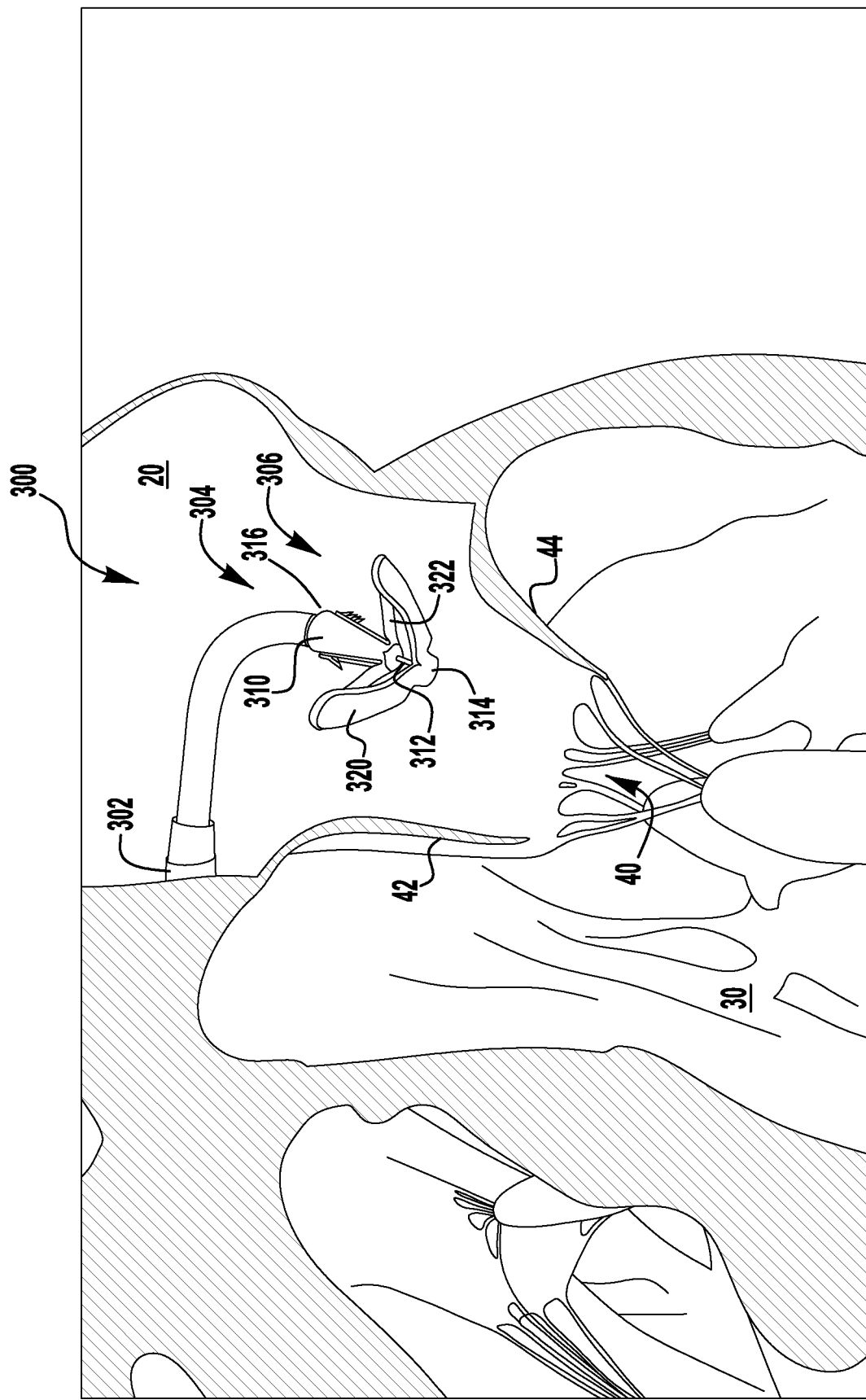
Figure 19:
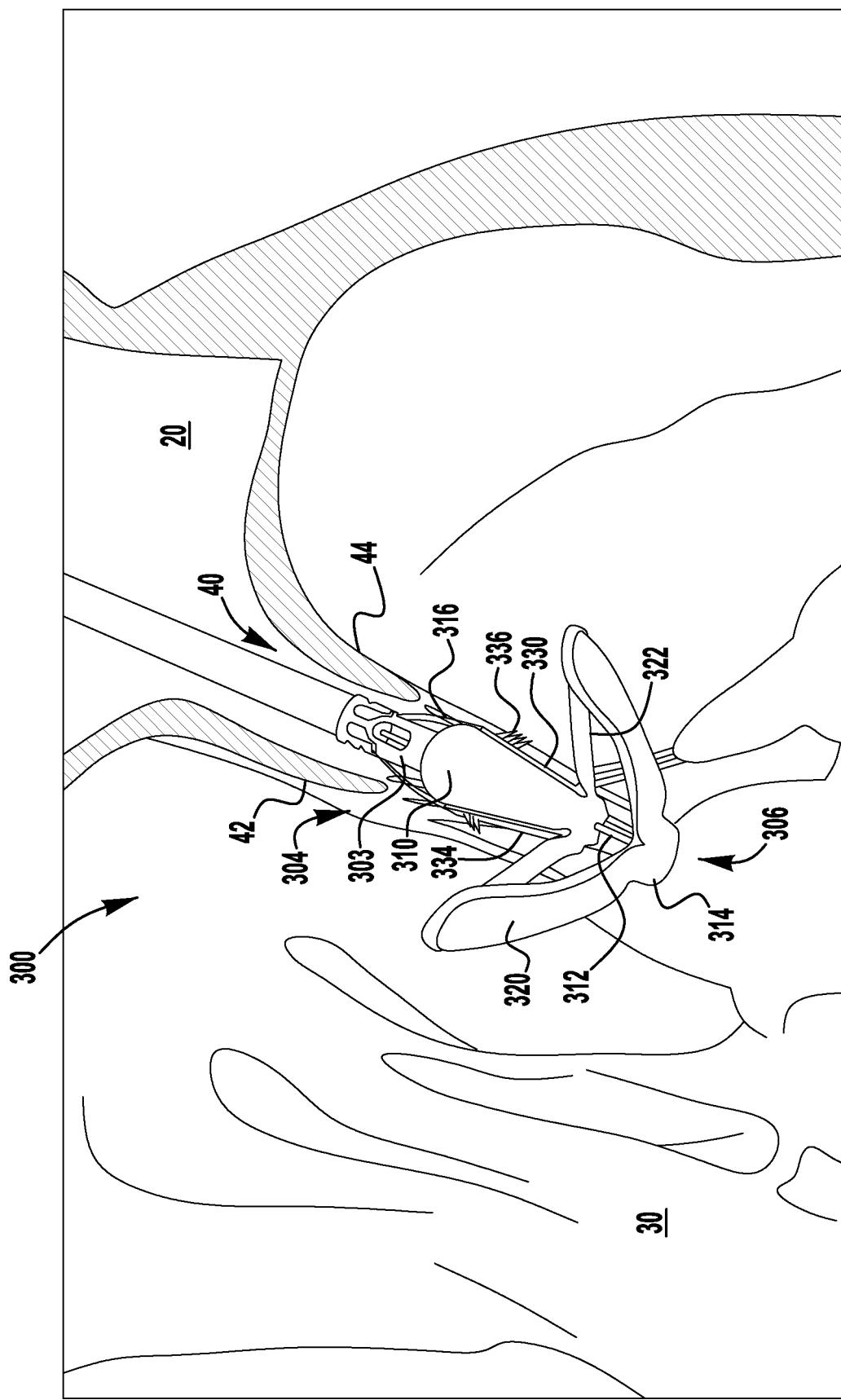
Figure 20:
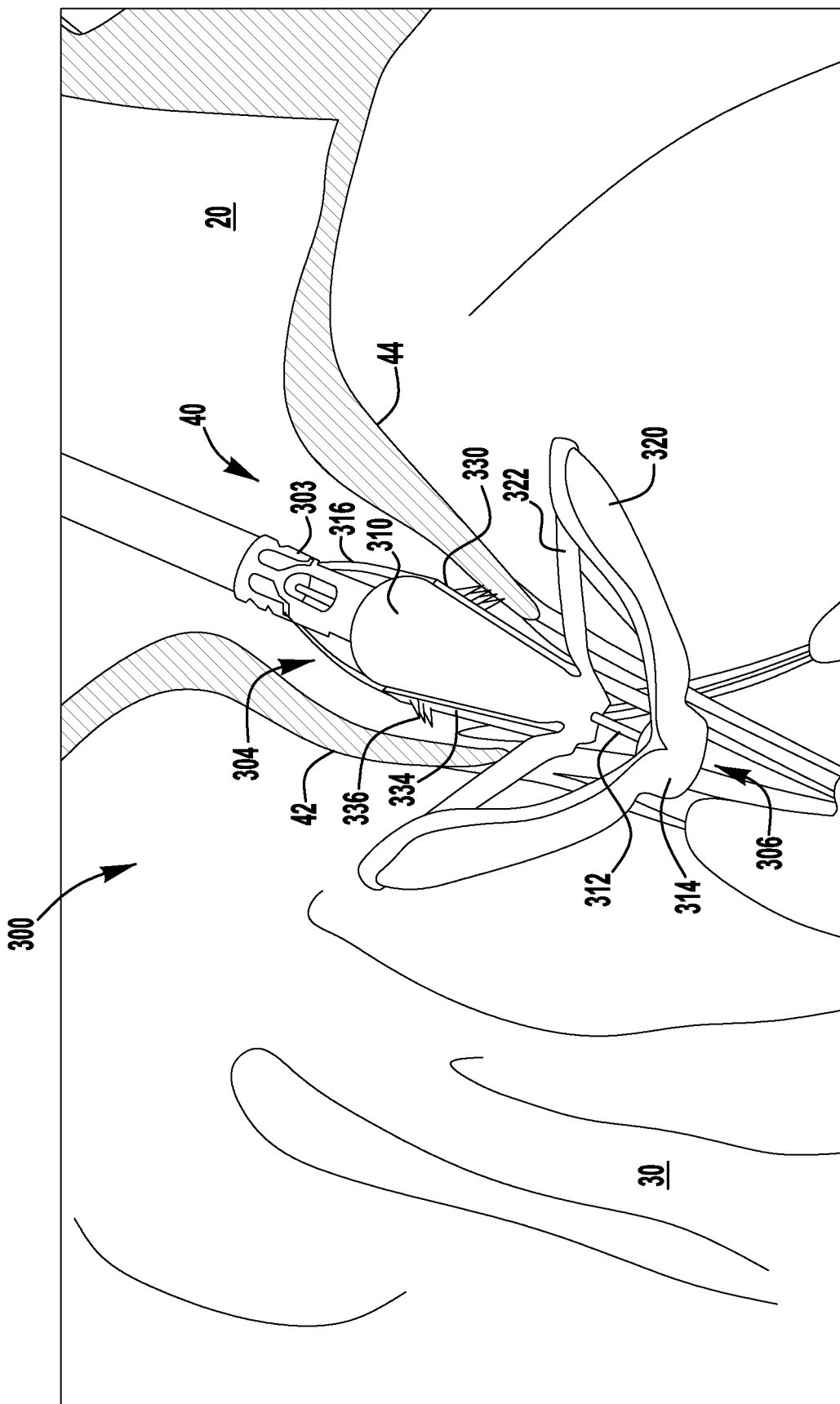
Figure 21:
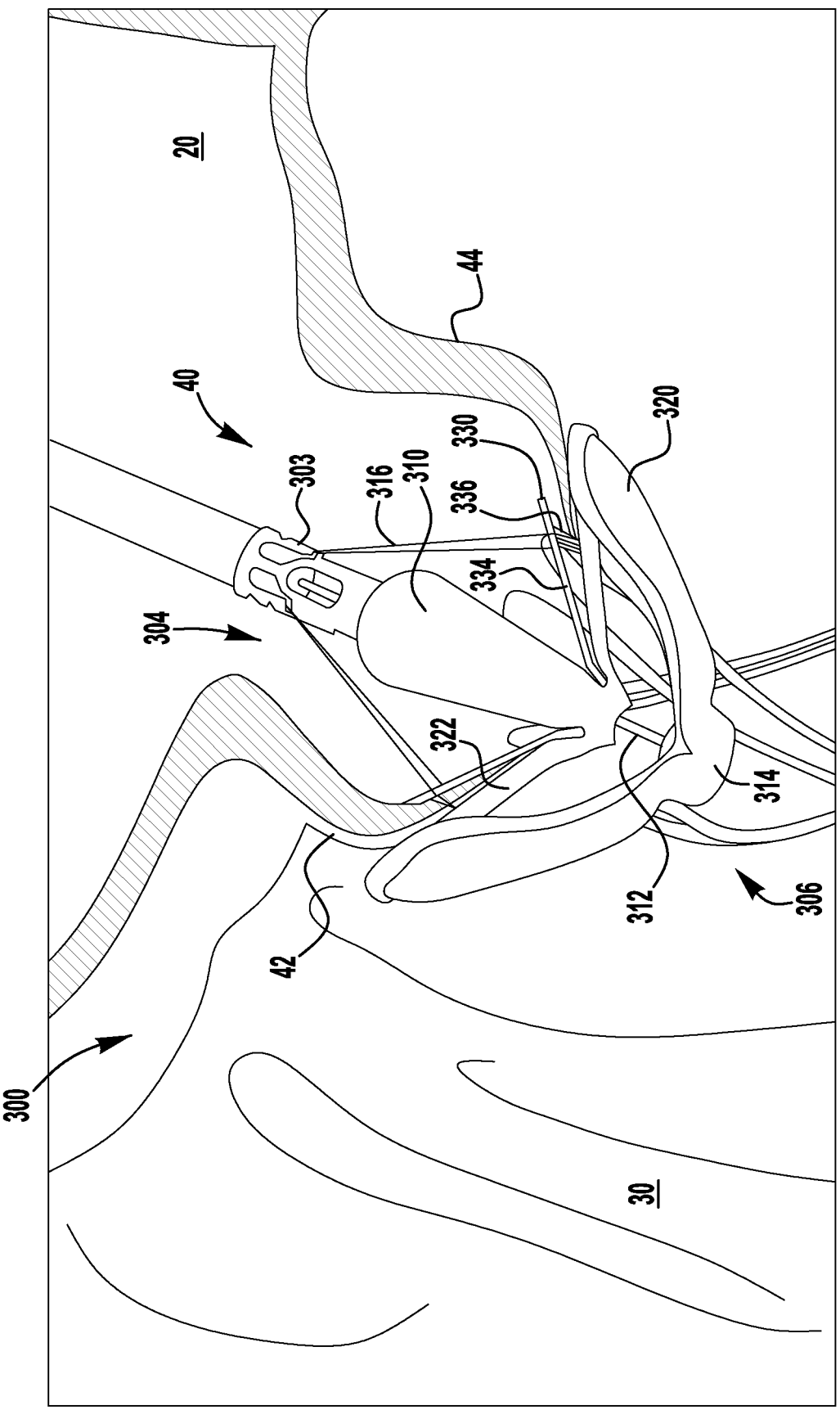
Figure 22:
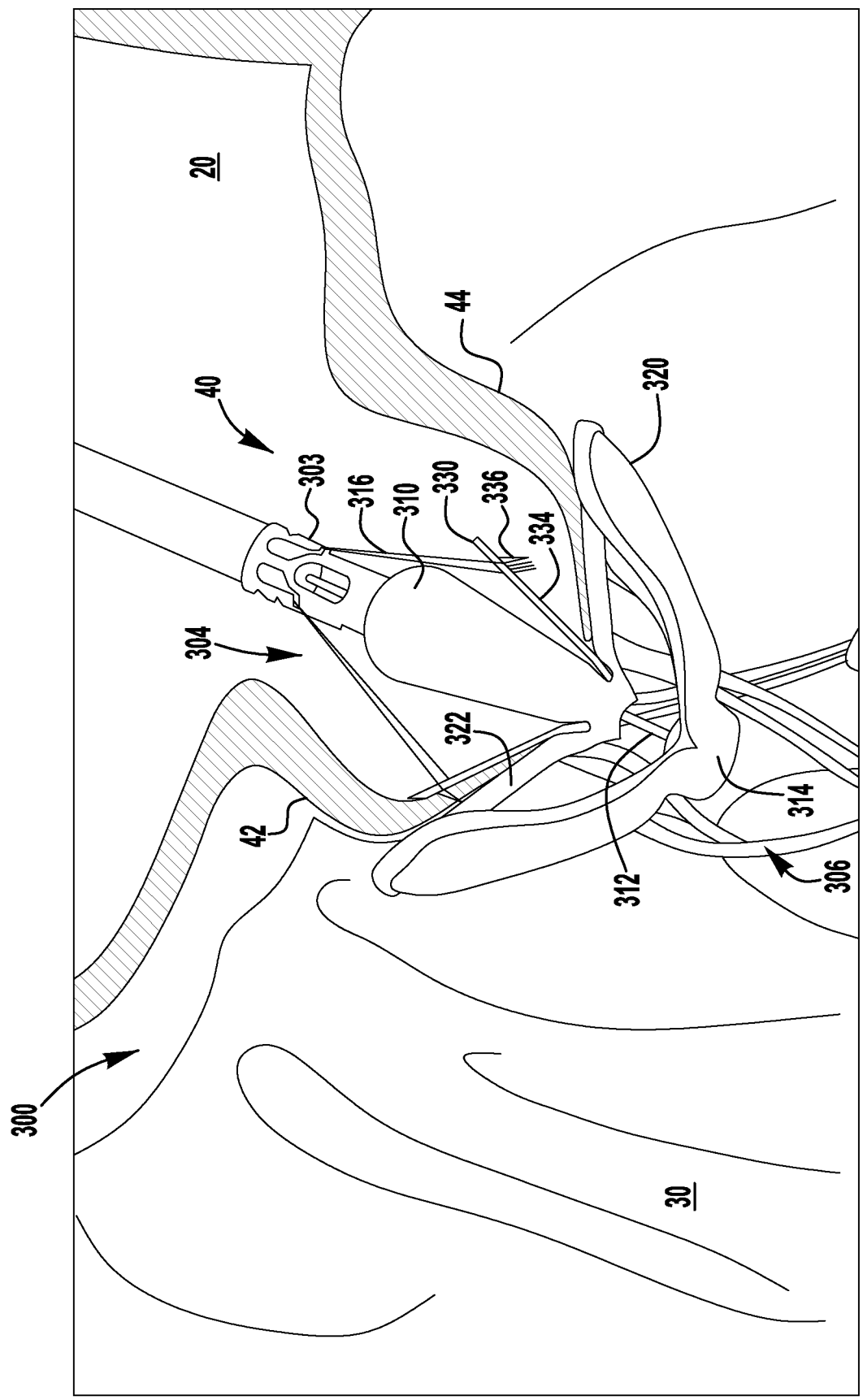
Figure 23:
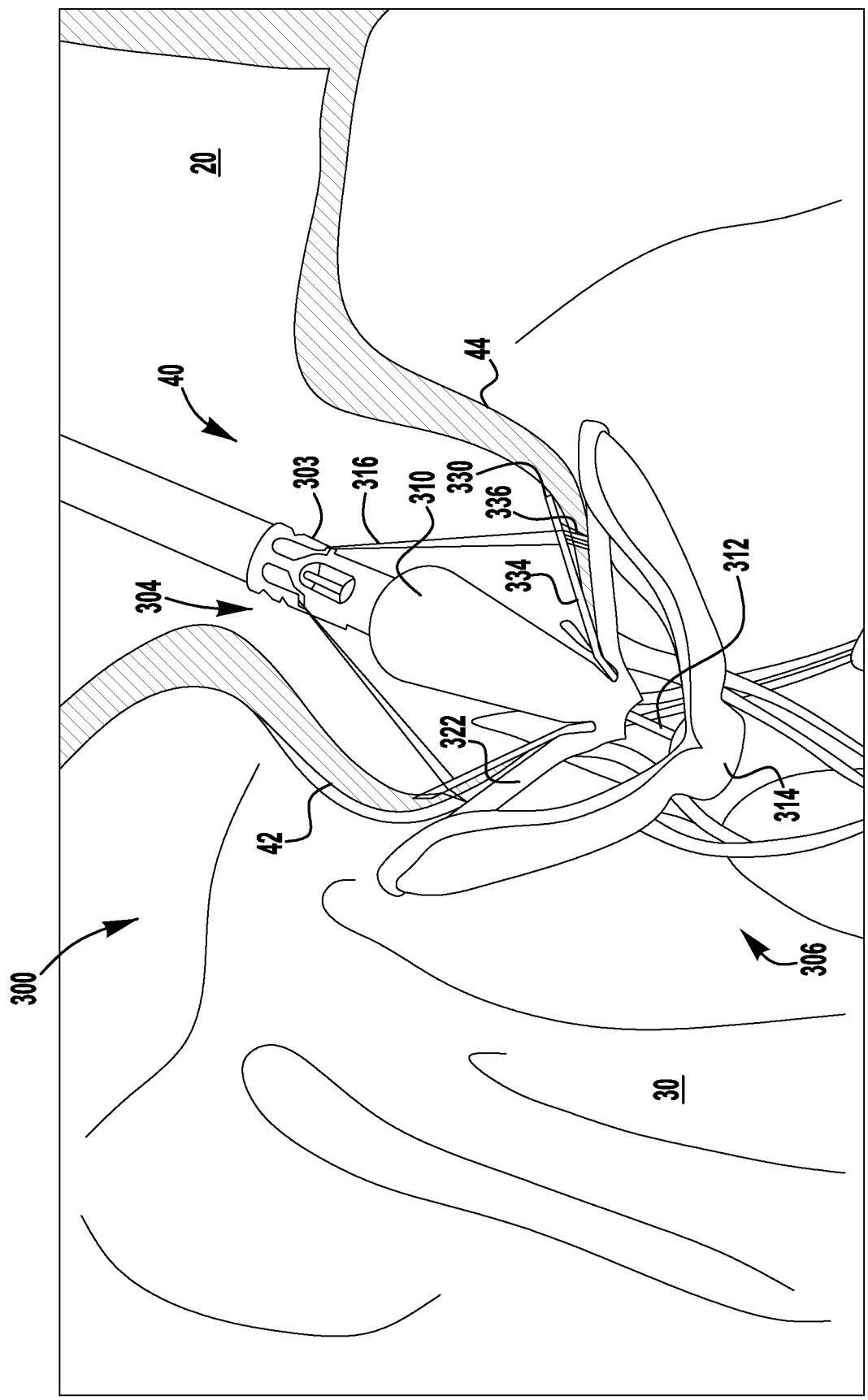
Figure 24:
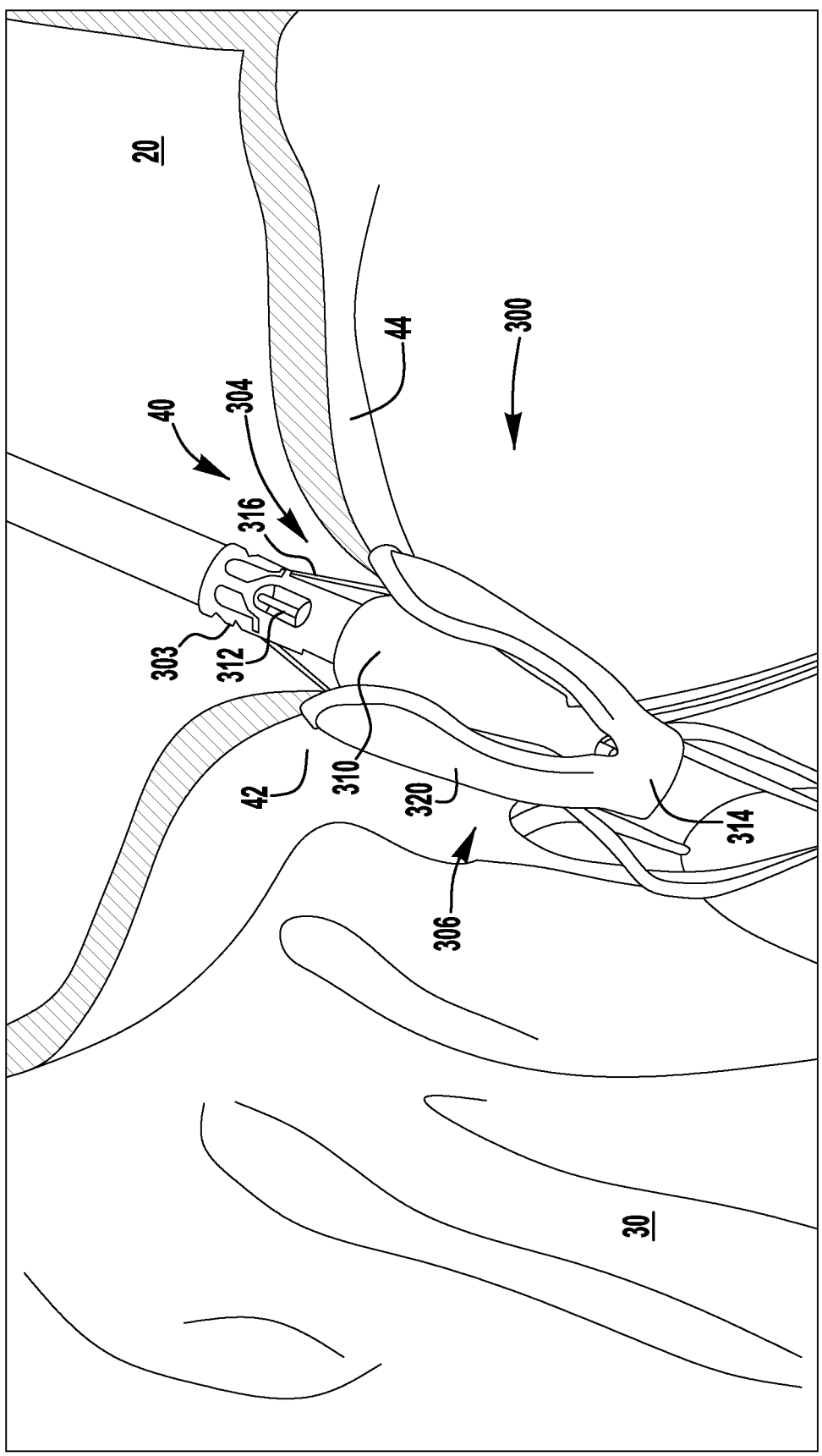
Figure 25:
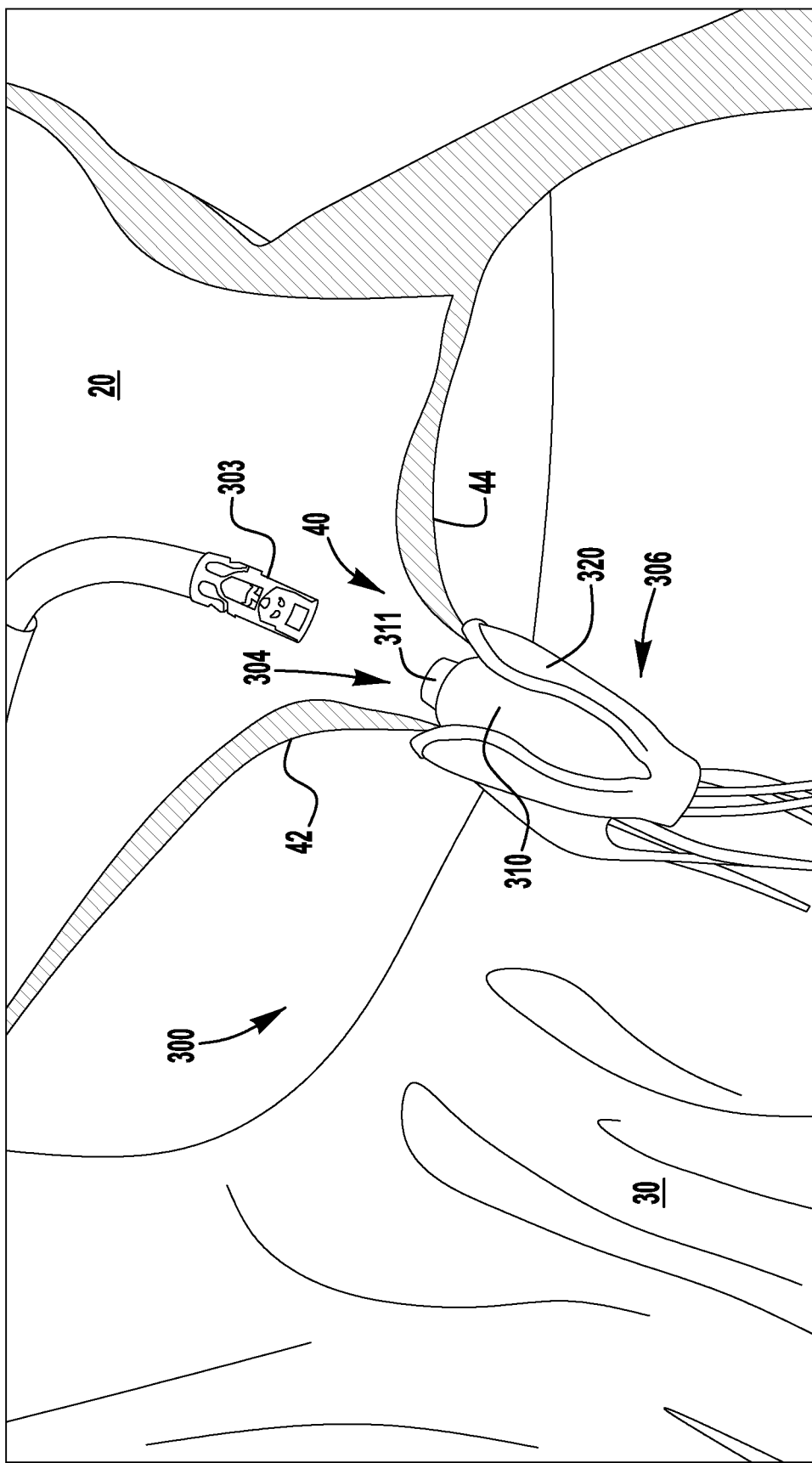

The device 300 is loaded in the delivery sheath in the fully open position, because the fully open position takes up the least space and allows the smallest catheter to be used (or the largest device 300 to be used for a given catheter size). Referring now to FIG. 14, the delivery sheath is inserted into the left atrium 20 through the septum and the device 300 is deployed from the delivery sheath 302 in the fully open condition. The actuation wire 312 is then retracted to move the device 300 into the fully closed condition shown in FIGS. 15-16 and then maneuvered towards the mitral valve 40 as shown in FIG. 17. Referring now to FIG. 18, when the device 300 is aligned with the mitral valve 40, the actuation wire 312 is extended to open the paddles 320, 322 into the partially opened position and the actuation lines 316 are retracted to open the barbed clasps 330 to prepare for leaflet capture. Next, as shown in FIGS. 19-20, the partially open device 300 is inserted through the mitral valve 40 until leaflets are properly positioned in between the inner paddles 322 and the coaption element 310 and inside the open barbed clasps 330. FIG. 21 shows the device 300 with both clasps 330 closed, though the barbs 336 of one clasp 330 missed one of the leaflets 44. As can be seen in FIGS. 22-23, the out of position clasp 330 is opened and closed again to properly capture the missed leaflet 44. When both leaflets 42, 44 are captured properly, the actuation wire 312 is retracted to move the device 300 into the fully closed position shown in FIG. 24. With the device 300 fully implanted in the native mitral valve 40, the actuation wire 312 is withdrawn to release the collar 303 from an upper end or plate 311 of the coaption element 310. Once deployed, the device 300 may be maintained in the fully closed position with a mechanical means such as a latch or may be biased to remain closed through the use of spring material, such as steel, and/or shape-memory alloys such as Nitinol. For example, the paddles 320, 322 may be formed of steel or Nitinol shape-memory alloy—produced in a wire, sheet, tubing, or laser sintered powder—and are biased to hold the outer paddles 320 closed around the coaption element 310 and the barbed clasps 330 pinched around native leaflets.

Referring now to FIG. 23A, a close-up view of one of the leaflets 42, 44 captured by one of the clasps 330 is shown. The leaflet 42, 44 is captured between the moveable and fixed arms 334, 332 of the clasp 330. As shown in FIG. 23A, the tissue of the leaflet 42, 44 is not pierced by the barbs 336, though in some embodiments the barbs 336 may partially or fully pierce through the leaflet 42, 44. The angle and height of the barbs 336 relative to the moveable arm 334 helps to secure the leaflet 42, 44 within the clasp 330. In particular, a force pulling the implant off of the native leaflet will encourage the barbs 336 to further engage the tissue, thereby ensuring better retention. Retention of the leaflet 42, 44 in the clasp 330 is further improved by the position of fixed arm 332 near the barbs 336 when the clasp 330 is closed. In this arrangement, the tissue is formed by the fixed and moveable arms 332, 334 and the barbs 336 into an S-shaped torturous path. Thus, forces pulling the leaflet away from the clasp 330 will encourage the tissue to further engage the barbs 336 before the leaflets can escape Referring now to FIG. 26, an exemplary barbed clasp 400 for use in implantable prosthetic devices, such as devices 100, 200, 300 described above, is shown. The barbed clasp 400 is formed from a top layer 402 and a bottom layer 404. The two-layer design of the clasp 400 allow thinner sheets of material to be used, thereby improving the flexibility of the clasp 400 over a clasp formed from a single thicker sheet, while maintaining the strength of the clasp 400 needed to successfully retain a native valve leaflet.

The barbed clasp 400 includes a fixed arm 410, a hinged portion 420, and a movable arm 430 having a barbed portion 440. The top and bottom layers 402, 404 have a similar shape and in certain embodiments are attached to each other at the barbed end 440. The hinged portion 420 is spring-loaded so that the fixed and moveable arms 410, 430 are biased toward each other when the barbed clasp 400 is in a closed condition. When assembled to an implantable prosthetic device, the fixed arm 410 is attached to a portion of the prosthetic device. The clasp 400 is opened by pulling on an actuation line attached to the moveable arm 430 until the spring force of the hinge portion 420 is overcome.

The fixed arm 410 is formed from a tongue 411 of material extending from the hinged portion 420 between two side beams 431 of the moveable arm 430. The tongue 411 is biased between the side beams 431 by the hinge portion 420 such that force must be applied to move the tongue 411 from a neutral position located beyond the side beams 431 to a preloaded position substantially parallel with the side beams 431. The tongue 411 is held in the preloaded position by a T-shaped cross-bar 414 that is attached to the tongue 411 and extends outward to engage the side beams 431. In certain embodiments, the angle between the fixed and moveable arms 410, 430 when the tongue is in the neutral position is about 30 to about 100 degrees, 30 to about 90 degrees, or about 30 to about 60 degrees, or about 40 to about 50 degrees, or about 45 degrees.

The tongue 411 includes holes 412 for receiving sutures (not shown) that attach the fixed arm 410 to an implantable device. The fixed arm 410 may be attached to an implantable device by various attaching means, such as screws or other fasteners, crimped sleeves, mechanical latches or snaps, welding, adhesive, or the like. In certain embodiments, the holes 412 are elongated slots or oval-shaped holes to accommodate sliding of the layers 402, 404 without damaging the sutures attaching the clasp 400 to an implantable device.

The hinge portion 420 is formed by two beam loops 422 that extend from the tongue 411 of the fixed arm 410 to the side beams 431 of the moveable arm 430. In certain embodiments, the beam loops 422 are narrower than the tongue 411 and side beam 431 to provide additional flexibility. The beam loops 422 each include a center portion 424 extending from the tongue 411 and an outer portion 426 extending to the side beams 431. The beam loops 422 are bent into a somewhat spiral or helical shape by bending the center and outer portions 424, 426 in opposite directions, thereby forming an offset or step distance 428 between the tongue 411 and side beams 431. The step distance 428 provides space between the arms 410, 430 to accommodate the native leaflet of the mitral valve after it is captured. In certain embodiments, the step distance 428 is about 0.5 millimeter to about 1 millimeters, or about 0.75 millimeters.

When viewed in a top plan view, the beam loops have an "omega-like" shape. This shape of the beam loops 422 allows the fixed and moveable arms 410, 430 to move considerably relative to each other without plastically deforming the clasp material. For example, in certain embodiments, the tongue 411 can be pivoted from a neutral position that is approximately 45 degrees beyond the moveable arm 430 to a fully open position that ranges from about 140 degrees to about 200 degrees, to about 170 degrees to about 190 degrees, or about 180 degrees from the moveable arm 430 without plastically deforming the clasp material. In certain embodiments, the clasp material plastically deforms during opening without reducing or without substantially reducing the pinch force exerted between the fixed and moveable arms in the closed position.

Preloading the tongue 411 enables the clasp 400 to maintain a pinching or clipping force on the native leaflet when closed while also being able to be opened wide to more easily capture the native leaflet. The p reloading of the tongue 411 provides a significant advantage over prior art clips that provide little or no pinching force when closed. Additionally, closing the clasp 400 with spring force is a significant improvement over clips that use a one-time locking closure mechanism, as the clasp 400 can be repeatedly opened and closed for repositioning on the leaflet while still maintaining sufficient pinching force when closed.

The barbed portion 440 of the moveable arm 430 includes an eyelet 442, barbs 444, and barb supports 446. Positioning the barbed portion of the clasp 400 at an end of the moveable arm 430 increases the space between the barbs 444 and the fixed arm 410 when the clasp 400 is opened, thereby improving the ability of the clasp 400 to successfully capture a leaflet during implantation. This distance also allows the barbs 444 to more reliably disengage from the leaflet for repositioning. In certain embodiments, the barbs of the clasps may be staggered longitudinally to further distribute pinch forces and local leaflet stress.

The barbs 444 are laterally spaced apart at the same distance from the hinge portion 420, providing a superior distribution of pinching forces on the leaflet tissue while also making the clasp more robust to leaflet capture than barbs arranged in a longitudinal row. In some embodiments, the barbs 444 can be staggered to further distribute pinch forces and local leaflet stress.

The barbs 444 are formed from the bottom layer 404 and the barb supports 446 are formed from the top layer. In certain embodiments, the barbs are formed from the top layer 402 and the barb supports are formed from the bottom layer 404. Forming the barbs 444 only in one of the two layers 402, 404 allows the barbs to be thinner and therefore effectively sharper than a barb formed from the same material that is twice as thick. The barb supports 446 extend along a lower portion of the barbs 444 to stiffen the barbs 444, further improving penetration and retention of the leaflet tissue. In certain embodiments, the ends of the barbs 444 are further sharpened using any suitable sharpening means.

The barbs 444 are angled away from the moveable arm 430 such that they easily penetrate tissue of the native leaflets with minimal pinching or clipping force. The barbs 444 extend from the moveable arm at an angle of about 45 degrees to about 75 degrees, or about 45 degrees to about 60 degrees, or about 48 to about 56 degrees, or about 52 degrees. The angle of the barbs 444 provides further benefits, in that force pulling the implant off of the native leaflet will encourage the barbs 444 to further engage the tissue, thereby ensuring better retention. Retention of the leaflet in the clasp 400 is further improved by the position of the T-shaped cross bar 414 near the barbs 444 when the clasp 400 is closed. In this arrangement, the tissue pierced by the barbs 444 is pinched against the moveable arm 430 at the cross bar 414 location, thereby forming the tissue into an S-shaped torturous path as it passes over the barbs 444. Thus, forces pulling the leaflet away from the clasp 400 will encourage the tissue to further engage the barbs 444 before the leaflets can escape.

Each layer 402, 404 of the clasp 400 is laser cut from a sheet of shape-memory alloy, such as Nitinol. The top layer 402 is aligned and attached to the bottom layer 404. In certain embodiments, the layers 402, 404 are attached at the barbed end 440 of the moveable arm 430. For example, the layers 402, 404 may be attached only at the barbed end 440, to allow the remainder of the layers to slide relative to one another. Portions of the combined layers 402, 404, such as a fixed arm 410, barbs 444 and barb supports 446, and beam loops 422 are bent into a desired position. The layers 402, 404 may be bent and shapeset together or may be bent and shapeset separately and then joined together. The clasp 400 is then subjected to a shape-setting process so that internal forces of the material will tend to return to the set shape after being subjected to deformation by external forces. After shape setting, the tongue 411 is moved to its preloaded position so that the cross-bar 414 can be attached. Consequently, the clasp 400 can be completely flattened for delivery through a delivery sheath and allowed to expand once deployed within the heart.

The clasp 400 is opened and closed by applying and releasing tension on an actuation means such as an actuation line, suture, wire, rod, catheter, or the like (not shown) attached to the moveable arm 430. The suture is inserted through an eyelet 442 near the barbed portion 440 of the moveable arm 430 and wraps around the end of the moveable arm 430 before returning to the delivery sheath. In certain embodiments, an intermediate suture loop is made through the eyelet and the suture is inserted through the intermediate loop. An intermediate loop of suture material reduces friction experienced by the actuation suture relative to the friction between the actuation suture and the clasp material. When the suture is looped through the eyelet 442 or intermediate loop, both ends of the actuation suture extend back into and through the delivery sheath 102 (see FIG. 1). The suture can be removed by pulling one end of the suture proximally until the other end of the suture pulls through the eyelet or intermediate loop and back into the delivery sheath.

Referring now to FIG. 27, an exemplary barbed clasp 500 for use in implantable prosthetic devices, such as devices 100, 200, 300 described above, is shown. The barbed clasp 500 is substantially the same as the barbed clasp 400, except the barbed clasp 500 includes a suture pin 543 disposed across an opening 542, instead of the hole 442. The barbed clasp 500 is formed from a top layer 502 and a bottom layer 504. The two-layer design of the clasp 500 allow thinner sheets of material to be used, thereby improving the flexibility of the clasp 500 over a clasp formed from a single thicker sheet, while maintaining the strength of the clasp 500 needed to successfully retain a native valve leaflet.

The barbed clasp 500 includes a fixed arm 510, a hinged portion 520, and a movable arm 530 having a barbed portion 540. The top and bottom layers 502, 504 have a similar shape and in certain embodiments are attached to each other at the barbed end 540. The hinged portion 520 is spring-loaded so that the fixed and moveable arms 510, 530 are biased toward each other when in the barbed clasp 500 is in a closed condition. When assembled to an implantable prosthetic device, the fixed arm 510 is attached to a portion of the prosthetic device. The clasp 500 is opened by pulling on an actuation means or actuation line attached to the moveable arm 530 until the spring force of the hinge portion 520 is overcome.

The fixed arm 510 is formed from a tongue 511 of material extending from the hinged portion 520 between two side beams 531 of the moveable arm 530. The tongue 511 is biased between the side beams 531 by the hinge portion 520 such that force must be applied to move the tongue 511 from a neutral position located beyond the side beams 531 to a preloaded position substantially parallel with the side beams 531. The tongue 511 is held in the preloaded position by a T-shaped cross-bar 514 that is attached to the tongue 511 and extends outward to engage the side beams 531. In certain embodiments, the angle between the fixed and moveable arms 510, 530 when the tongue is in the neutral position is about 30 to about 100 degrees, or about 30 to about 90 degrees, or about 30 to about 60 degrees, or about 40 to about 50 degrees, or about 45 degrees.

The tongue 511 includes holes 512 for receiving sutures (not shown) that attach the fixed arm 510 to an implantable device. The fixed arm 510 may be attached to an implantable device by various attaching means, such as screws or other fasteners, crimped sleeves, mechanical latches or snaps, welding, adhesive, or the like. In certain embodiments, the holes 512 are elongated slots or oval-shaped holes to accommodate sliding of the layers 502, 504 without damaging the sutures attaching the clasp 500 to an implantable device.

The hinge portion 520 is formed by two beam loops 522 that extend from the tongue 511 of the fixed arm 510 to the side beams 531 of the moveable arm 530. In certain embodiments, the beam loops 522 are narrower than the tongue 511 and side beam 531 to provide additional flexibility. The beam loops 522 each include a center portion 524 extending from the tongue 511 and an outer portion 526 extending to the side beams 531. The beam loops 522 are bent into a somewhat spiral or helical shape by bending the center and outer portions 524, 526 in opposite directions, thereby forming a step distance 528 between the tongue 511 and side beams 531. The step distance 528 provides space between the arms 510, 530 to accommodate the native leaflet of the mitral valve after it is captured. In certain embodiments, the step distance 528 is about 0.5 millimeter to about 1 millimeters, or about 0.75 millimeters.

When viewed in a top plan view, the beam loops have an "omega-like" shape. This shape of the beam loops 522 allows the fixed and moveable arms 510, 530 to move considerably relative to each other without plastically deforming the clasp material. For example, in certain embodiments, the tongue 511 can be pivoted from a neutral position that is approximately 45 degrees beyond the moveable arm 530 to a fully open position that ranges from about 140 degrees to about 200 degrees, to about 170 degrees to about 190 degrees, or about 180 degrees from the moveable arm 530 without plastically deforming the clasp material. In certain embodiments, the clasp material plastically deforms during opening without reducing the pinch force exerted between the fixed and moveable arms in the closed position.

Preloading the tongue 511 enables the clasp 500 to maintain a pinching or clipping force on the native leaflet when closed while also being able to be opened wide to more easily capture the native leaflet. The p reloading of the tongue 511 provides a significant advantage over prior art clips that provide little or no pinching force when closed. Additionally, closing the clasp 500 with spring force is a significant improvement over clips that use a one-time locking closure mechanism, as the clasp 500 can be repeatedly opened and closed for repositioning on the leaflet while still maintaining sufficient pinching force when closed.

The barbed portion 540 of the moveable arm 530 includes an eyelet 542, barbs 544, and barb supports 546. Positioning the barbed portion of the clasp 500 at an end of the moveable arm 530 increases the space between the barbs 544 and the fixed arm 510 when the clasp 500 is opened, thereby improving the ability of the clasp 500 to successfully capture a leaflet during implantation. This distance also allows the barbs 544 to more reliably disengage from the leaflet for repositioning. In certain embodiments, the barbs of the clasps may be staggered longitudinally to further distribute pinch forces and local leaflet stress.

The barbs 544 are laterally spaced apart at the same distance from the hinge portion 520, providing a superior distribution of pinching forces on the leaflet tissue while also making the clasp more robust to leaflet capture than barbs arranged in a longitudinal row.

The barbs 544 are formed from the bottom layer 504 and the barb supports 546 are formed from the top layer. Forming the barbs 544 only in one of the two layers 502, 504 allows the barbs to be thinner and therefore effectively sharper than a barb formed from the same material that is twice as thick. The barb supports 546 extend along a lower portion of the barbs 544 to stiffen the barbs 544, further improving penetration and retention of the leaflet tissue. In certain embodiments, the ends of the barbs 544 are further sharpened using any suitable sharpening means.

The barbs 544 are angled away from the moveable arm 530 such that they easily penetrate tissue of the native leaflets with minimal pinching or clipping force. The barbs 544 extend from the moveable arm at an angle of about 45 to about 75 degrees, or about 45 to about 60 degrees, or about 48 to about 56 degrees, or about 52 degrees. The angle of the barbs 544 provides further benefits, in that force pulling the implant off of the native leaflet will encourage the barbs 544 to further engage the tissue, thereby ensuring better retention. Retention of the leaflet in the clasp 500 is further improved by the position of the T-shaped cross bar 514 near the barbs 544 when the clasp 500 is closed. In this arrangement, the tissue pierced by the barbs 544 is pinched against the moveable arm 530 at the cross bar 514 location, thereby forming the tissue into an S-shaped torturous path as it passes over the barbs 544. Thus, forces pulling the leaflet away from the clasp 500 will encourage the tissue to further engage the barbs 544 before the leaflets can escape.

Each layer 502, 504 of the clasp 500 is laser cut from a sheet of shape-memory alloy, such as Nitinol. The top layer 502 is aligned and attached to the bottom layer 504. In certain embodiments, the layers 502, 504 are attached at the barbed end 540 of the moveable arm 530. For example, the layers 402, 404 may be attached only at the barbed end 440, to allow the remainder of the layers to slide relative to one another. Portions of the combined layers 502, 504, such as a fixed arm 510, barbs 544 and barb supports 546, and beam loops 522 are bent into a desired position. The clasp 500 is then subjected to a shape-setting process so that internal forces of the material will tend to return to the set shape after being subjected to deformation by external forces. After shape setting, the tongue 511 is moved to its preloaded position so that the cross-bar 514 can be attached. Consequently, the clasp 500 can be completely flattened for delivery through a delivery sheath and allowed to expand once deployed within the heart.

The clasp 500 is opened and closed by applying and releasing tension on an actuating means such as an actuation line, suture, wire, rod, catheter, or the like (not shown) attached to the moveable arm 530. The suture is inserted through an opening 542 in the moveable arm 530 and looped around a pin 543 disposed in the opening 542. The smooth round shape of the pin 543 allows tension to be applied to the moveable arm 530 from many directions without causing the suture to wear. In certain embodiments, an intermediate suture loop is made through the opening and around the pin and the suture is inserted through the intermediate loop. An intermediate loop of suture material reduces friction experienced by the actuation suture relative to the friction between the actuation suture and the clasp material. When the actuation suture is looped around the pin 543, both ends of the suture extend back into and through the delivery sheath 102 (see FIG. 1). The suture can be removed by pulling one end of the suture proximally, until the other end of the suture pulls around the pin 543 and back into the delivery sheath.

Referring now to FIGS. 28-31, an exemplary barbed clasp 600 similar to barbed clasps 400 and 500 is shown in a variety of bent positions to illustrate the independent movement of the layers forming the barb clasps 400, 500, and 600. The barbed clasp 600 is formed from a top layer 602 and a bottom layer 604. The barbed clasp 600 includes a moveable arm 620, a fixed arm 622, a hinge portion 624. The moveable arm 620 includes a barbed portion 626 with barbs 628. The barbed clasp 600 does not include a cross-bar to prevent the moveable arm 620 from moving past the fixed arm 622. Instead of a cross-bar, the moveable arm 620 is held in a closed position with the fixed arm 622 by the inner paddle (not shown). To better illustrate the preloading of the clasp 600, FIGS. 28-31 show the fixed arm 622 moving relative to a stationary moveable arm 620. When assembled to an implantable device, however, the moveable arm 620 would move relative to the fixed arm 622 that is attached to the device.

Figure 28:
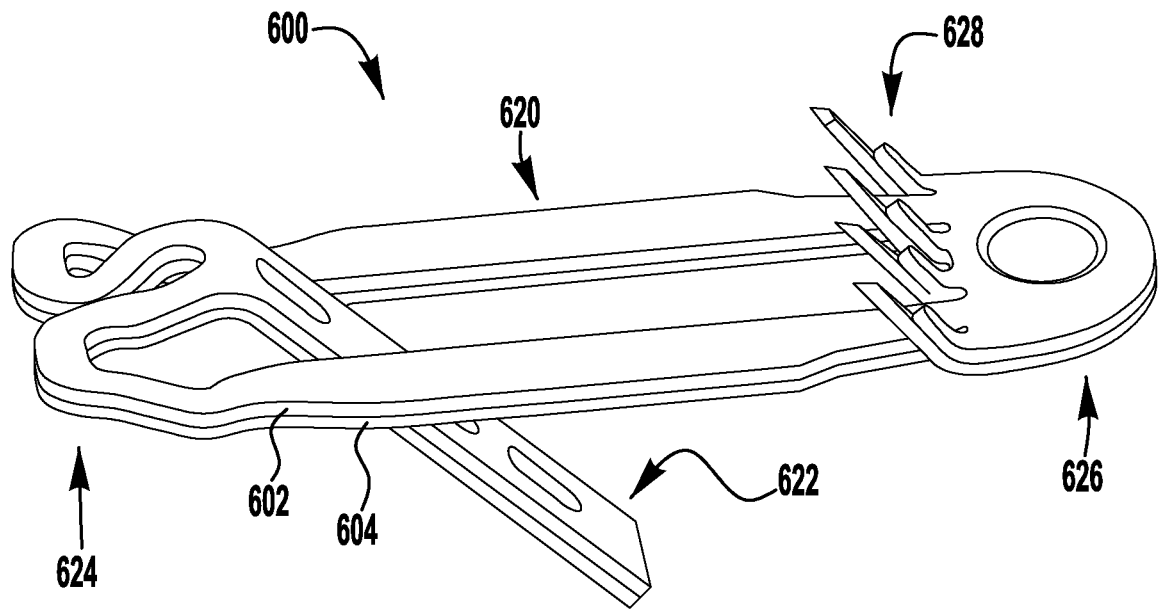
FIG. 28 shows a barbed clasp for an implantable prosthetic device according to a third embodiment.
Figure 29:
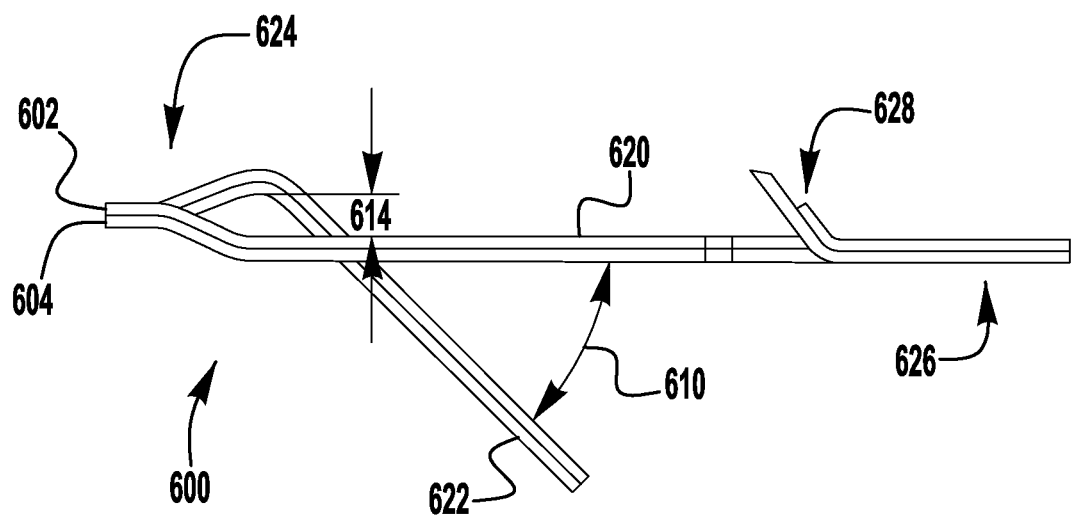
FIGS. 29-31 show a side view of a barbed clasp for an implantable prosthetic device in various stages of bending.

Referring now to FIGS. 28-29, the clasp 600 is shown in a preloading or shape setting condition. The fixed arm 622 is bent below the moveable arm 620 by an angle 610 before the shape setting operation is performed. Force must be applied then to return the fixed arm 622 to a parallel relationship with the moveable arm 620. Thus, increasing the preloading angle 610 increases the force required to move the fixed arm 622, thereby increasing the preloading spring force pinching the arms 620, 622 together when the clasp 600 is closed. In other words, the greater the angle 610, the greater the spring force applied to captured tissue by the arms 620, 622.

Figure 30:
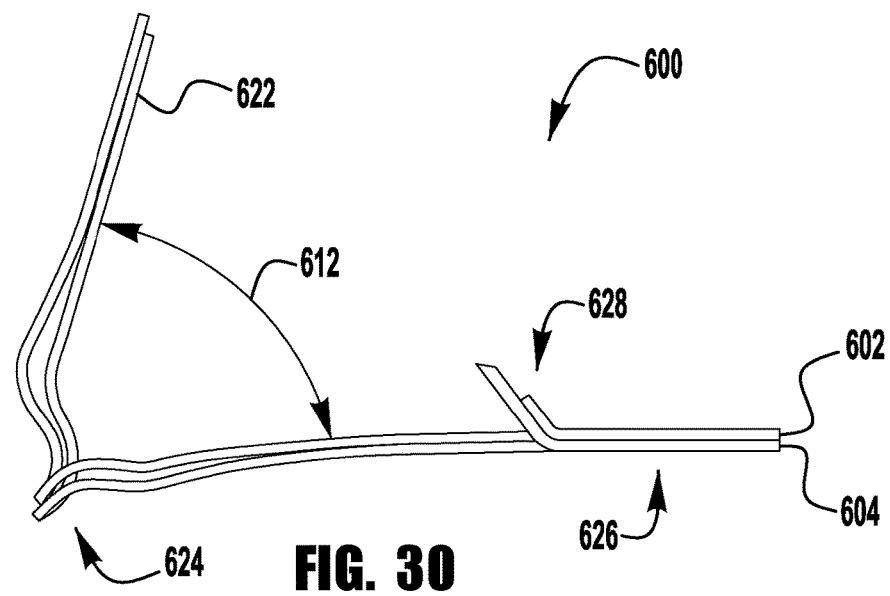
Figure 31:
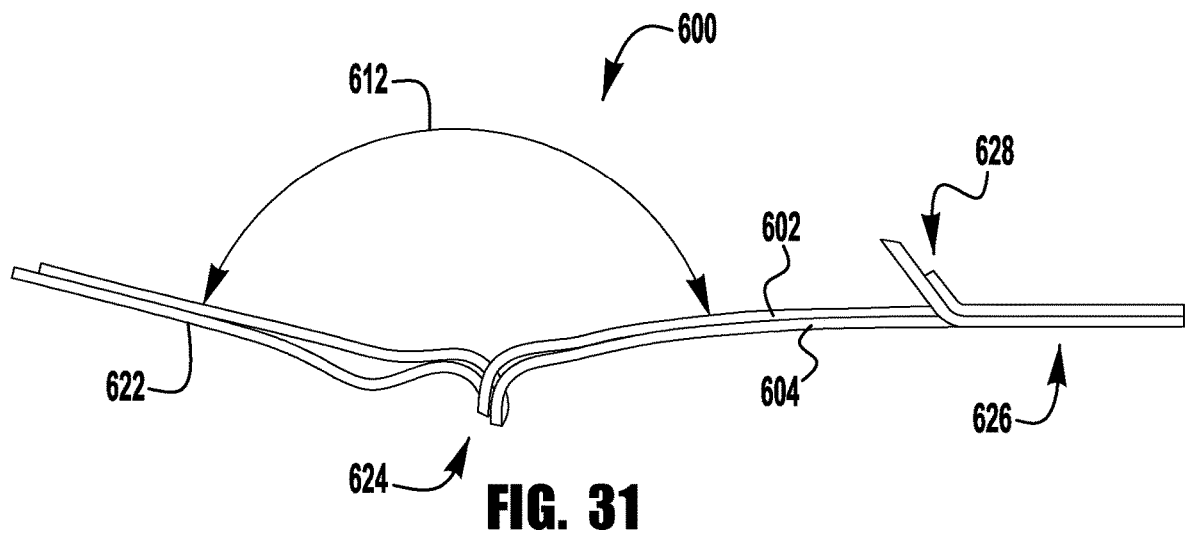

Referring now to FIGS. 30-31, the clasp 600 is shown being opened to an opening angle 612. As can be seen in FIGS. 30 and 31, the beam loops of the hinge portion 624 tend to separate as the clasp 600 is opened. Allowing the layers 602, 604 to separate during bending decreases strain on the material, thereby further increasing the maximum opening angle 612 that can be achieved before plastic deformation of the clasp material. As noted above, the hinge portion 624 is shaped to form somewhat spiral or helical beam loops, thereby forming a gap or step distance 614 between the arms 620, 622 (FIG. 29) that allows the leaflet tissue to be captured.

As the clasp 600 is opened, the layers 602, 604 in the fixed arm 622 slide relative to each other. In some embodiments, holes through the fixed arm 622 are elongated so that sutures securing the fixed arm 622 to the implantable device are not pinched by the sliding movement of the layers, nor are the layers 602, 604 constrained from sliding, which reduces strain experienced by the clasp material.

Referring now to FIGS. 32-35, exemplary barb clasps 700, 800, 900, and 1000 are shown. Barb clasps 700, 800, 900, and 1000, like clasps 400, 500, 600 can be used in the implantable devices 100, 200, and 300 described above. Unlike barbed clasps 400, 500, 600, however, barbed clasps 700, 800, 900, and 1000 are formed by laser cutting material from the side of the clasp rather than from the top. Laser cutting from the side reduces the operations required to manufacture the clasp and allows the thickness of the clasp to be varied to vary the bending properties of portions of the clasp based on the function of each portion. For example, hinge portions may be thinner to provide more flexibility while arms may be thickened to provide more stiffness.

Figure 32:
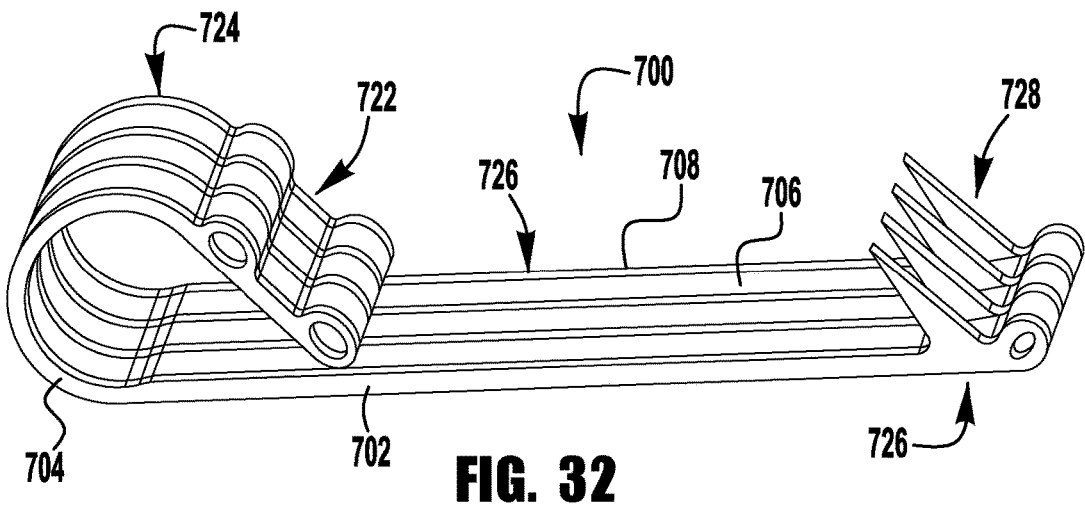
FIG. 32 shows a barbed clasp for an implantable prosthetic device according to a fourth embodiment.

Referring now to FIG. 32, a laminated barb clasp 700 is shown. The barb clasp 700 has thick and thin portions 702, 704 and is formed from alternating spacer layers 706 and barbed layers 708 to form a laminated structure. The clasp 700 includes a moveable arm 720, a fixed arm 722, and a hinge portion 724. The moveable arm 720 includes a barbed portion 726 having barbs 728 formed in the barbed layers 708. Forming the layers 706, 708 by laser cutting from a side profile allows the barbs 728 to be tapered, thereby providing a stiff barb with a sharp point. The fixed arm 722 includes holes to secure the clasp 700 to an implantable device. When assembled to an implantable device, the fixed arm 722 is extended by the attached inner paddle, thus the native tissue is pinched between the moveable arm 720 and the inner paddle of the device. The moveable and fixed arms 720, 722 are formed at an angle relative to each other such that an extension of the fixed arm 722 would intersect with the moveable arm 720. Attaching the fixed arm 722 to the inner paddle effectively extends the end of the fixed arm 722 such that the inner paddle would interfere with the moveable arm 720. The interference of the components causes the moveable arm 720 to be moved relative to the fixed arm 722 such that the clasp 700 is opened, thereby preloading the moveable arm 722 such that a pinch force is applied against the inner paddle when the clasp 700 is in the closed position. Thus, a pinch force is created between the moveable and fixed arms 720, 722 without shapesetting the moveable and fixed arms 720, 722 of the clasp 700. Alternatively, the individual layers are formed with the moveable and fixed arms 720, 722 parallel to each other and are then bent and shapeset such that the moveable arm 720 is biased toward the fixed arm 722 when the clasp 700 is affixed to the inner paddle.

Figure 33:
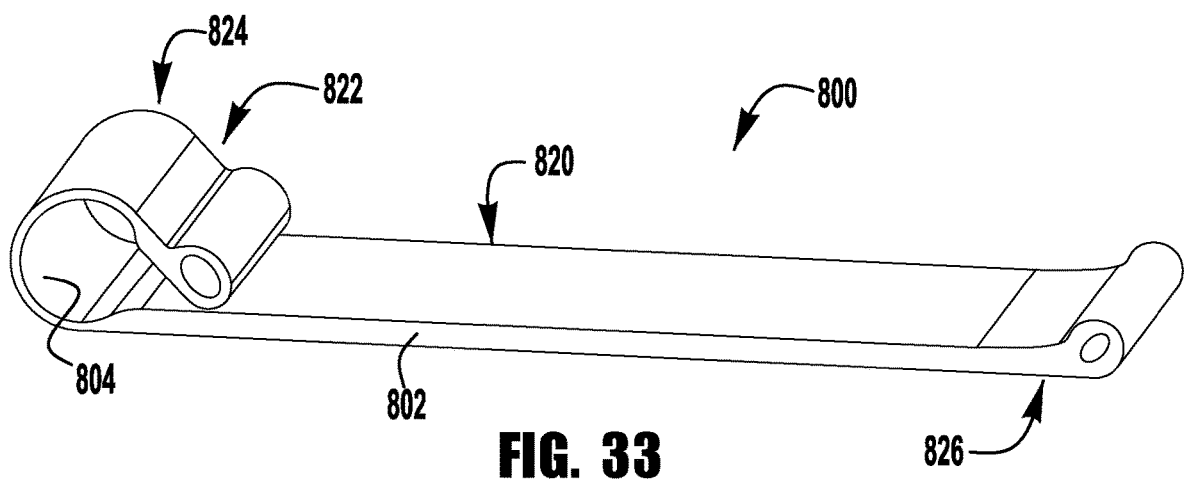
FIG. 33 shows a barbed clasp for an implantable prosthetic device according to a fifth embodiment.
Figure 34:
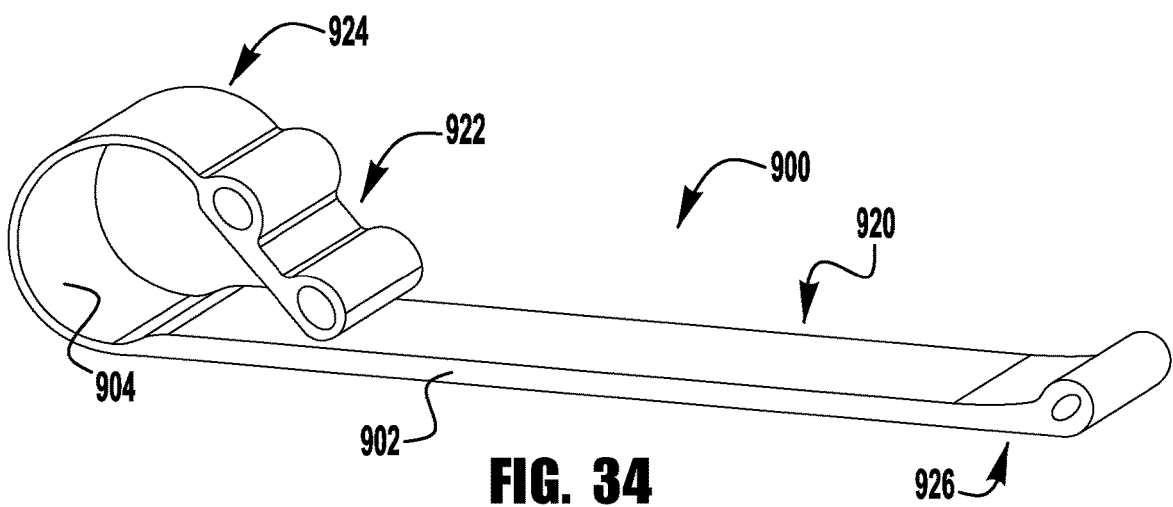
FIG. 34 shows a barbed clasp for an implantable prosthetic device according to a sixth embodiment.
Figure 35:
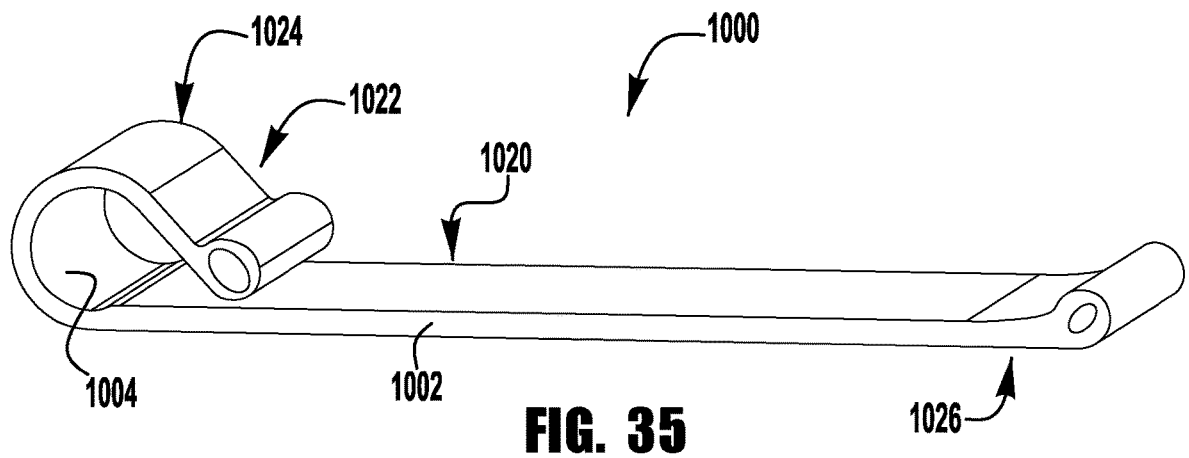
FIG. 35 shows a barbed clasp for an implantable prosthetic device according to a seventh embodiment.

Referring now to FIGS. 33-35, exemplary barb clasps 800, 900, 1000 are shown. The clasps 800, 900, 1000 are similar in overall shape while illustrating the variety of thicknesses possible when laser cutting clasps from the side. The clasps 800, 900, 1000 have a thin portion 804, 904, 1004 and a thick portion 802, 902, 1002. The clasps 800, 900, 1000 include a moveable arm 820, 920, 1020, a fixed arm 822, 922, 1022, a hinge portion 824, 924, 1024. The moveable arm 820, 920, 1020 includes a barb portion 826, 926, 1026 having barbs (not shown) similar to the barbs 728 of the barb portion 726 of clasp 700. As can be seen in FIGS. 33-35, holes can be provided in the fixed arm 822, 922, 1022 to secure the clasp 800, 900, 1000 to an implantable device. When assembled to an implantable device, the fixed arm 822, 922, 1022 is extended by the attached inner paddle, thus the native tissue is pinched between the moveable arm 820, 920, 1020 and the inner paddle of the device.

Figure 36:
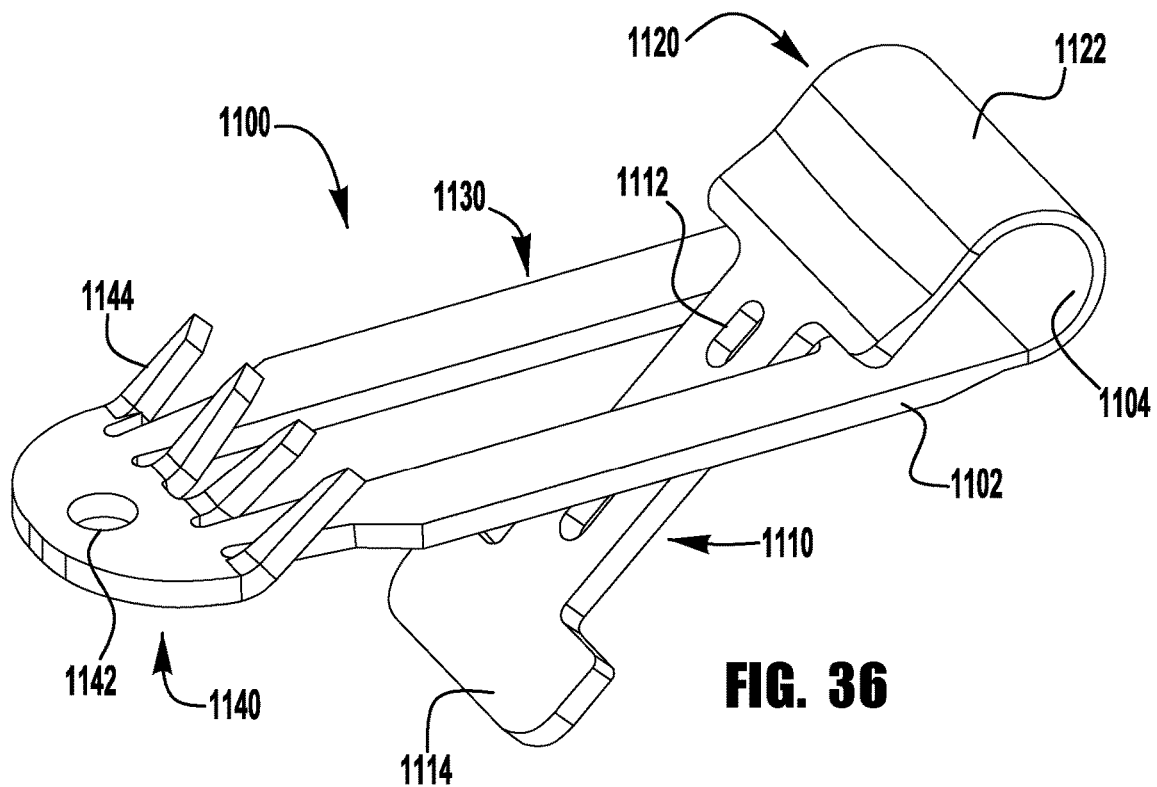
FIG. 36 shows a barbed clasp for an implantable prosthetic device according to an eighth embodiment.

Referring now to FIG. 36, an exemplary barbed clasp 1100 similar to barbed clasps 400, 500, 600 is shown. Unlike barbed clasps 400, 500, 600, however, barbed clasp 1100 is formed from a single layer of material that varies in thickness between a thick portion 1102 and a thin portion 1104. The barbed clasp 1100 includes a fixed arm 1110, a hinge portion 1120, and a moveable arm 1130. The fixed arm 1110 includes attachment holes 1112 and an optional integrated crossbar 1114. The hinge portion 1120 includes an arcuate hinge 1122 formed from the thin portion 1104. The moveable arm 1130 includes a barbed portion 1140 with barbs 1144. A suture (not shown) can be attached to an eyelet 1142 near the barbed portion 1140 to open and close the clasp 1100.

To form the barbed clasp 1100, a sheet of material is thinned to form the thin portion 1104. The shape of the clasp 1100 is then laser cut from the sheet of material so that the hinge portion 1120 is aligned with the thin portion 1104. The barbs 1144 and fixed arm 1110 are then bent into the position shown in FIG. 36 before shape setting. The optional T-shaped crossbar 1114 of the fixed arm 1110 must be twisted to insert it through the slot in the moveable arm 1130 for shape setting and to move the arms 1110, 1130 from the preloading position to a closed position. In certain embodiments, the optional T-shaped crossbar 1114 is omitted, is smaller, or is alternatively replaced with a relief in the moveable arm 1130, to facilitate ease of manufacture and shape setting. After the shape setting, the crossbar is twisted, moved back through the slot, and positioned on top of the thick portion 1102. The crossbar 1114 is positioned in generally the same manner as the crossbar 414 (see FIG. 26).

Like the clasps 400, 500 described above, the clasp 1100 can be opened fully without plastically deforming the clasp material while still providing pinching force when closed. Fewer steps are required to manufacture the clasp 1100 as compared to the clasps above, as the clasp 1100 is cut from a single sheet of material and no welding step is needed to weld layers of material together.

Referring now to FIGS. 37-52, an exemplary barbed clasp 1200 for use in implantable prosthetic devices, such as devices 100, 200, 300 described above, is shown. The barbed clasp 1200 is formed from a single layer 1202 of material. The barbed clasp 1200 includes a fixed arm 1210, a hinged portion 1220, and a movable arm 1230 having a barbed portion 1240. The hinged portion 1220 is spring-loaded so that the fixed and moveable arms 1210, 1230 are biased toward each other when the barbed clasp 1200 is in a closed condition. When assembled to an implantable prosthetic device, the fixed arm 1210 is attached to a portion of the prosthetic device. The clasp 1200 is opened by pulling on an actuating mans such as an actuation line or suture attached to the moveable arm 1230 until the spring force of the hinge portion 1220 is overcome.

Figure 39:
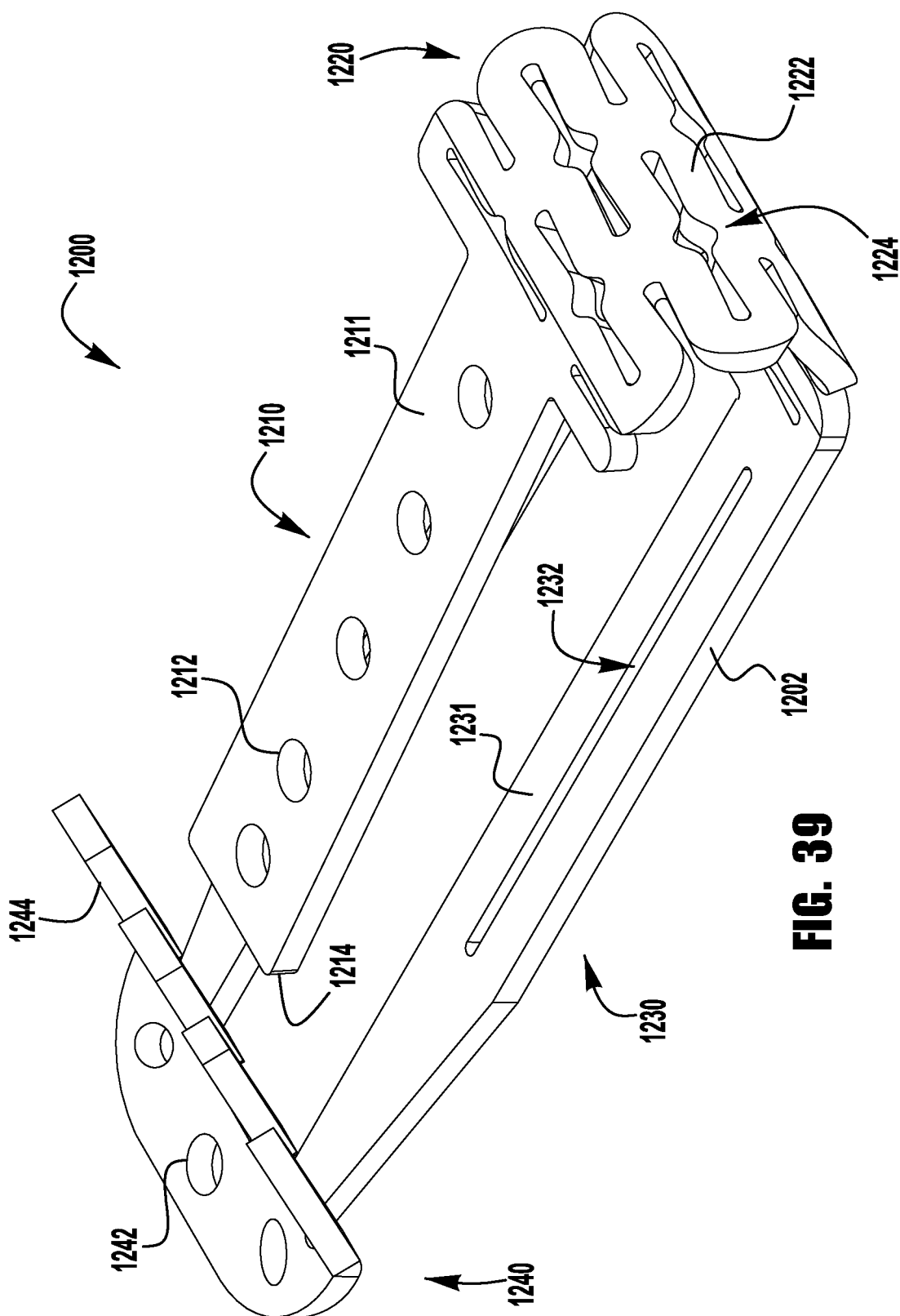
Figure 40:
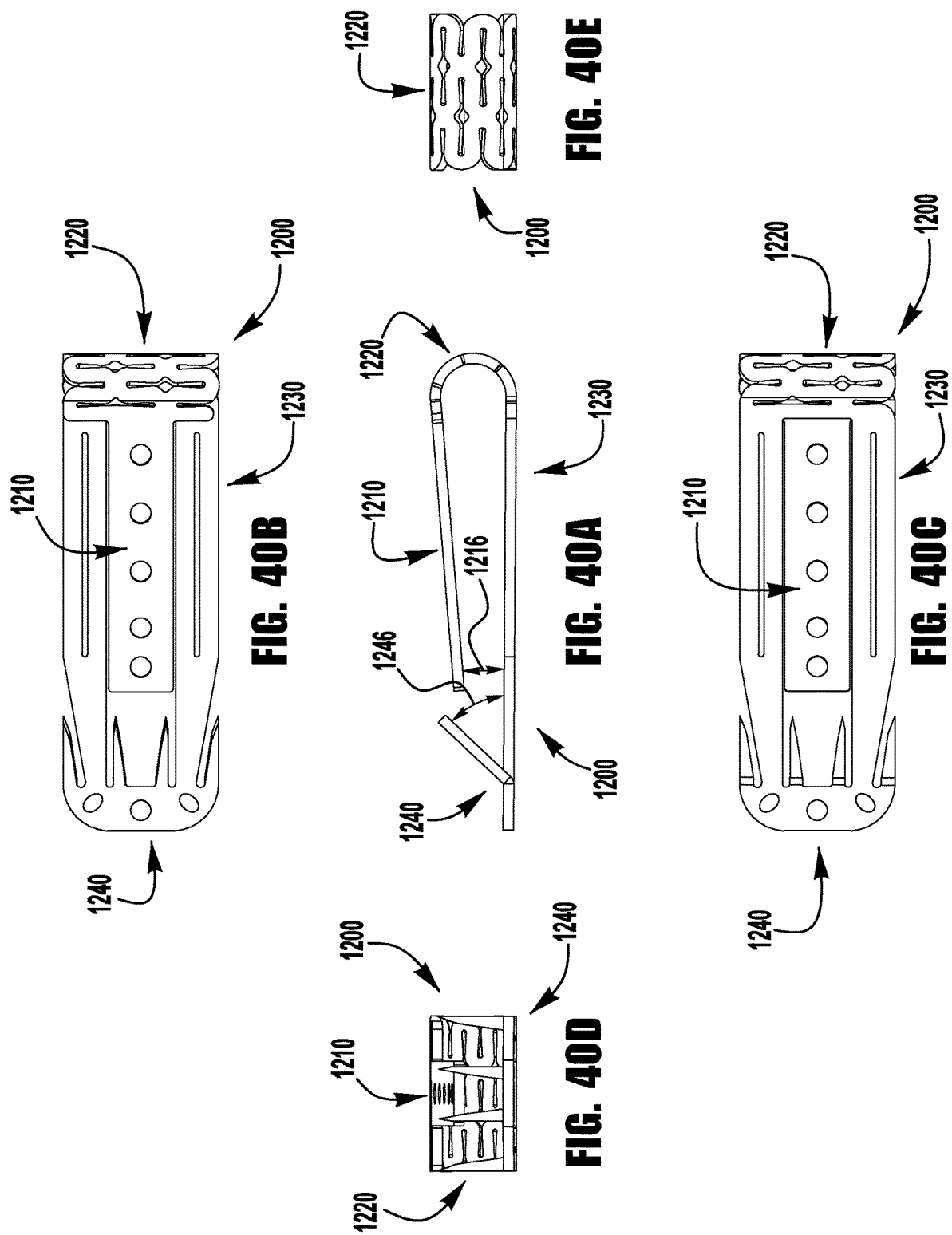
Figure 41:
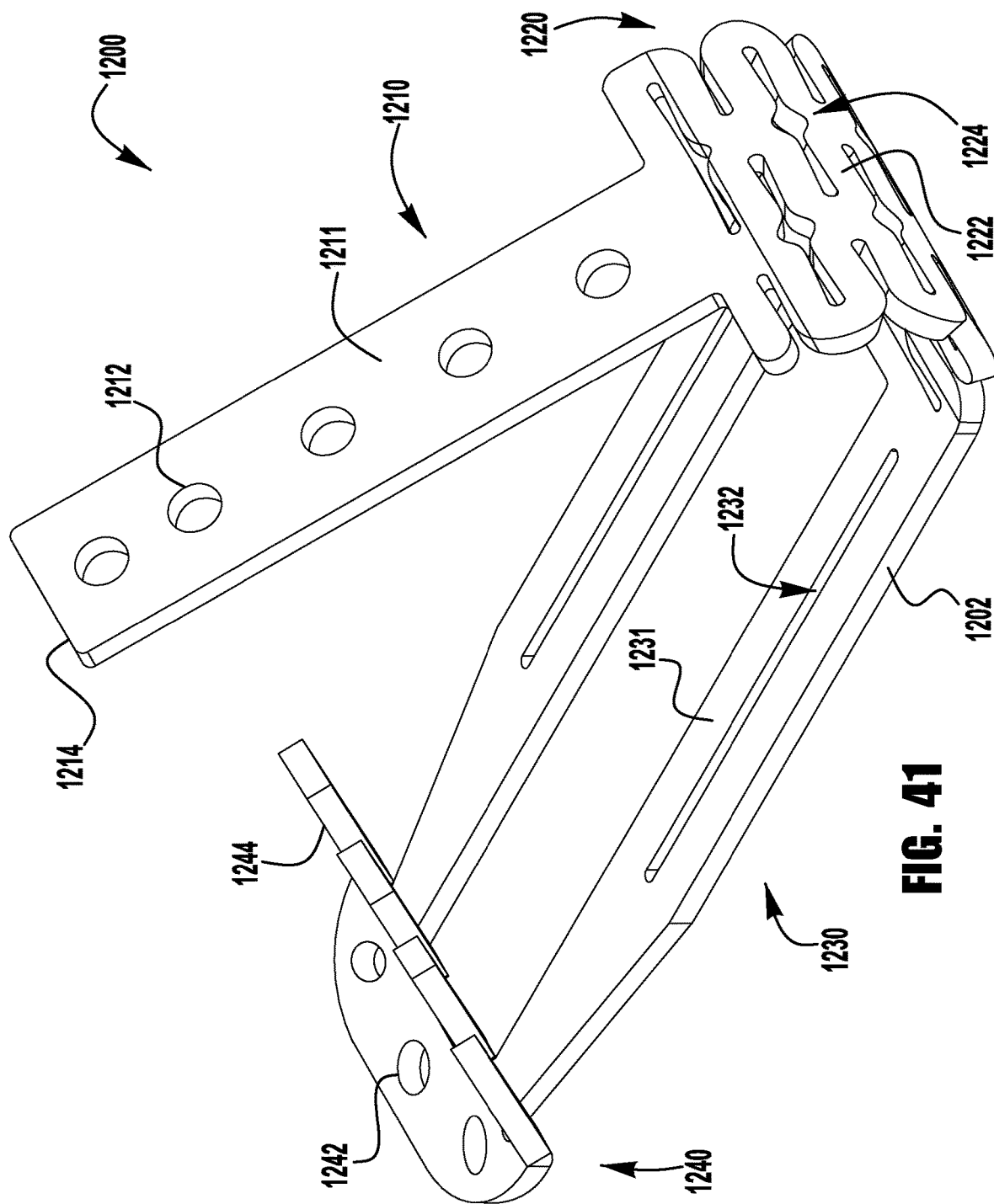
Figure 42:
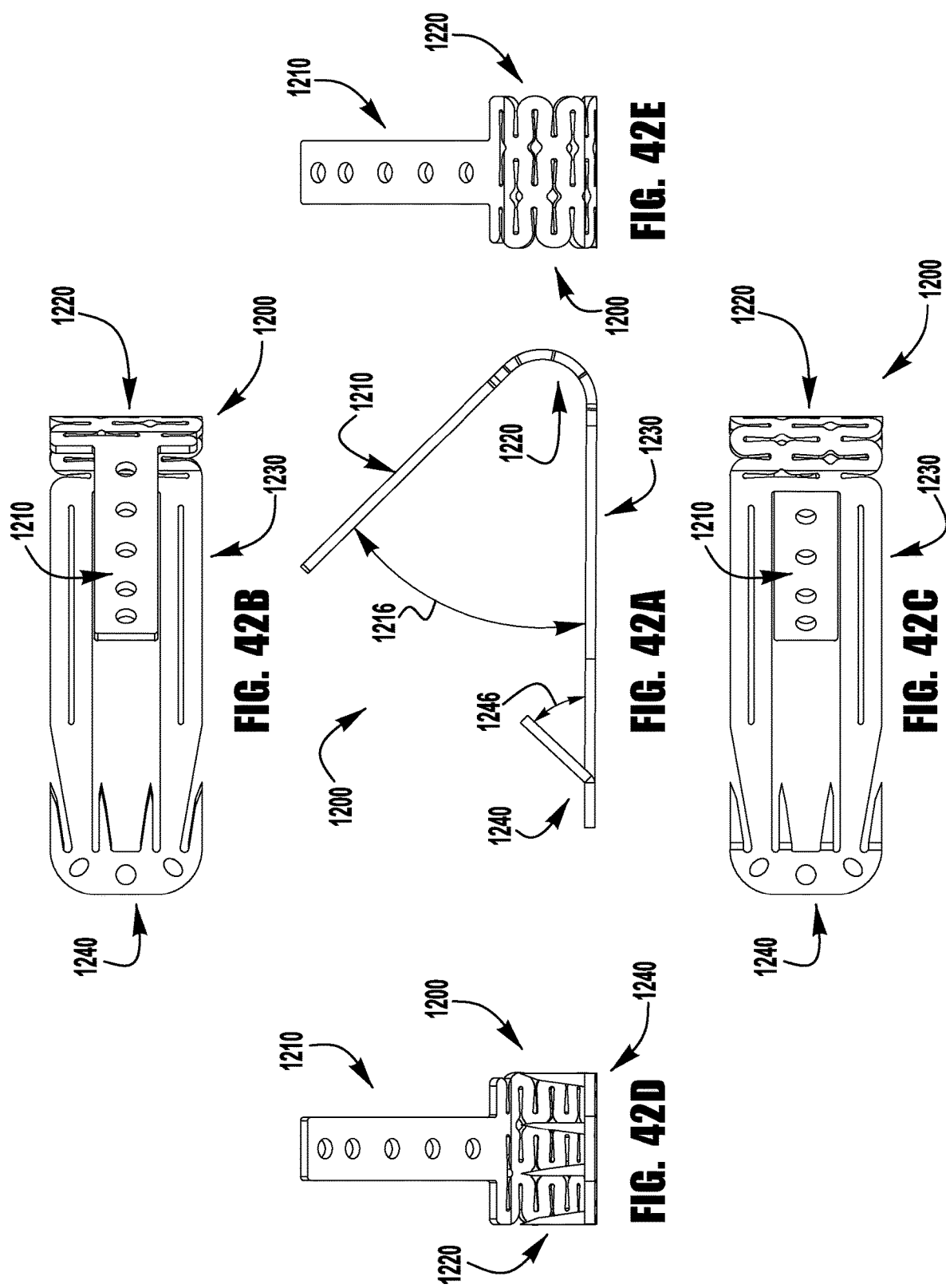
Figure 43:
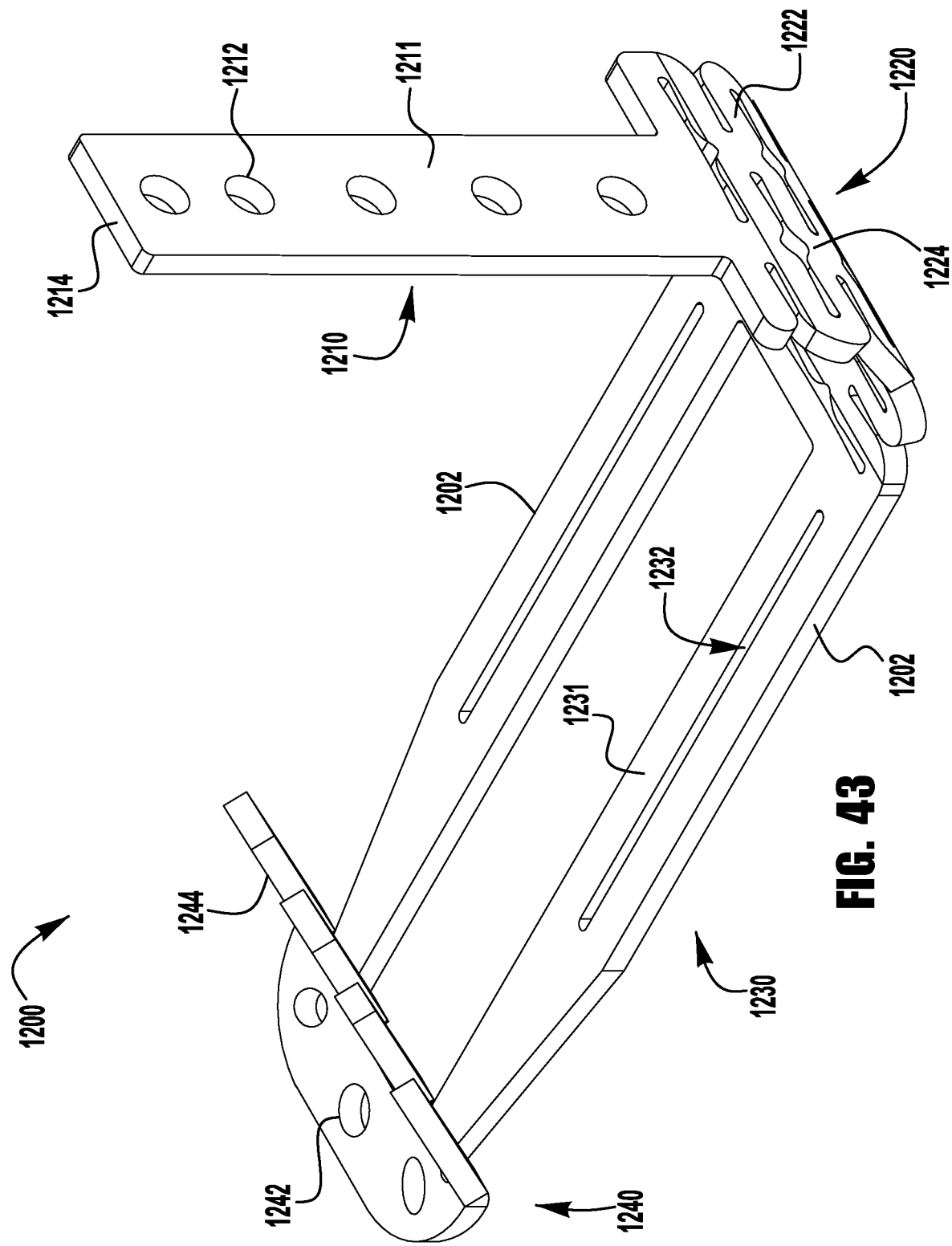
Figure 44:
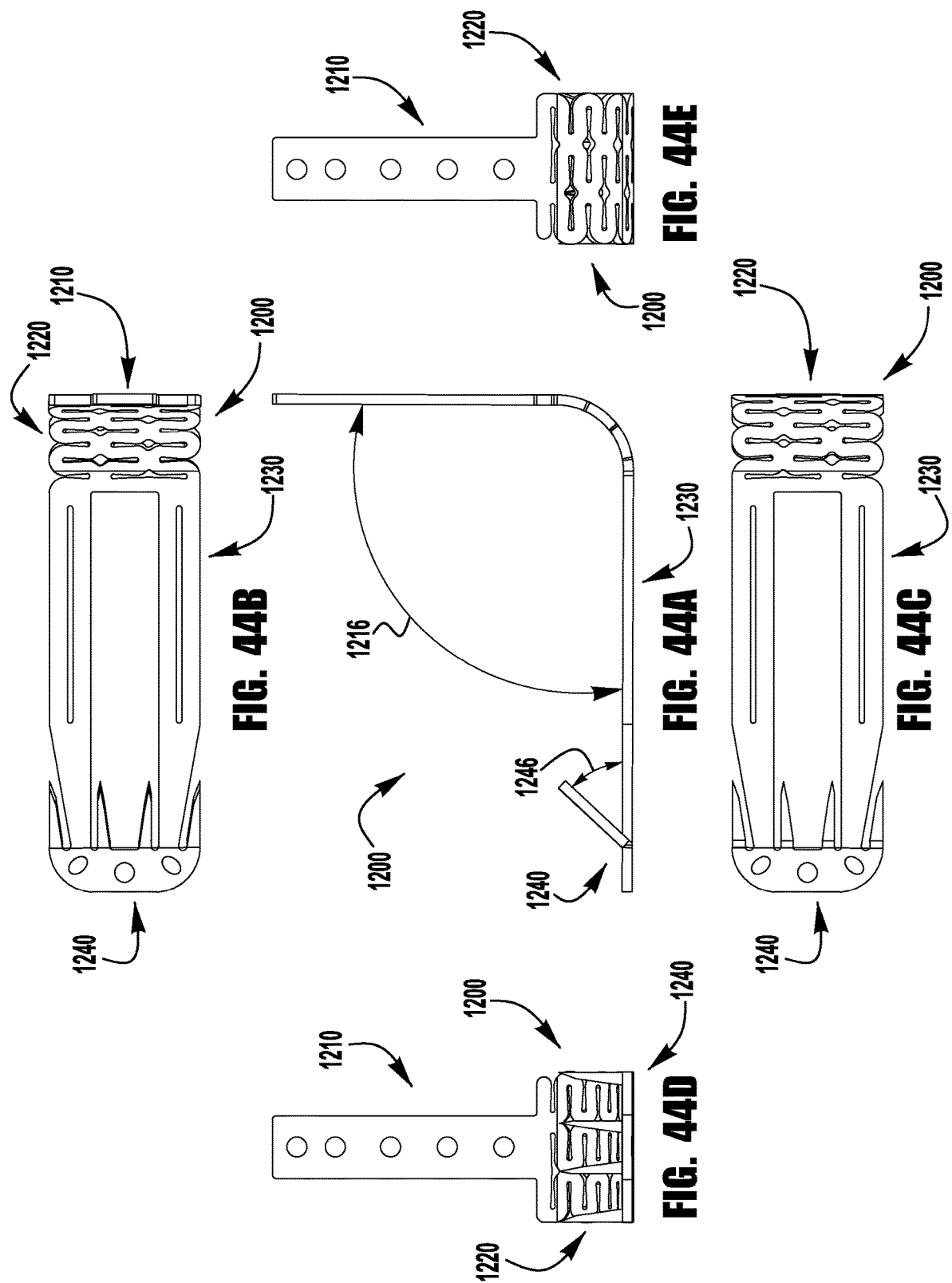
Figure 45:
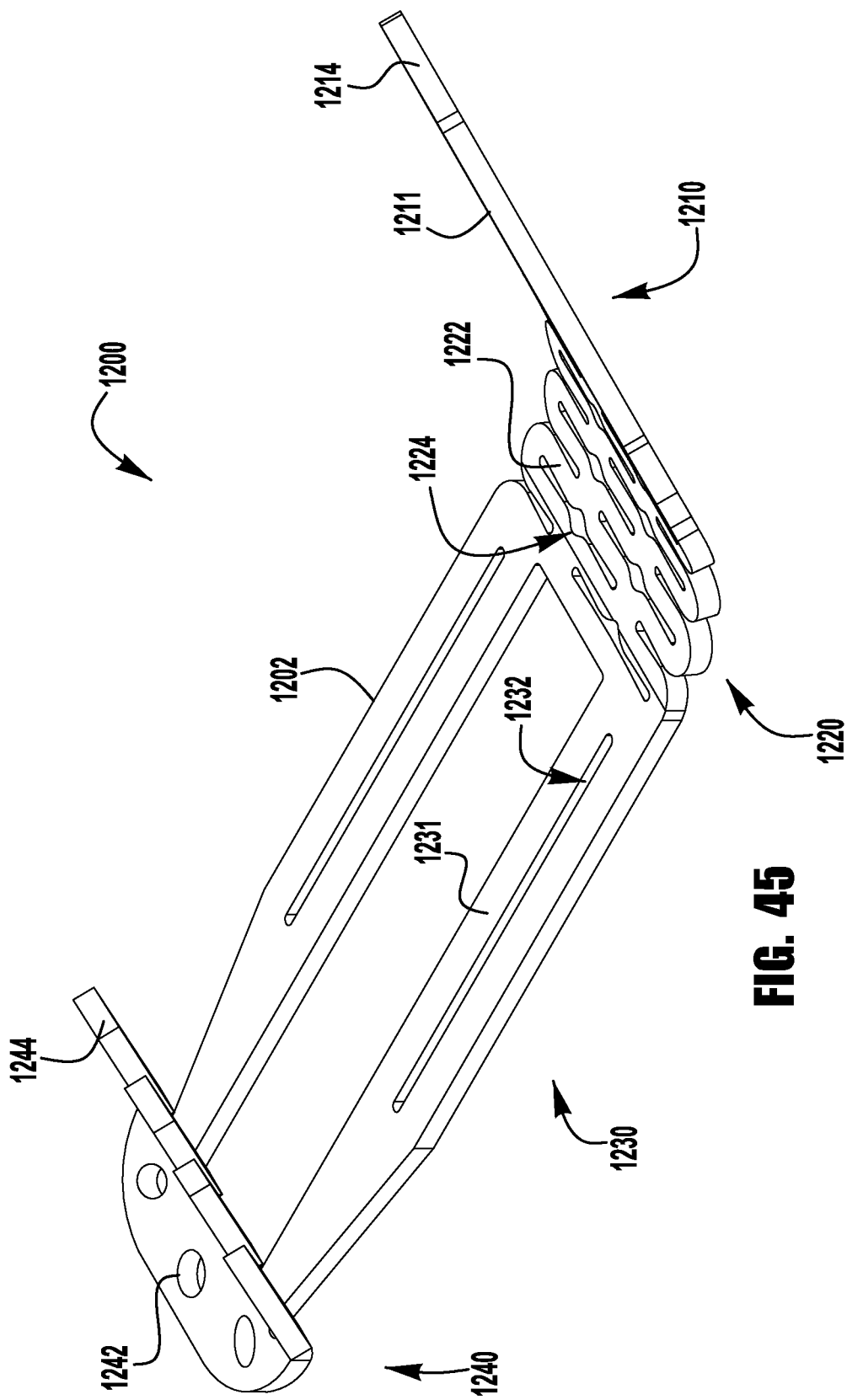

The fixed arm 1210 is formed from a tongue 1211 of material extending from the hinged portion 1220 between two side beams 1231 of the moveable arm 1230 to an end 1214. In some embodiments, the moveable arm is formed from a tongue of material that extends between two side beams of the fixed arm. The tongue 1211 is biased between the side beams 1231 by the hinge portion 1220 such that force must be applied to move the tongue 1211 from a neutral position located beyond the side beams 1231 to a preloaded position that is nearly parallel or parallel with the side beams 1231, as can be seen in FIGS. 39-40E. The tongue 1211 is held in the preloaded position when it is attached to a paddle of an implantable prosthetic device. The end 1214 of the tongue 1211 may optionally have a T-shape cross-member that engages the side beams 1231 to hold the tongue 1211 in the preloaded position.

In certain embodiments, the angle between the fixed and moveable arms 1210, 1230 when the tongue 1211 is in the neutral position is about 30 to about 120 degrees, 40 to about 110 degrees, or about 50 to about 100 degrees, or about 60 to about 90 degrees, or about 90 degrees. The tongue 1211 includes holes 1212 for receiving sutures (not shown) that attach the fixed arm 1210 to an implantable device.

The hinge portion 1220 is formed by a plurality of torsional spring segments 1222 arranged in a repeating pattern extending from the tongue 1211 of the fixed arm 1210 to the side beams 1231 of the moveable arm 1230. Each spring segment 1222 is joined with other spring segments 1222 to form a repeating pattern. Joining multiple segments 1222 together allows the hinge portion 1220 to bend a considerable amount while avoiding plastic deformation of the material as the individual torsional spring segments 1222 are twisted. For example, in certain embodiments, the tongue 1211 can be pivoted from the neutral position that is approximately 90 degrees beyond the moveable arm 1230 to a fully open position that ranges from about 140 degrees to about 200 degrees, to about 170 degrees to about 190 degrees, or about 180 degrees. from the moveable arm 1230 without plastically deforming the clasp material. In certain embodiments, the clasp material can plastically deform during opening without reducing or without substantially reducing the pinch force exerted between the fixed and moveable arms in the closed position. The pattern spring segments 1222 are formed from open and closed cutouts 1224 in the hinge portion 1220. Exemplary spring segments and their arrangement in a pattern are described below and shown in FIGS. 51A-52.

Preloading the tongue 1211 enables the clasp 1200 to maintain a pinching or clipping force on the native leaflet when closed while also being able to be opened wide to more easily capture the native leaflet. The preloading of the tongue 1211 provides a significant advantage over prior art clips that provide little or no pinching force when closed. Additionally, closing the clasp 1200 with spring force is a significant improvement over clips that use a one-time locking closure mechanism, as the clasp 1200 can be repeatedly opened and closed for repositioning on the leaflet while still maintaining sufficient pinching force when closed.

The barbed portion 1240 of the moveable arm 1230 includes eyelets 1242 and barbs 1244. Positioning the barbed portion of the clasp 1200 at an end of the moveable arm 1230 increases the space between the barbs 1244 and the fixed arm 1210 when the clasp 1200 is opened, thereby improving the ability of the clasp 1200 to successfully capture a leaflet during implantation. This distance also allows the barbs 1244 to more reliably disengage from the leaflet for repositioning. In certain embodiments, the barbs of the clasps may be staggered longitudinally to further distribute pinch forces and local leaflet stress. In certain embodiments, the ends of the barbs 1244 are further sharpened using any suitable sharpening means.

The barbs 1244 are laterally spaced apart at the same distance from the hinge portion 1220, providing a superior distribution of pinching forces on the leaflet tissue while also making the clasp more robust to leaflet capture than barbs arranged in a longitudinal row. In some embodiments, the barbs 1244 can be staggered to further distribute pinch forces and local leaflet stress.

The barbs 1244 are angled away from the moveable arm 1230 at an angle 1246 (FIG. 38A) such that they easily engage tissue of the native leaflets with minimal pinching or clipping force. During use, the barbs 1244 may penetrate the native leaflet tissue, though penetration of the tissue is not necessary for the clasp 1200 to securely grasp the leaflets. The barbs 1244 extend from the moveable arm at an angle 1246 of about 20 degrees to about 90 degrees, or about 40 degrees to about 70 degrees, or about 50 to about 60 degrees, or about 53 degrees. The angle of the barbs 1244 provides further benefits, in that force pulling the implant off of the native leaflet will encourage the barbs 1244 to further engage the tissue, thereby ensuring better retention. Retention of the leaflet in the clasp 1200 is further improved by the position of the end 1214 of the fixed arm 1210 when the clasp 1200 is closed. In this arrangement, the tissue engaged by the barbs 1244 is pinched against the moveable arm 1230 at the end 1214 location, thereby forming the tissue into an S-shaped torturous path as it passes over the barbs 1244. Thus, forces pulling the leaflet away from the clasp 1200 will encourage the tissue to further engage the barbs 1244 before the leaflets can escape. The end 1214 can optionally be shapeset with a slight bend toward the moveable arm 1230 to accentuate the S-shape of the tortuous path of the tissue captured between the fixed and moveable arms 1210, 1230.

The layer of material 1202 of the clasp 1200 is laser cut from a sheet of shape-memory alloy, such as Nitinol. Portions of the layer 1202, such as the fixed arm 1210, hinge portion 1220 and barbs 1244 are bent into a desired position. The clasp 1200 is then subjected to a shape-setting process so that internal forces of the material will tend to return to the set shape after being subjected to deformation by external forces. After shape setting, the tongue 1211 is moved to its preloaded, closed, or open positions to be attached to the implantable device. Consequently, the clasp 1200 can be substantially flattened in the closed position for delivery through a delivery sheath and allowed to expand once deployed within the heart.

The clasp 1200 is opened and closed by applying and releasing tension on an actuation line or suture (e.g., suture 2504 of FIG. 71) attached to the moveable arm 1230. The suture is inserted through at least one of the eyelets 1242 located near the barbed portion 1240 of the moveable arm 1230 before returning to the delivery sheath. In certain embodiments, an intermediate suture loop is made through one or more of the eyelets 1242 and the actuation suture is inserted through one or more of the intermediate loops. An intermediate loop of suture material reduces friction experienced by the actuation suture relative to the friction between the actuation suture and the clasp material. When the suture is looped through the eyelet 1242 or intermediate loop, both ends of the actuation suture extend back into and through the delivery sheath 102 (see, e.g., FIG. 1). The suture can be removed by pulling one end of the suture proximally until the other end of the suture pulls through the eyelet or intermediate loop and back into the delivery sheath.

Like the clasps 400,500 described above, the clasp 1200 can be opened fully without plastically deforming the clasp material while still providing pinching force when closed. Fewer steps are required to manufacture the clasp 1100 as compared to the clasps above, as the clasp 1200 is cut from a single sheet of material and no welding step is needed to weld layers of material together.

Referring now to FIGS. 37-48E, the clasp 1200 is shown in various bending positions ranging from a neutral position (FIGS. 37-38E) to a fully open position (FIGS. 47-48E). Though the fixed arm 1210 is shown in different positions in FIGS. 37-48E, once installed in an implantable device, the moveable arm 1230 is actuated by the surgeon to move relative to the device while the fixed arm 1210 remains stationary relative to the device.

Figure 37:
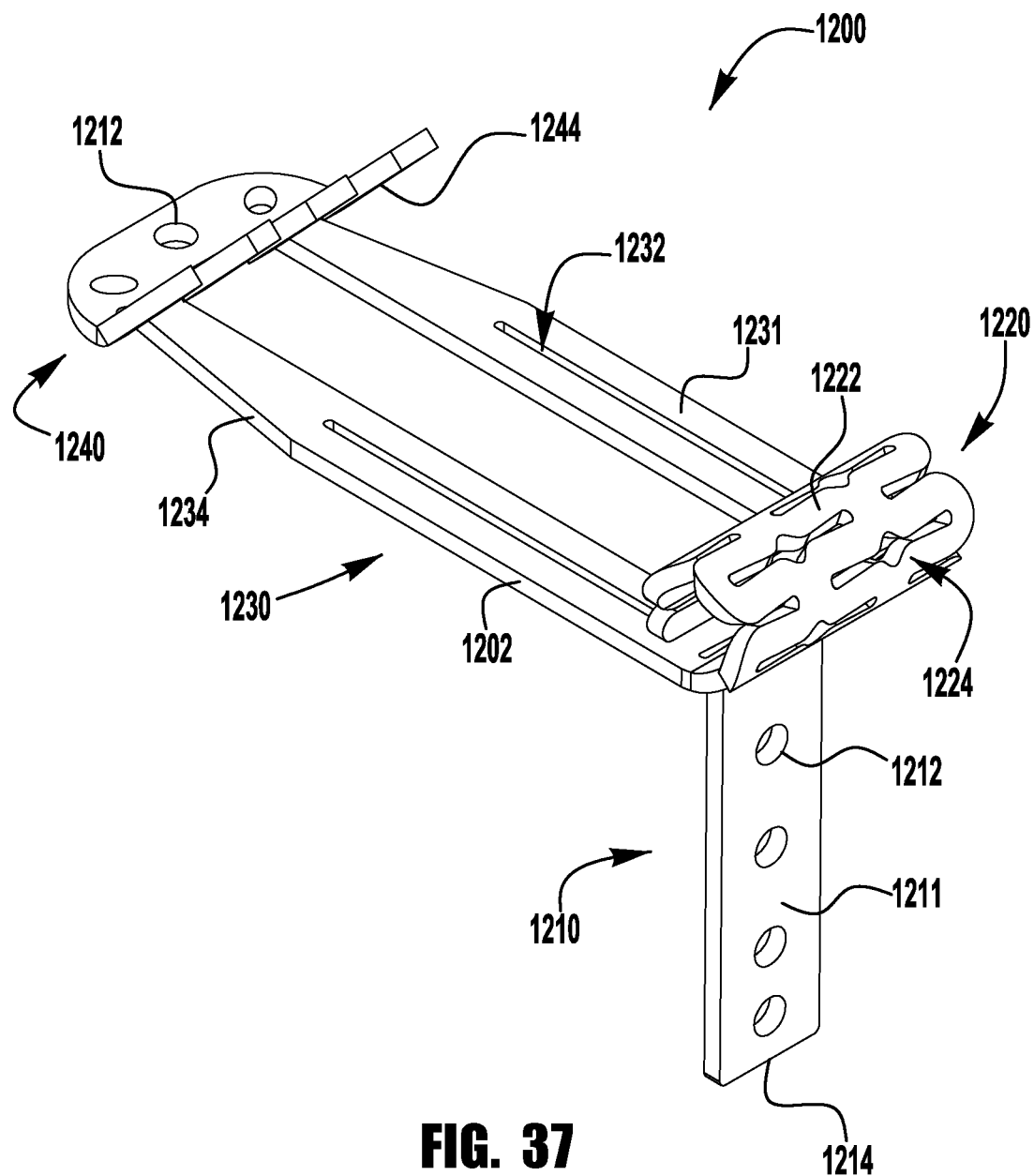
Figure 38:
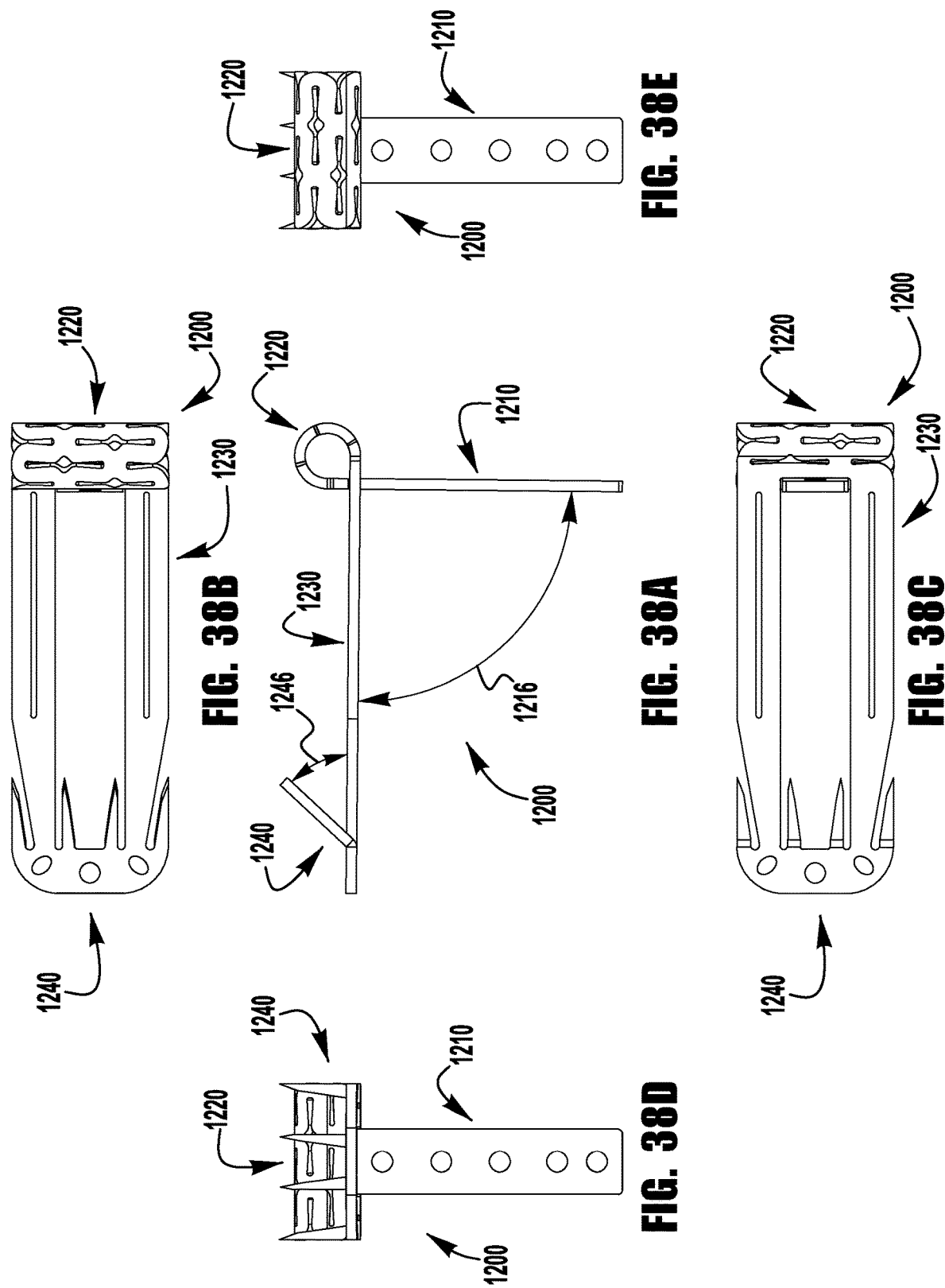

FIGS. 37-38E show the clasp 1200 in the neutral position for shape-setting. During shape-setting, the tongue 1211 of the fixed arm 1210 is bent to a tongue angle 1216 that is about 60 degrees to about 120 degrees, or about 90 degrees below the side beams 1231 of the moveable arm 1230. After shape-setting, the tongue 1211 remains in the shape-setting or neutral position unless acted upon by forces to move the tongue 1211 into other positions. Thus, when the tongue 1211 is moved to a preloading or closed position (FIGS. 39-40E) internal forces of the clasp material are exerted in the closing direction, thereby generating a pinching force when the clasp 1200 is in the closed or preloaded condition. During implantation of a medical device including the clasp 1200, the moveable arm 1230 is actuated with a suture (not shown) to change the angle 1216 between the fixed and moveable arms 1210, 1230. The clasp 1200 is shown in a one-quarter open condition in FIGS. 41-42E, a half open condition in FIGS. 43-44E, a three-quarter open condition in FIGS. 45-46E, and a fully open condition in FIGS. 47-48E. The angle 1216 between the fixed and moveable arms 1210, 1230 in the fully open position may be about 140 degrees to about 200 degrees, to about 170 degrees to about 190 degrees, or about 180 degrees. That is, the clasp 1200 is capable of being opened substantially completely flat without plastic deformation of the clasp material.

Referring now to FIGS. 49-50, the layer 1202 of material for forming the clasp 1200 is shown in a pre-shape setting condition, that is, in a substantially flat condition after being laser cut from a sheet of material. FIG. 50 in particular clearly shows the repeating nature of the pattern of spring segments 1222 and cutouts 1224 that form the hinge portion 1220.

Referring now to FIGS. 51A-51D, exemplary torsional spring segments 1300, 1400, 1500, 1600 for a patterned hinge portion (e.g., hinge portion 1220 of the clasp 1200) are shown. The spring segments 1300, 1400, 1500, 1600 are arrangeable in a repeating pattern that is cut out of a single piece so that there are no physical seams between the individual segments. Thus, the shape of the spring segments 1300, 1400, 1500, 1600 is defined by the cutouts in the hinge portion and imaginary boundaries at the "joints" between segments.

Referring now to FIG. 51A, the spring segment 1300 is formed by cutouts 1301 made in a layer 1302 of material resulting in a substantially rotationally symmetric, S-like shape. Each spring segment 1300 extends from a first end 1310 to a second end 1320 between a first side 1330 and a second side 1340. A first end joining location 1312 is located at the first end 1310 adjacent the first side 1330. A first side joining location 1332 is located at the first side 1330 adjacent the first end 1310. A second end joining location 1322 is located at the second end 1320 adjacent the second side 1340. A second side joining location 1342 is located at the second side 1340 adjacent the second end 1320. Side surface 1304 extend between the first end joining location 1312 and the second side joining location 1342, and between the second end joining location 1322 and the first side joining location 1332. An inner corner 1306 is formed near each side joining location 1332, 1342.

Referring now to FIGS. 51B-51D, spring segments 1400, 1500, 1600 are shown. These spring segments 1400, 1500, 1600 are similar in structure to the spring segment 1300 described above, though spring segments 1400, 1500, 1600 include an outer corner 1408, 1508, 1608 near each end joining location opposite the side joining location. The shapes of the spring segments 1300, 1400, 1500, 1600 vary in the size and shape of the side surfaces 1304, 1404, 1504, 1604, rounded inner corners 1306, 1406, 1506, 1606 and rounded outer corners 1408, 1508, 1608. For example, the side surfaces 1304, 1404 are substantially straight, while the side surfaces 1504, 1604 are concave. These differences in shape change the stress distribution in hinge portions formed from a pattern of the differently shaped spring segments.

Figure 52:
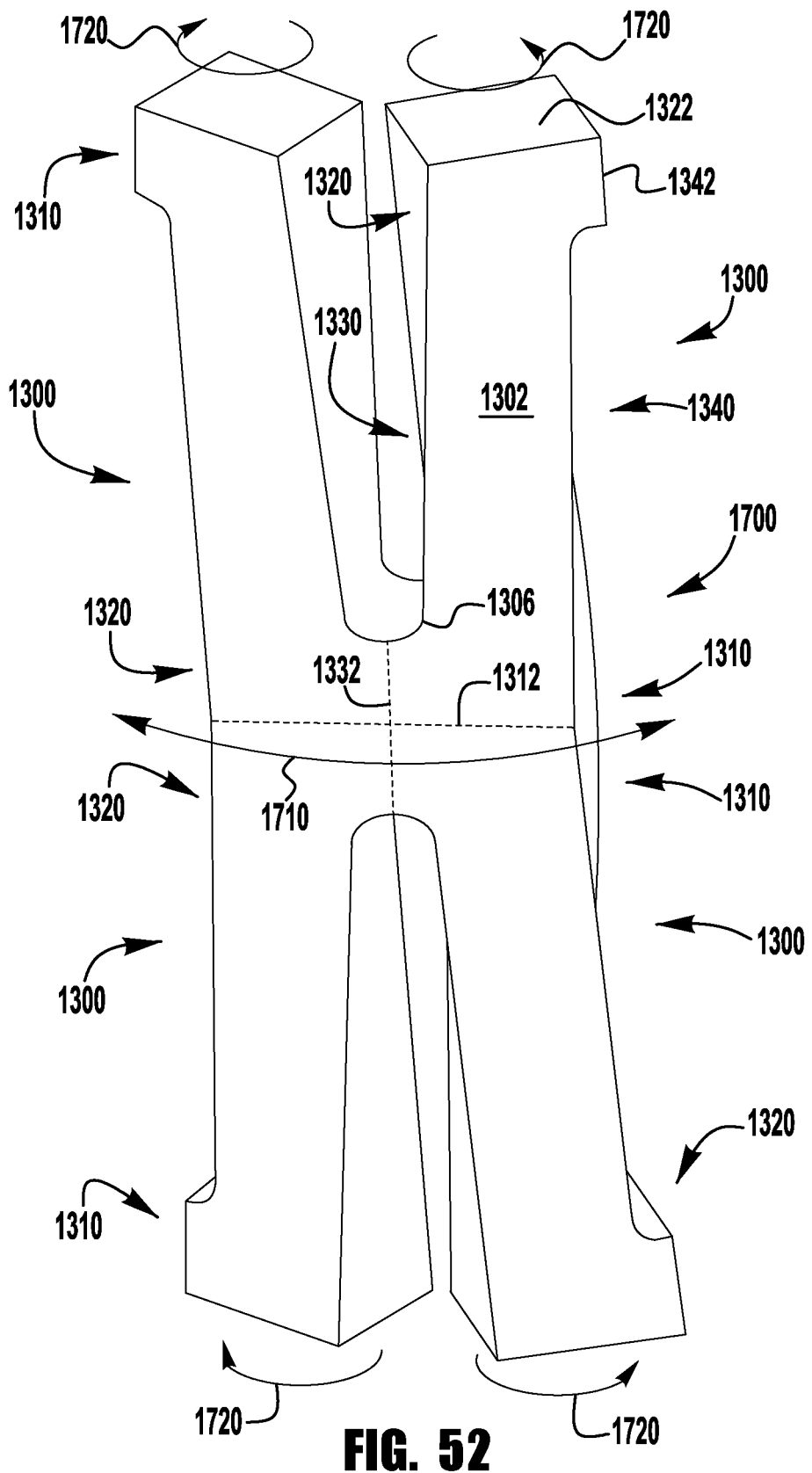

Referring now to FIG. 52, an exemplary spring grouping 1700 of spring segments 1300 is shown. As can be seen in FIG. 52, side joining locations 1332, 1342 are joined to other side joining locations 1332, 1342 and end joining locations 1312, 1322 are joined to other end joining locations 1312, 1322. The substantially rotationally symmetric shape of the spring segments 1300 allows either end 1310, 1320 or side 1330, 1340 of one segment to be joined to either end 1310, 1320 or side 1330, 1340 of another segment. Various patterns may then be formed, such as the H-pattern formed by the grouping 1700 in FIG. 52. While the segments 1300, 1400, 1500, 1600 are substantially rotationally symmetric, individual segments in a pattern of segments may be modified to form rounded outer edges of a hinge portion or to adapt to the fixed or moveable arm of a clasp.

When the spring grouping 1700 is subjected to a bending force 1710 each of the segments 1300 is twisted in the direction indicated by the arrows 1720. Consequently, the individual spring segments 1300 are subjected to torsional strain and not bending strain. One can also see that the deformation of the material 1302 is reduced relative to the bending of a flat sheet of material being bent in a similar manner while maintaining the spring force of the hinge portion of the clasp. As a result, a hinge portion formed from a pattern of torsional spring segments is strong and flexible.

To form a patterned hinge portion, such as the hinge portion 1220 described above, a pattern comprising plurality of spring segments are arranged in rows and columns. The spring segments are arranged with their longitudinal and lateral axes in the same orientation, as can be seen in FIGS. 49-50 and 52. In certain embodiments, the spring segments may be rotated relative to each other to form different spring patterns. The spring segments are organized into columns and rows. Columns are defined along the longitudinal axis of the clasp, while rows are defined along the lateral axis of the clasp. Thus, a column of spring segments is as wide as the longest dimension of an individual spring segment, while a row of spring segments has a height equal to the shortest dimension of an individual spring segment. For example, the clasp 1200 shown in FIG. 50 includes three columns and seven rows of spring segments (not including partial rows connecting the hinge portion to the fixed and moveable arms). Where the ends of segments border an edge of the clasp, two segments in adjacent rows are joined together at one location, forming a U-shaped grouping. Individual spring segments or groupings of spring segments may be modified away from their rotational symmetry to increase the smoothness and/or robustness of the edges of the hinge portion. Where the ends of segments are located at an intersection of two columns, the segments may join up to three other segments, forming an X-shaped grouping, like the grouping 1700 shown in FIG. 62. The patterned hinge may include any suitable number of rows and columns of spring segments. The size and shape of each segment may be adjusted to adjust the spring parameters of the patterned hinge. The size and shape of the spring segments may be uniform throughout the patterned hinge or may vary based on the location of the spring segment within the pattern.

Figure 55:
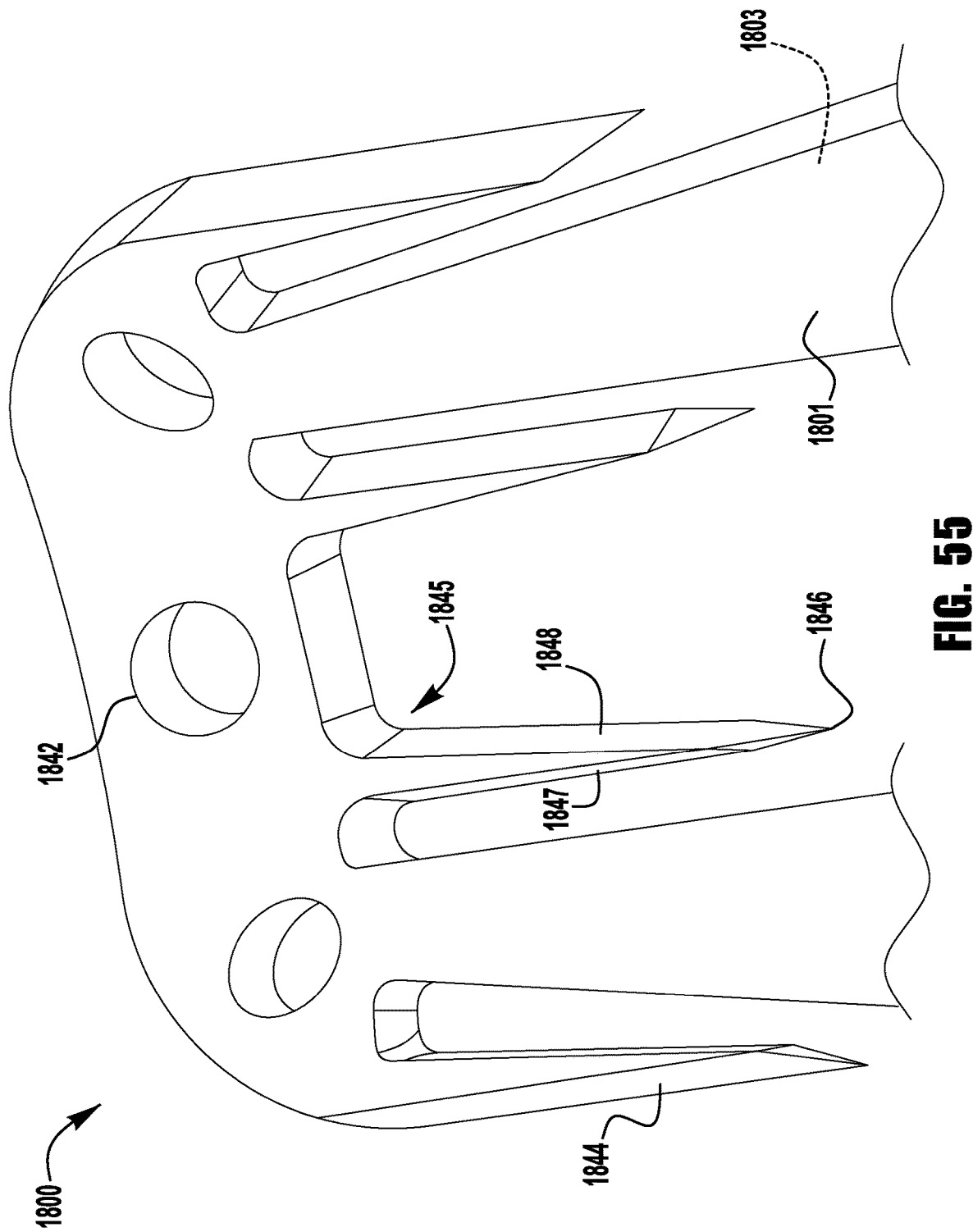

Referring now to FIGS. 53-55, an exemplary barb clasp 1800 is shown that is cut from a tube of material 1802 using four-axis laser cutting (X, Y, Z, and rotation axes) and five-axis laser cutting (X, Y, Z, and two tilt-axes for the laser head). The tube can first be cut into segments and then each segment is cut in generally the same way that a flat piece of stock or blank material is cut; that is, the tube provides a curved blank instead of a flat blank. The additional degrees of freedom of the laser cutter allow the tube to be rotated or the head of the laser cutter to be tilted during laser cutting. Rotating the tube or tilting the laser cutting head allows the barbs to be cut in the sharper barb configuration shown in FIG. 55 without requiring a separate sharpening operation. The clasp 1800 is similar in structure to the clasp 1200, described in detail above. The tube of material 802 has an inner radius 1804, an inner surface 1801, and an outer surface 1803. Cutting the clasp 1800 from a tube of material 1802 provides a cupped or concave profile when viewed from the end, as shown in FIG. 54. One effect of the concave profile is that the elongated portions of the fixed and moving arms 1810, 1830 increasing their stiffness, without substantially impacting the flexibility of the hinge portion 1820. The concave profile also results in barbs 1844 with sharper points or tips 1846 without a separate sharpening operation—i.e., the barbs are formed with a beveled edge without sharpening. The sharp points 1846 enable improved engagement with the native leaflet tissue. Referring to FIG. 55, the sharp points 1846 are formed during laser cutting because the cutting planes that form first and second sides 1847, 1848 of the barbs 1844 to intersect at the tip 1846, thereby forming a triangular pyramid shape that comes to a point that is not possible when the cutting planes that form the sides of the barb are parallel and do not intersect. Thus, the barbs 1844 of the clasp 1800 have a strong base 1845 and a sharp point 1846 in a single layer of material, without any secondary sharpening operation.

Figure 56:
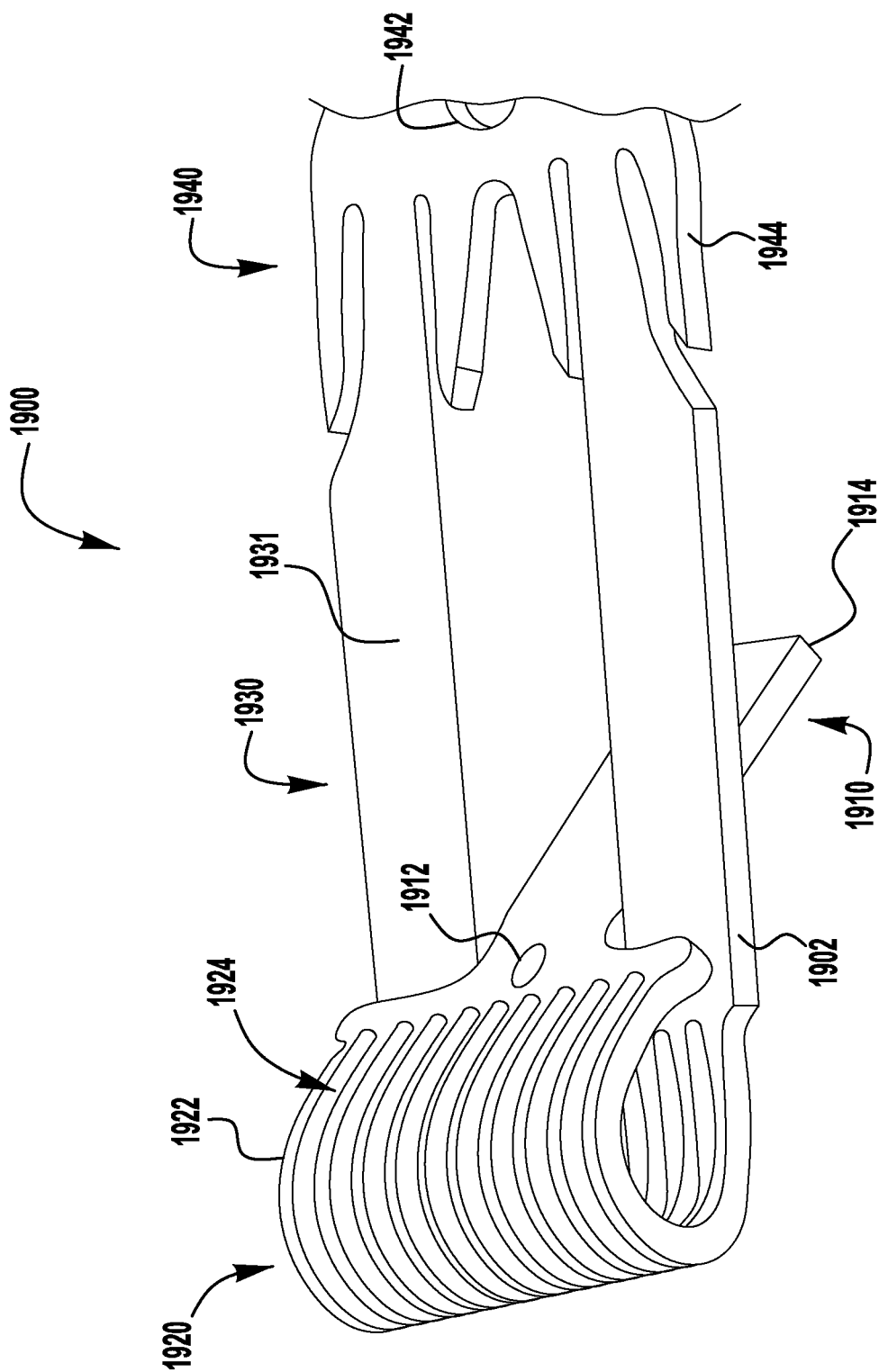
FIG. 56 shows a barbed clasp for an implantable prosthetic device according to an eleventh embodiment.
Figure 56B:
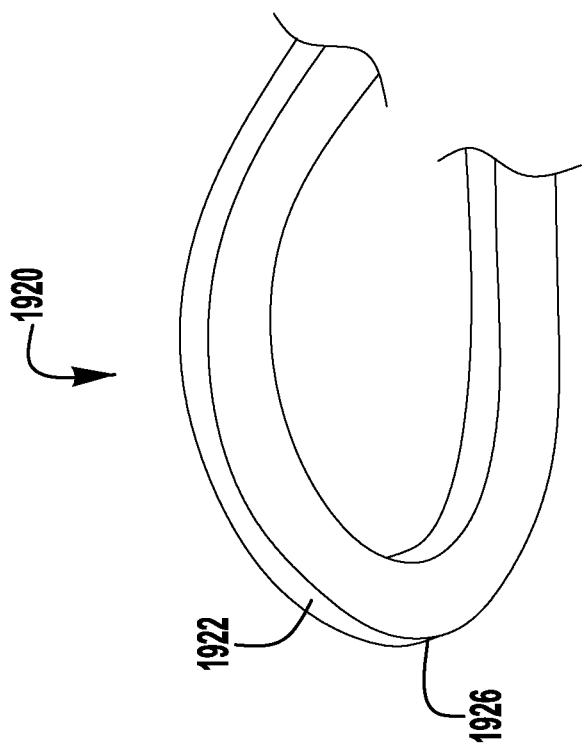
FIGS. 56A-56B show alternate embodiments of hinge portions of the barbed clasp of FIG. 56.
Figure 56A:
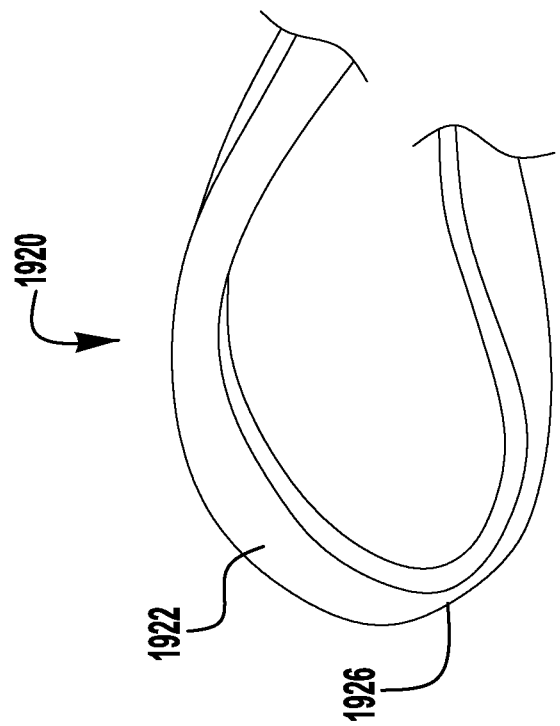

Referring now to FIG. 56, an exemplary clasp 1900 is shown. The clasp 1900 is similar in structure to the clasp 1200, described in detail above with a differently structured hinge portion 1920. The hinge portion 1920 includes a plurality of beams 1922 formed by a series of elongated cuts 1924. Referring now to FIGS. 56A-56B, alternate embodiments of the beams 1922 of the hinge portion 1920 are shown. FIG. 56A shows the rectangular beam 1922 having a bent portion 1926. FIG. 56B shows the rectangular beam 1922 having a bent portion 1926 that is also twisted about 90 degrees such that the cross-section of the beam in the bent portion 1926 is perpendicular to the portions of the beam 1922 at its ends. Twisting the beam 1922, as shown in FIG. 56B, reduces the bending strain in the beam 1922 thereby increasing its flexibility.

Referring now to FIGS. 57-58, an exemplary barbed clasp 2000 for use in implantable prosthetic devices, such as devices 100, 200, 300 described above, is shown. The barbed clasp 2000 includes a fixed arm 2010 that is attached to the implantable device. The barbed clasp 2000 differs from other clasps in that the clasp 2000 includes a plurality of movable arms 2030 that each have a hinged portion 2020 and a barbed portion 2040 having a single barb 2042. The independent arms 2030 of the clasp 2000 individually pinch the tissue of the native leaflet which allows for improved engagement of tissue that is not uniform in thickness. The arms 2030 can also be shape set in a wide or spread out arrangement and crimped down into a narrow configuration for deployment so that the barbs 2042 can be spaced apart laterally more than would be possible if the arms were rigidly connected. In certain embodiments, the arms 2030 include an optional hole or notch (not shown) that can be engaged by an actuation suture to cinch the arms 2030 together during deployment.

The fixed arm 2010 is formed from a tongue 2011 from which beams 2031 that form the moveable arms 2030 extend. The hinge portions 2020 are formed by bending each of the beams 2031 to form a bent portion 2022. The hinged portions 2020 are spring-loaded so that the fixed and moveable arms 2010, 2030 are biased toward each other when the barbed clasp 2000 is in a closed condition. In certain embodiments, the tongue 2011 is formed from a wide plate of material to provide a larger lateral area as a pinching location for the independent arms 2030.

Figure 57A:
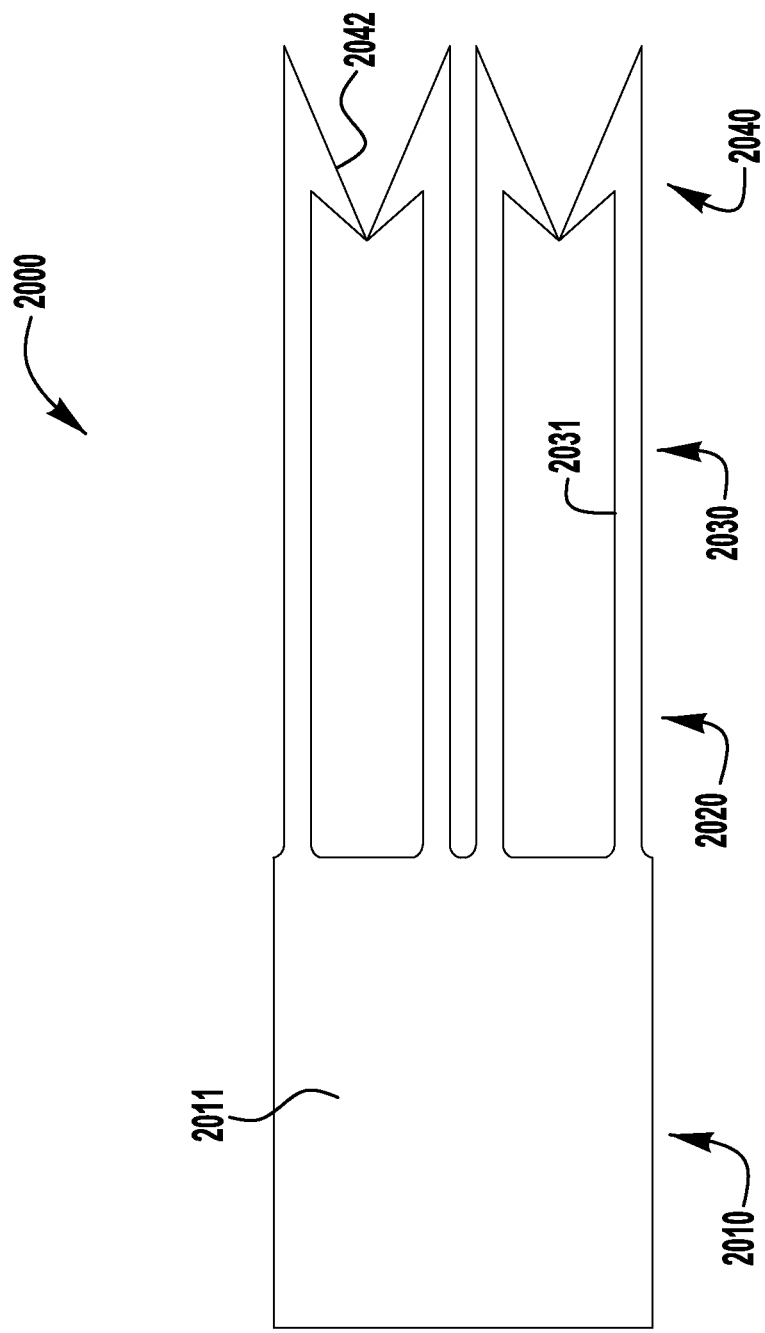
FIG. 57A shows a flat cutout used to make the barbed clasp shown in FIGS. 57 and 58.
Figure 59:
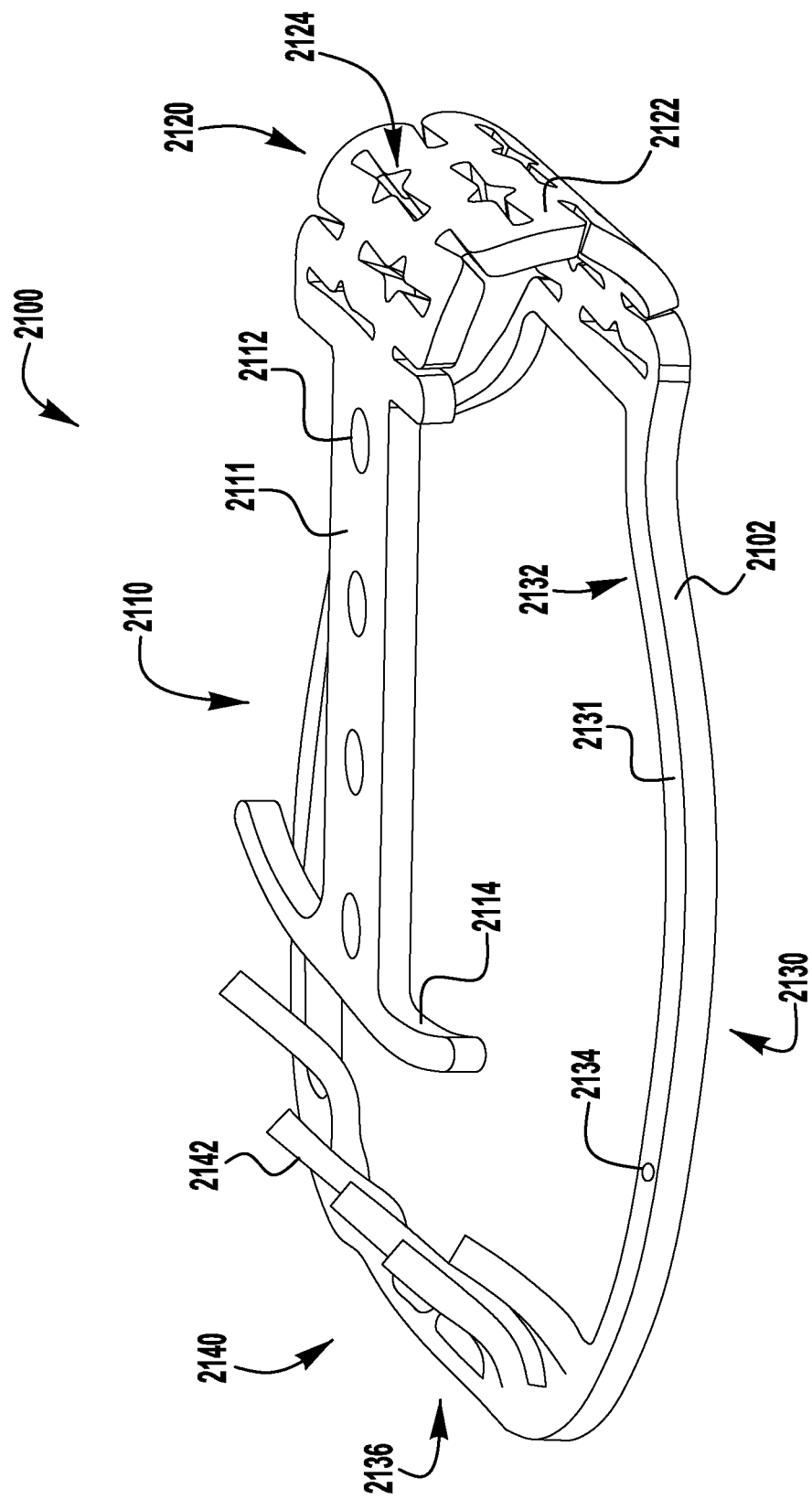
Figure 60:
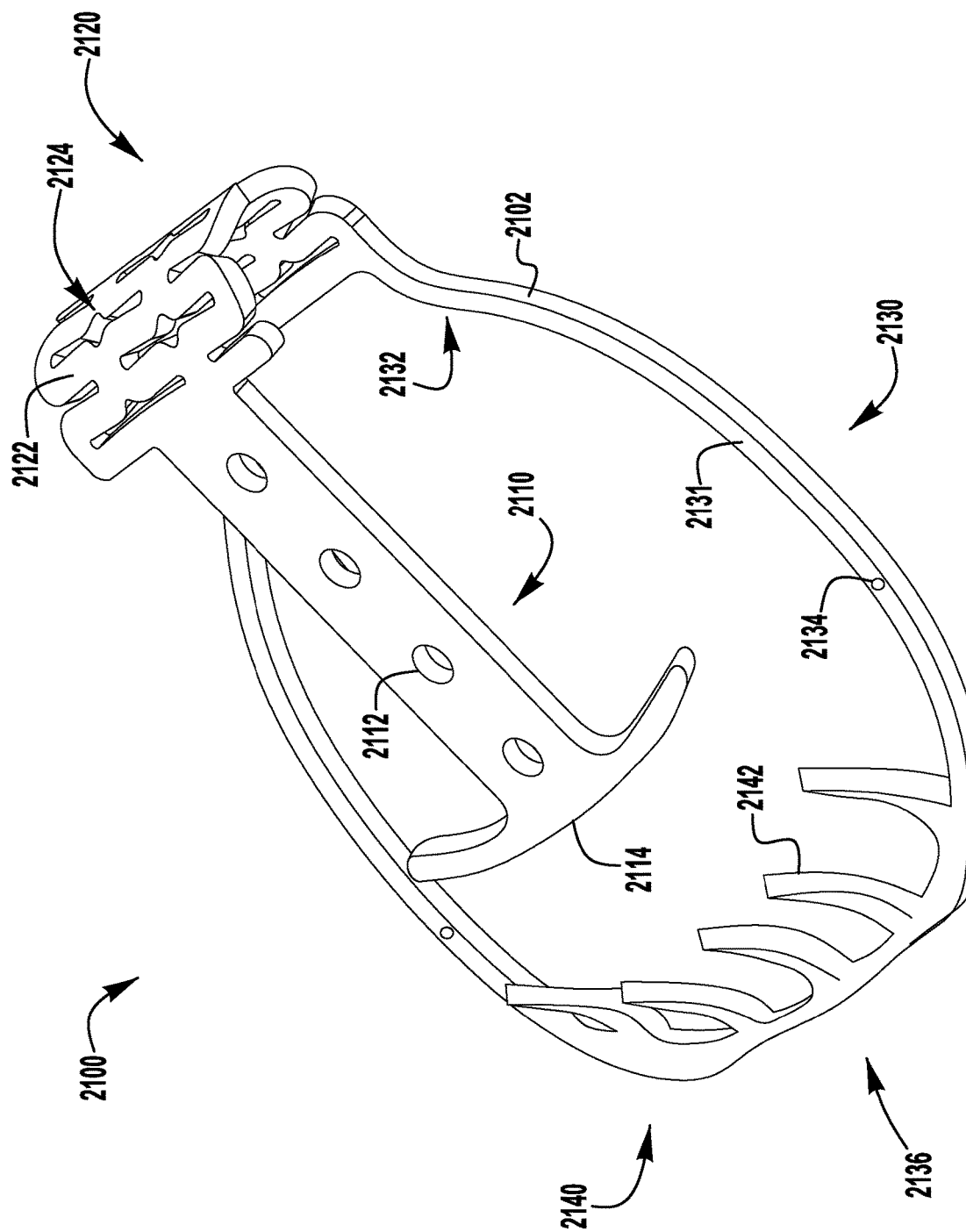

The barbed clasp 2000 is laser cut from a layer 2002 of shape-memory alloy, such as Nitinol. As is shown in FIG. 57A, the barbs 2042 lay flat in the same plane as the rest of the clasp 2000 when cut out of the layer 2002 of material. The moveable arms 2030 and barbs 2040 are then bent and twisted into the shape shown in FIG. 57 and are then subjected to a shape setting process. As noted above, the independent arms 2030 of the clasp 2000 can be shape set as wide or narrow as desired. In certain embodiments individual arms 2030 may be longer or shorter than others, and the spacing of the arms 2030 may vary or be uniform.

Cutting the barbs 2042 out of the sheet of material and then twisting them into position also allows larger barbs of a variety of shapes to be formed. In certain embodiments, the barbed portions 2040 may include multiple smaller barbs arranged in series that may or may not be facing in the same direction. In certain embodiments, the ends of the barbs 2042 are further sharpened using any suitable sharpening means. In certain embodiments, the hinge portions 2020 of the beams 2031 include twisted portions 2024. The twisted portions 2024 may act as torsional springs that resist lateral forces applied to the ends of the barbs 2042, thereby helping to maintain the alignment of the barbs 2042 when engaging the tissue of the native leaflets.

Figure 61:
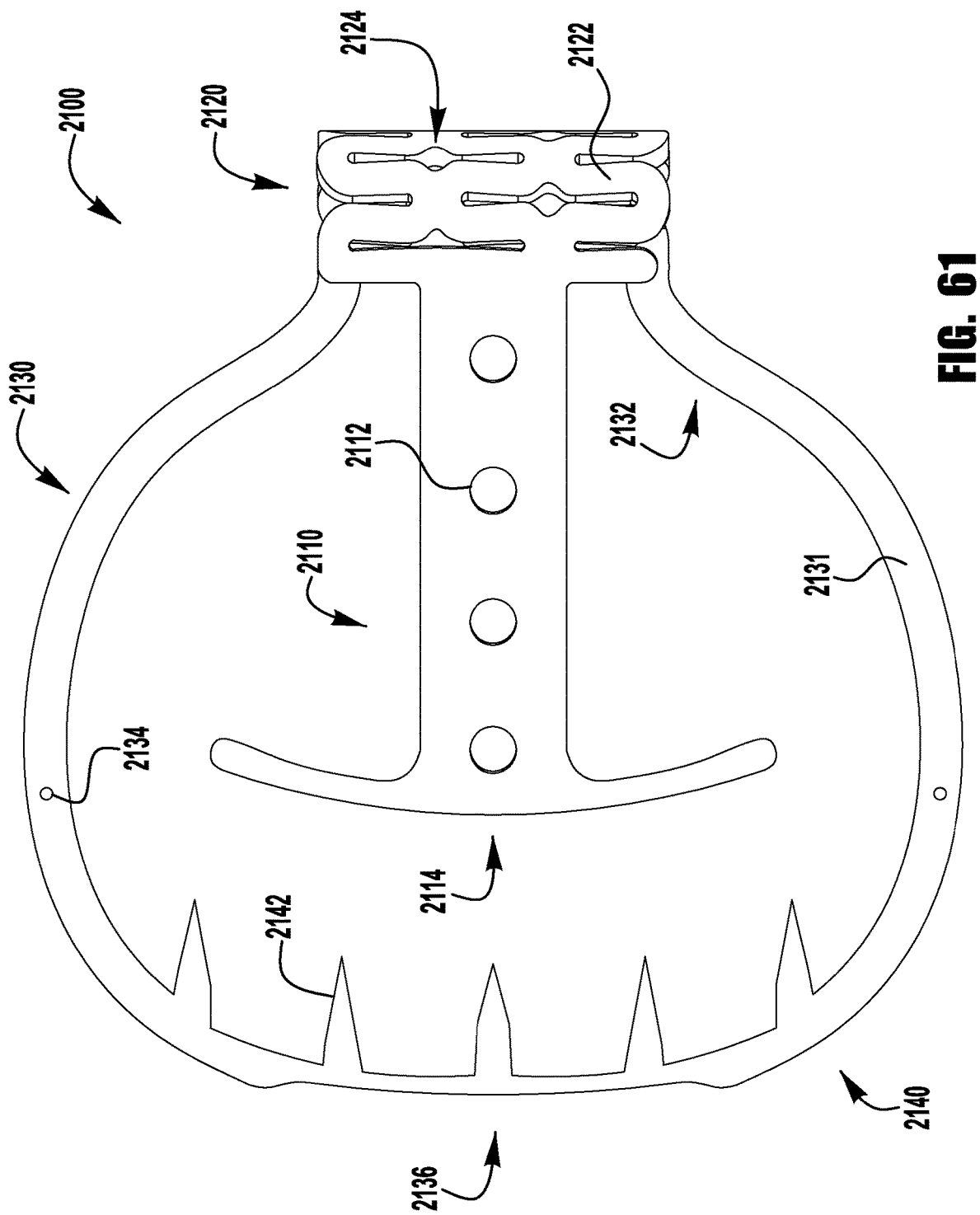
Figure 61A:
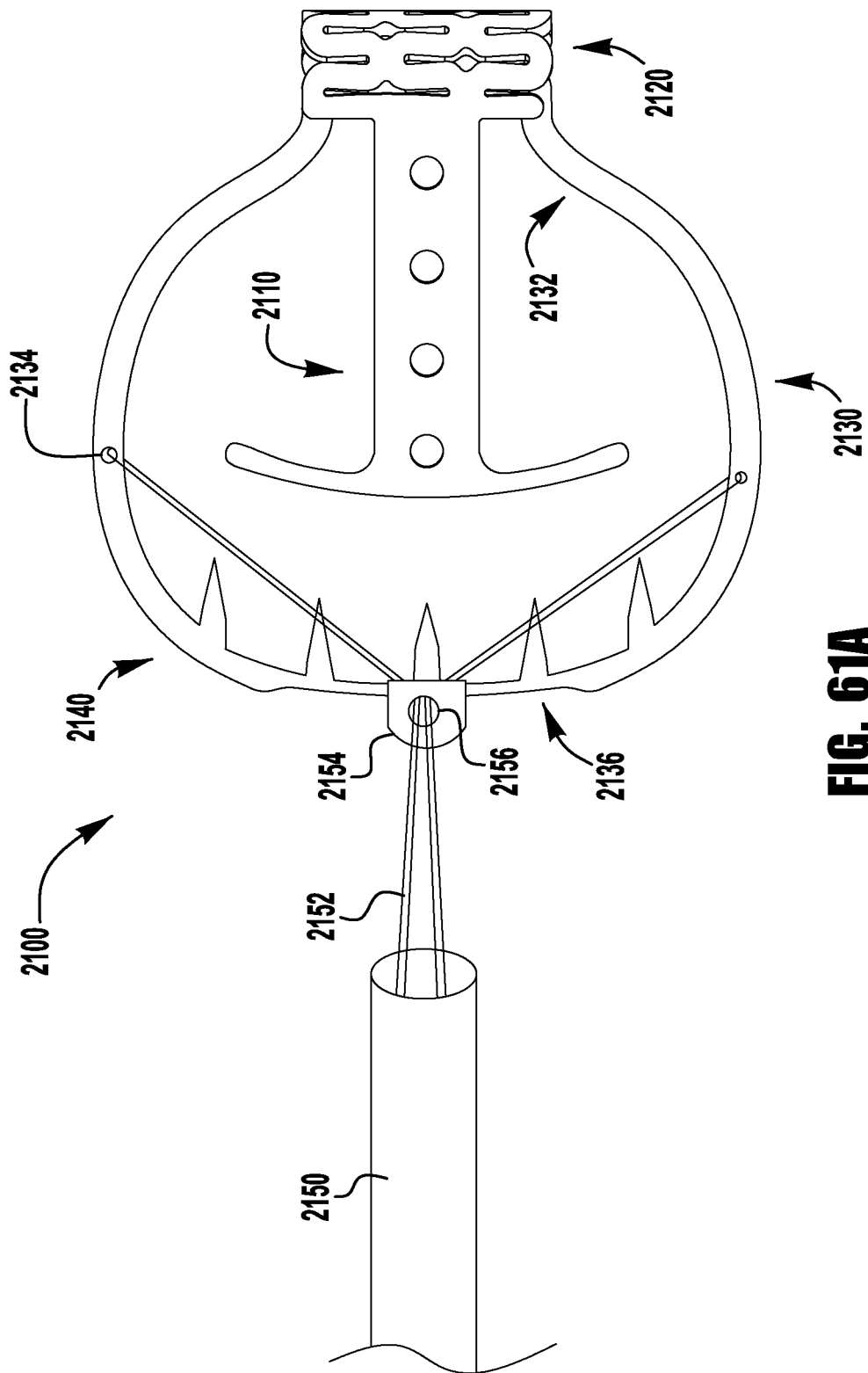
Figure 64:
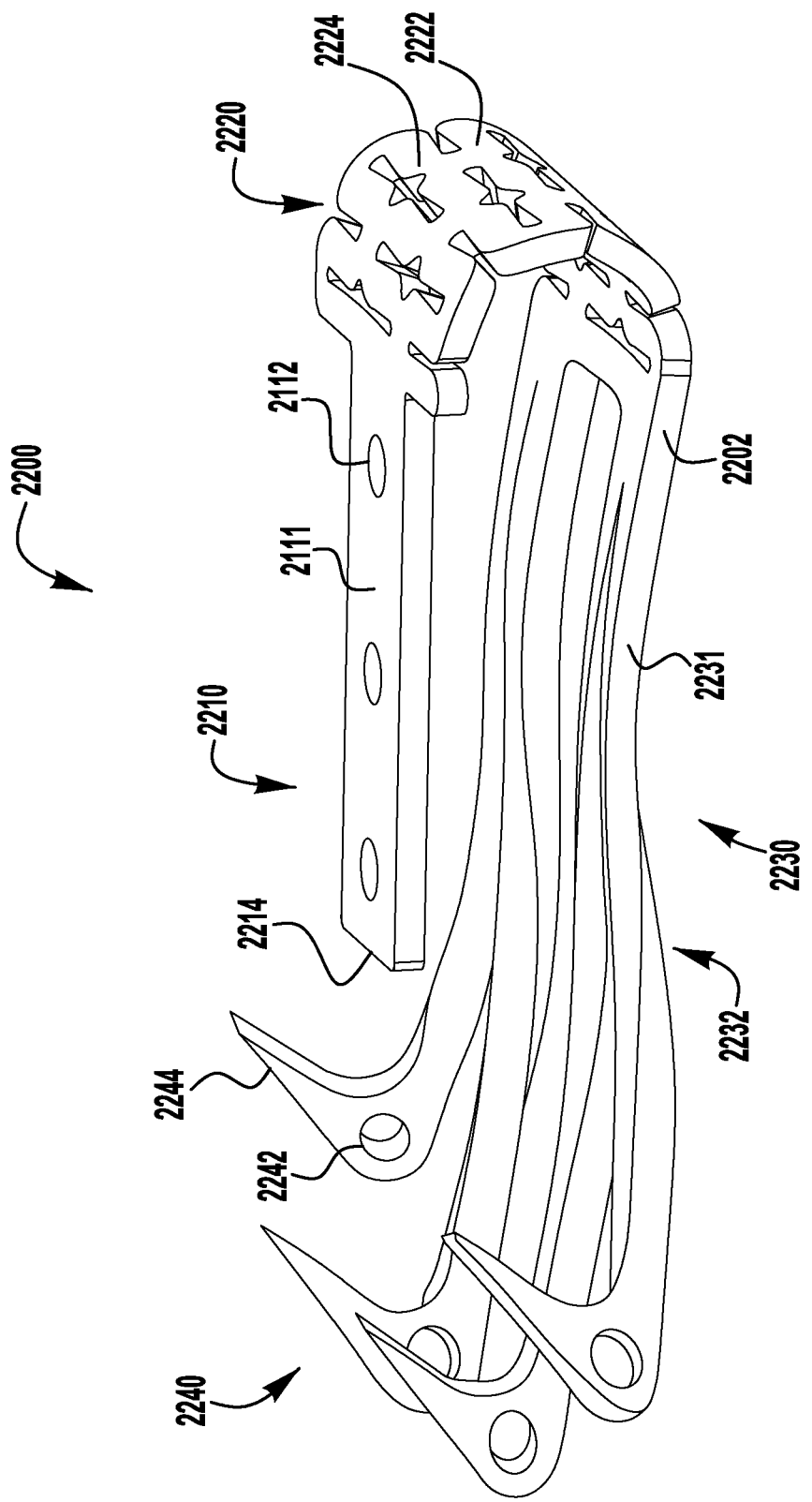
FIGS. 64-68 show a barbed clasp for an implantable prosthetic device according to a fourteenth embodiment.

Referring now to FIGS. 59-63, an exemplary clasp 2100 for use in implantable prosthetic devices, such as devices 100, 200, 300 described above, is shown. The clasp 2100 is expandable between a collapsed condition and an expanded condition and is shape set in the expanded condition so that the clasp 2100 automatically expands from the collapsed condition to the expanded condition. As can be seen in FIG. 61A, the clasp 2100 can be deployed from a delivery sheath 2150 in the collapsed condition and allowed to self-expand into the expanded condition.

The clasp 2100 has many features that are similar to the clasp 1200, described in detail above, such as a patterned hinge portion 2120 formed by a plurality of spring segments 2122 and cutouts 2124 and a fixed arm 2110 that includes a tongue 2111 having holes 2112 for attaching the fixed arm 2110 to the implantable device and an end 2114 having a T-shape to retain the fixed arm 2110 in a p reloaded position. The clasp 2100 also has a moveable arm 2130 that includes a barbed portion 2140 with a plurality of barbs 2142.

The hoop-like shape of the moveable arm 2130 provides for a wider barbed portion 2140 that can include more barbs 2142 with the same or greater lateral spacing than other clasps. The wider spacing of the barbs 2142 improves capture of the native leaflets. In certain embodiments, the hoop shape of the moveable arm 2130 is similar to the shape of wide outer paddles of an implantable device so that pinching forces of the paddles are spread out evenly on the barbs, further improving the retention of the native leaflets. Some of the barbs 2142 may also be longitudinally staggered as a result of their position on the hoop-like shape of the moveable arm 2130. In certain embodiments, the ends of the barbs 2042 are further sharpened using any suitable sharpening means. In certain embodiments, the tongue 2111 is formed from a wide plate of material to provide a larger lateral area as a pinching location.

The moveable arm 2130 is provided in the shape of a hoop or loop. The moveable arm 2130 includes side beams 2131 that are thinner and more flexible, particularly in the lateral direction, than the side beams 1231 of the clasp 1200 described above. The side beams 2131 include a first hinge portion 2132 arranged toward the proximate end of the moveable arm 2130 and a second hinge portion 2136 arranged at the distal end of the moveable arm 2130. The first hinge portion 2132 is formed by one or more bends in the side beams 2132. In certain embodiments, the second hinge portion 2136 includes a thinner—and therefore more flexible—portion to reduce the force required to collapse the clasp 2100. The moveable arm 2130 includes holes 2134 arranged between the first and second hinge portions 2132, 2136 for receiving the actuation sutures 2152 that are used to collapse the moveable arm 2130. The holes 2134 are arranged further laterally from the center of the clasp 2130 than the hinge portions 2132, 2136 to provide mechanical advantage when force is applied via the sutures 2152. In certain embodiments, the holes 2134 are located at the lateral-most location of the side beams 2131.

The rounded hoop shape of the clasp 2100 allows the clasp 2100 to be collapse by merely retracting the clasp 2100 into the delivery sheath. In certain embodiments, the expansion and contraction of the clasp 2100 is controlled by actuation sutures 2152. The sutures 2152 may be routed through an aperture 2156 of a guide 2154 to holes 2134 in the moveable arm 2130 to control the direction in which the force applied along the suture 2152 is applied to cinch the moveable arm 2130 into a collapsed position. For example, arranging the guide 2154 closer to the connection point to the sutures 2152 to the clasp 2100 causes the forces applied to the clasp 2100 by the sutures 2152 to be directed in a more lateral rather than longitudinal direction. Alternatively, as can be seen in FIG. 61B, a single suture loop 2153 can be routed through the aperture 2156 of the guide 2154, through each of the holes 2134 in the moveable arm 2130, and then back through the guide 2154 so that actuation of the single loop 2153 cinches the moveable arm 2130 into a collapsed position.

Referring now to FIGS. 64-68, an exemplary barbed clasp 2200 for use in implantable prosthetic devices, such as devices 100, 200, 300 described above, is shown. The barbed clasp 2200 includes elements of clasps 1200, 2000 described above. The barbed clasp 2200 includes a fixed arm 2210 that is attached to the implantable device and a hinge portion 2220 that allows the clasp 2200 to open and close. The hinge portion 2220 is formed from a repeating pattern of spring segments 2222 and cutouts 2224, like that of the clasp 1200.

Figure 65:
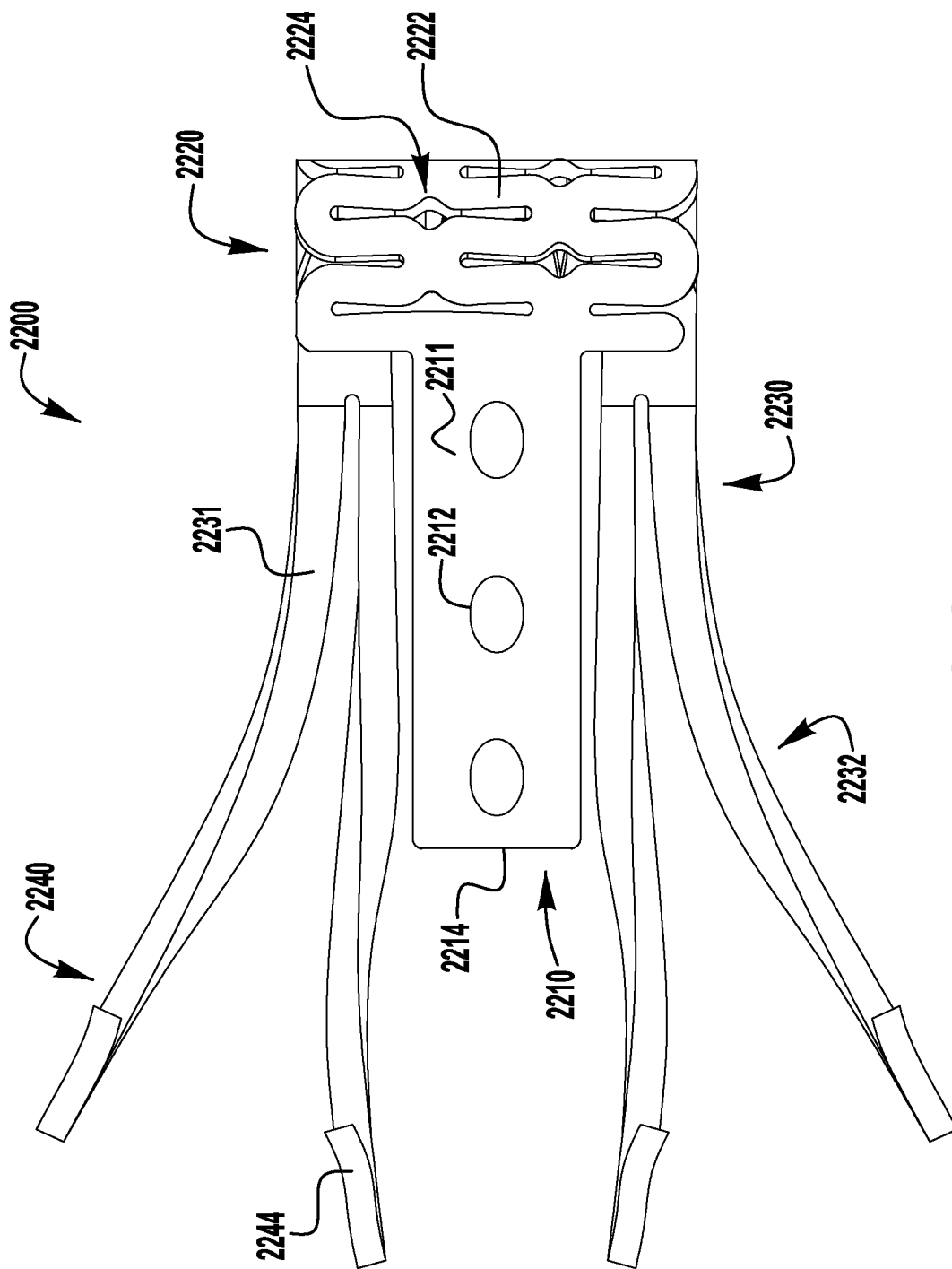
Figure 65A:
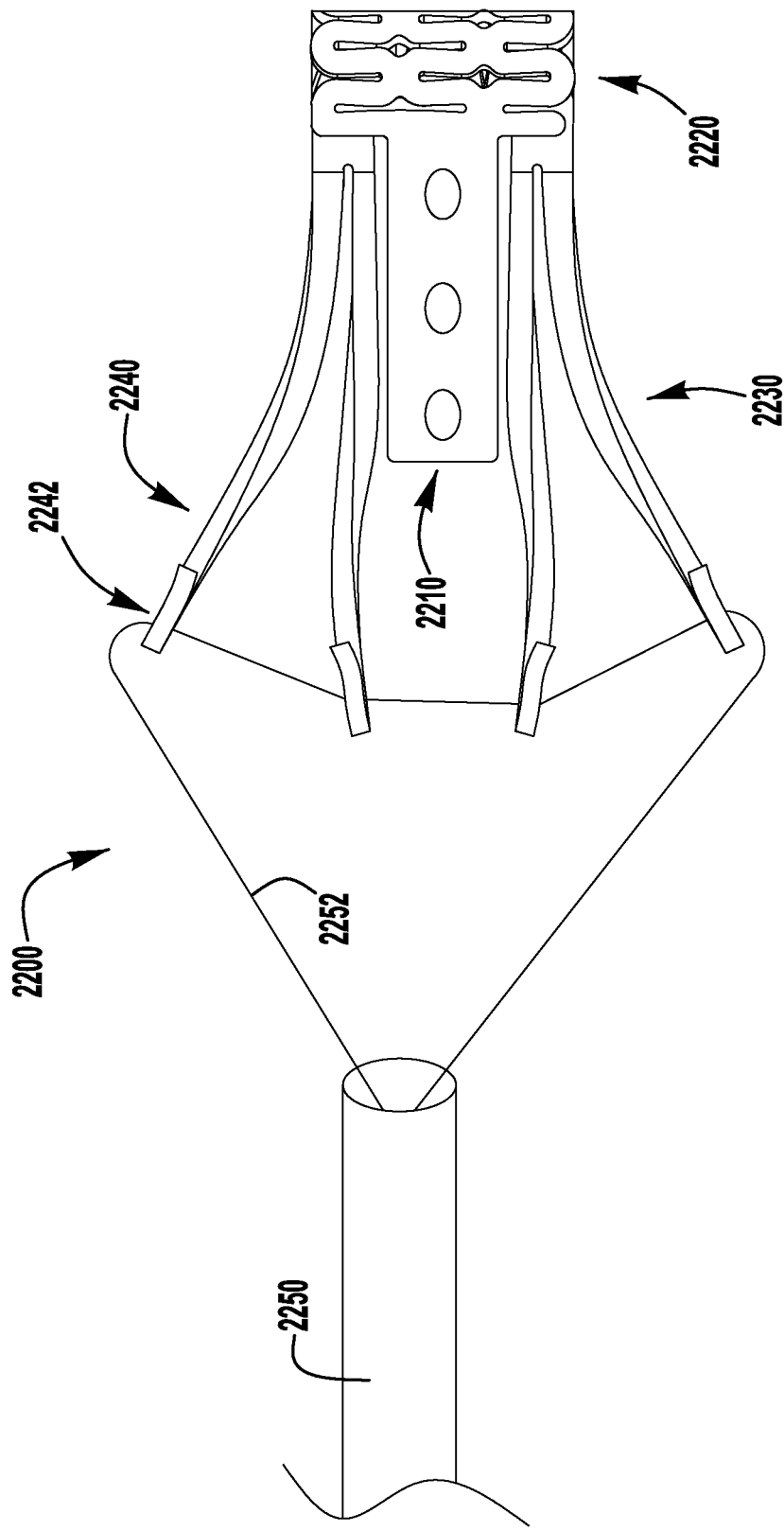
Figure 66:
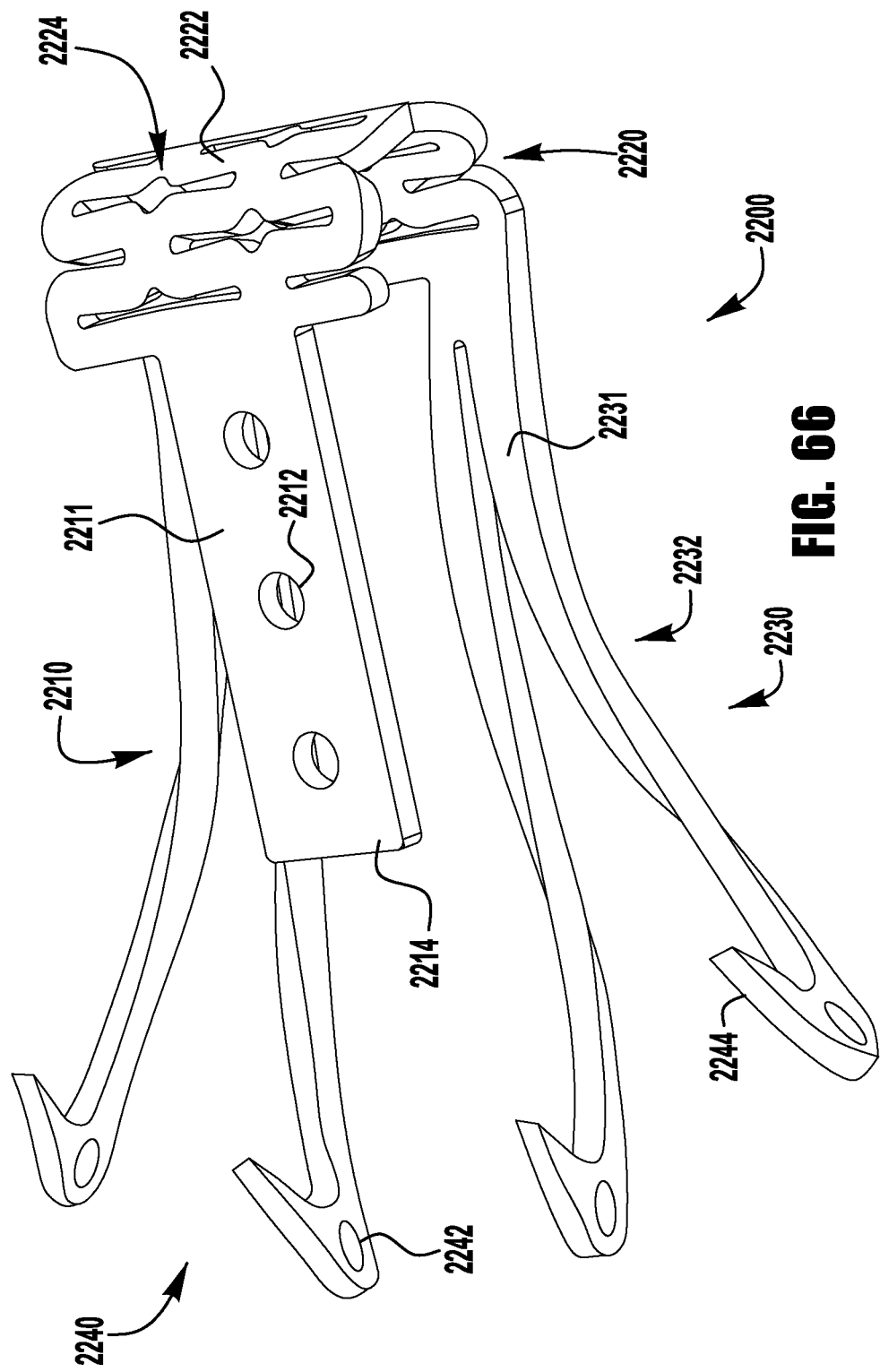
Figure 67:
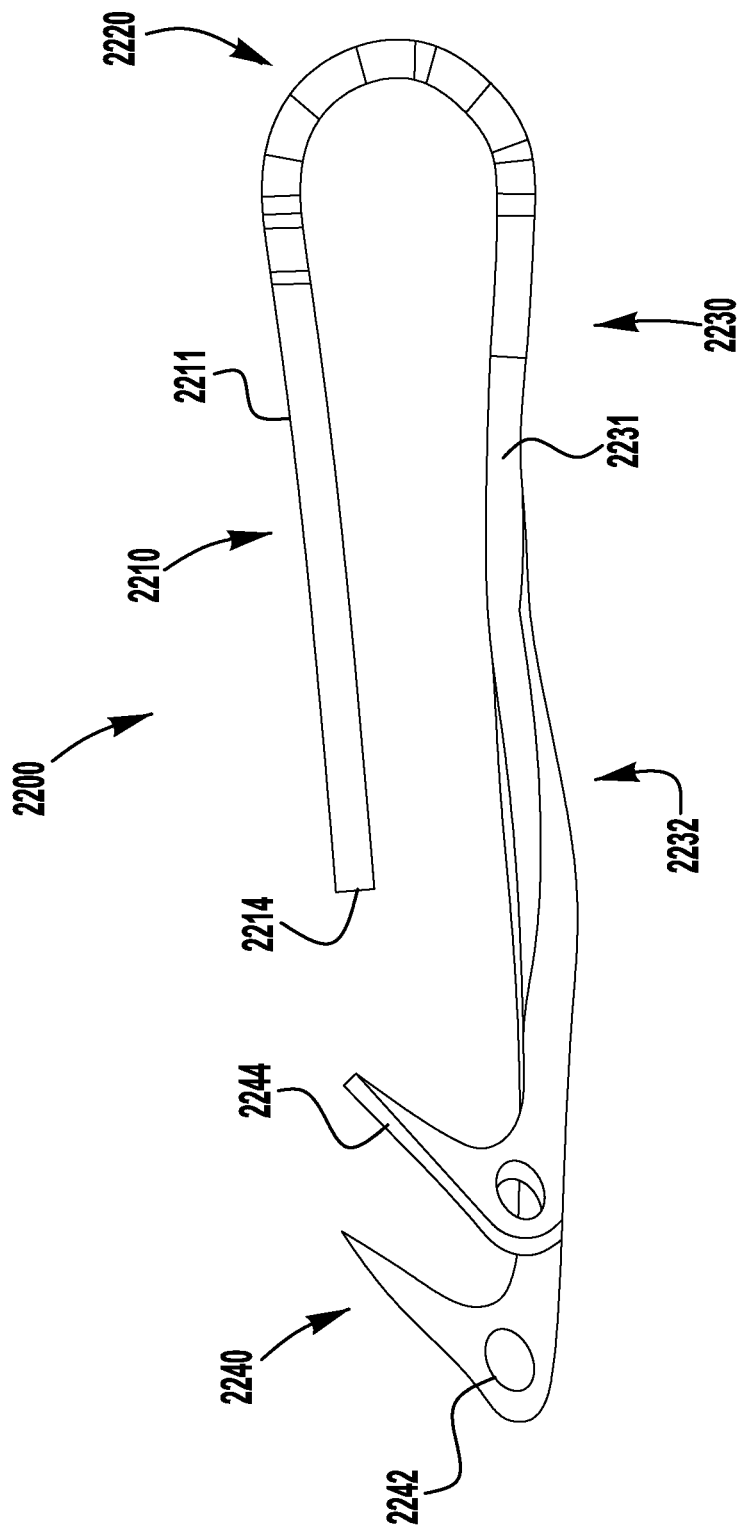
Figure 68:
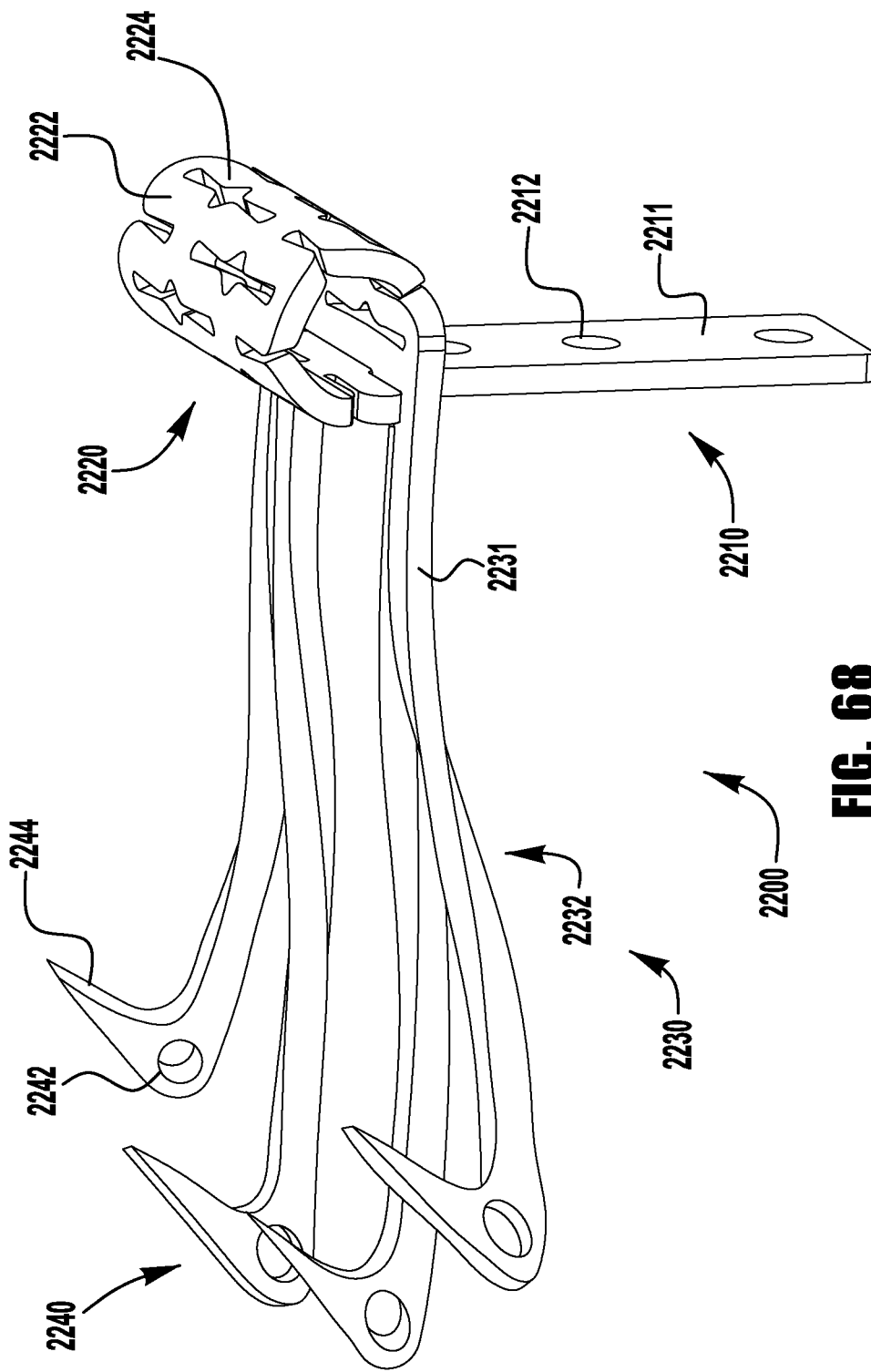

The barbed clasp 2200 also includes features similar to the clasp 2000, such as a plurality of independent movable arms 2230 that each have a barbed portion 2240 having a single barb 2244. The independent arms 2230 of the clasp 2200 individually pinch the tissue of the native leaflet which allows for improved engagement of tissue that is not uniform in thickness. The arms 2230 can also be shape set in a wide or spread out arrangement and crimped down into a narrow configuration for deployment so that the barbs 2244 can be spaced apart laterally more than would be possible if the arms were rigidly connected. The barbed portion 2240 of each arm 2230 includes a hole 2242 for receiving an actuation suture 2252 (FIG. 65A).

The clasp 2200 is expandable between a collapsed condition and an expanded condition and is shape set in the expanded condition so that the clasp 2200 automatically expands from the collapsed condition to the expanded condition. As can be seen in FIG. 65A, the clasp 2200 can be deployed from a delivery sheath 2250 in the collapsed condition and allowed to self-expand into the expanded condition. The expansion and contraction of the clasp 2200 is controlled by the actuation suture 2252 that cinches the independent arms 2230 together to collapse the clasp 2200 so that it fits within the delivery sheath 2250. In some embodiments, the independent arms collapse together by merely retracting the clasp 2100 into the delivery sheath.

The fixed arm 2210 is formed from a tongue 2211 extending from the hinge portion 2220 to an end 2214. The tongue 2211 includes holes 2212 for securing the tongue 2211 to the implantable device. In certain embodiments, the tongue 2211 is formed from a wide plate of material to provide a larger lateral area as a pinching location. In certain embodiments, the end 2214 of the tongue 2211 includes a T-shape cross-member like that of clasp 2100.

The barbed clasp 2200 is laser cut from a layer 2202 of shape-memory alloy, such as Nitinol. Like the clasp 2100 shown in FIG. 57A, the barbs 2242 lay flat in the same plane as the rest of the clasp 2200 when cut out of the layer 2202 of material. The moveable arms 2230 and barbed portions 2240 are then bent and twisted into the shape shown in FIGS. 64-68 and are then subjected to a shape setting process. In some embodiments, the barbs of the independent arms are [?] cut so that the barbs are bent upwards like the barbs of clasp 1200, thereby not requiring the twisting of the independent arms. As noted above, the independent arms 2230 of the clasp 2200 can be shape set as wide or narrow as desired. In certain embodiments, individual arms 2230 may be longer or shorter than others, and the spacing of the arms 2230 may vary or be uniform.

Cutting the barbs 2244 out of the sheet of material and then twisting them into position also allows larger barbs of a variety of shapes to be formed. In certain embodiments, the barbed portions 2240 may include multiple smaller barbs arranged in series that may or may not be facing in the same direction. In certain embodiments, the ends of the barbs 2244 are further sharpened using any suitable sharpening means. In certain embodiments, the beams 2231 include twisted portions 2232. The twisted portions 2232 may act as torsional springs that resist lateral forces applied to the ends of the barbs 2244, thereby helping to maintain the alignment of the barbs 2244 when engaging the tissue of the native leaflets.

Referring now to FIGS. 69-73B, various arrangements for attaching an actuating suture to exemplary barb clasps are shown. In these embodiments, an intermediate suture loop is made through one or more of the eyelets in the barbed clasp and the actuation suture is inserted through one or more of the intermediate loops. Connecting to the clasp through an intermediate loop of suture material reduces friction experienced by the actuation suture relative to the friction between the actuation suture and the clasp material. Both ends of the actuation suture extend back into and through the delivery sheath (not shown). The suture can be removed by pulling one end of the suture proximally until the other end of the suture pulls through the eyelet or intermediate loop and back into the delivery sheath.

Figure 69:
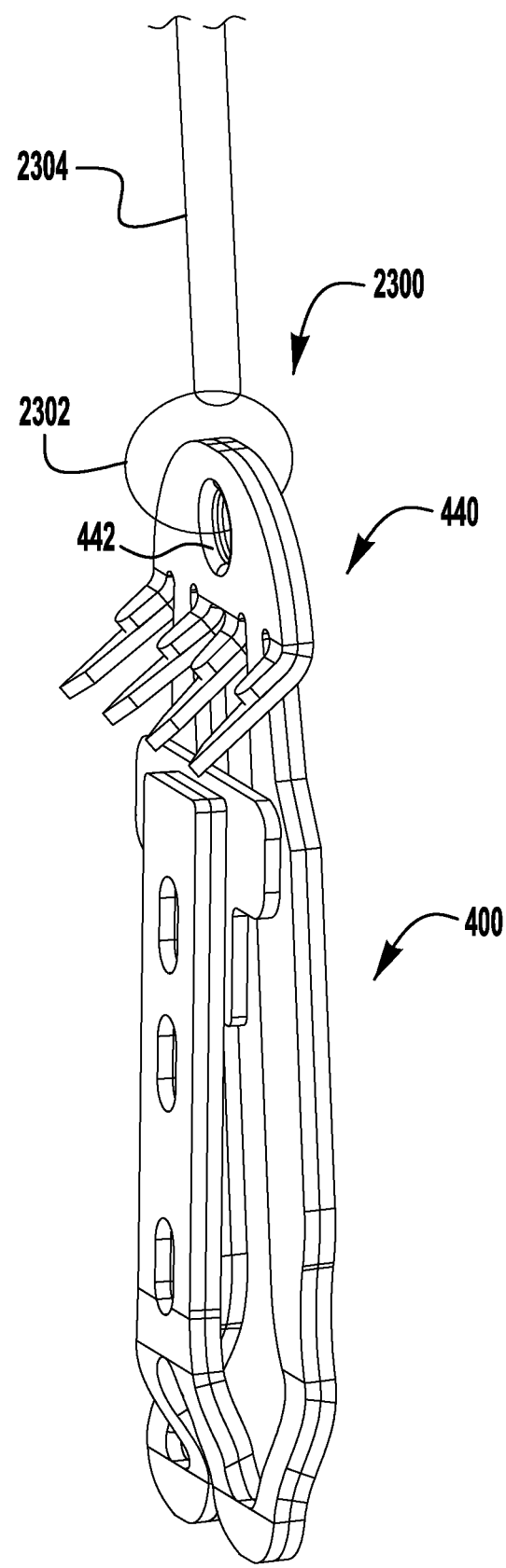

Referring now to FIG. 69, an exemplary suture arrangement 2300 is shown attached to the barb clasp 400 described above. The suture arrangement 2300 includes an intermediate suture loop 2302 inserted through the eyelet 442 and around the end of the barbed portion 440. Alternatively, the intermediate suture loop 2302 may be inserted through the eyelet 442 and between the side beams of the moveable arm. An actuation suture 2304 is threaded from the delivery sheath through the intermediate suture loop 2302 and back into the delivery sheath. Tension applied to the actuation suture 2304 opens the clasp 400 when the spring forces keeping the clasp 400 closed are overcome. Releasing tension on the actuation suture 2304 allows the clasp 400 to spring shut. The rounded shape of the barbed portion 440 of the clasp 400 prohibits the clasp 400 from catching on native tissue or other portions of the implantable device.

Referring now to FIGS. 70A-70B, an exemplary suture arrangement 2400 is shown attached to the barb clasp 1200 described above. The suture arrangement 2400 includes an intermediate suture loop 2402 inserted through the center eyelet 1242 and between the side beams 1231 of the moveable arm 1230. An actuation suture 2404 is threaded from the delivery sheath through the intermediate suture loop 2402 and back into the delivery sheath. Tension applied to the actuation suture 2404 opens the clasp 1200 when the spring forces keeping the clasp 1200 closed are overcome. Releasing tension on the actuation suture 2404 allows the clasp 1200 to spring shut.

FIG. 70A is a side view of the suture arrangement 2400 showing that a gap or recess 2406 may form between the end of the clasp and the actuating suture 2404 of the suture arrangement 2400 described above. In particular, the gap 2406 may form when the actuation suture 2404 is at an angle with the barbed portion of the clasp 1200. FIG. 70B is a front view of the suture arrangement 2400 showing that side gaps or recesses 2408 are formed between the actuation suture 2404 and the sides of the barbed portion 1240 of the clasp 1200. Under certain conditions, the gaps or recesses 2406, 2408 may become catch points—i.e., a location that has a potential to catch or snag native tissue or other portions of the implantable device during deployment and installation and/or on a catheter wall during retrieval. In particular, sharp angles and edges may become catch points. Rounding the corners of the clasp 1200, as can be seen in FIG. 70B, reduces the chance that the clasp 1200 will catch. In some embodiments, the device does not include any recesses having a depth greater than one third of the width of the device.

Referring now to FIG. 71, a front view of an exemplary suture arrangement 2500 is shown attached to the barb clasp 1200 described above. The suture arrangement 2500 includes an intermediate suture loop 2502 inserted through the center eyelet 1242 and around the end of the barbed portion 1240. An actuation suture 2504 is threaded from the delivery sheath through the intermediate suture loop 2502 and back into the delivery sheath. Tension applied to the actuation suture 2504 opens the clasp 1200 when the spring forces keeping the clasp 1200 closed are overcome. Releasing tension on the actuation suture 2504 allows the clasp 1200 to spring shut.

Forming the intermediate suture loop 2502 around the end of the barbed portion 1240 eliminates the possibility that a gap (e.g., the gap 2406 shown in FIG. 70A) will form between the actuation suture and the clasp. Like the suture arrangement 2400 described above and shown in FIG. 70B, FIG. 71 shows that side gaps 2508 are formed between the actuation suture 2504 and the sides of the barbed portion 1240 of the clasp 1200. Under certain conditions, the gaps 2508 may become catch points—i.e., a location that has a potential to catch or snag native tissue or other portions of the implantable device during deployment and installation and/or on the catheter during retrieval. In particular, sharp angles and edges may become catch points. Rounding the corners of the clasp 1200, as can be seen in FIG. 71, reduces the chance that the clasp 1200 will catch on native tissue or other portions of the device.

Figure 72:
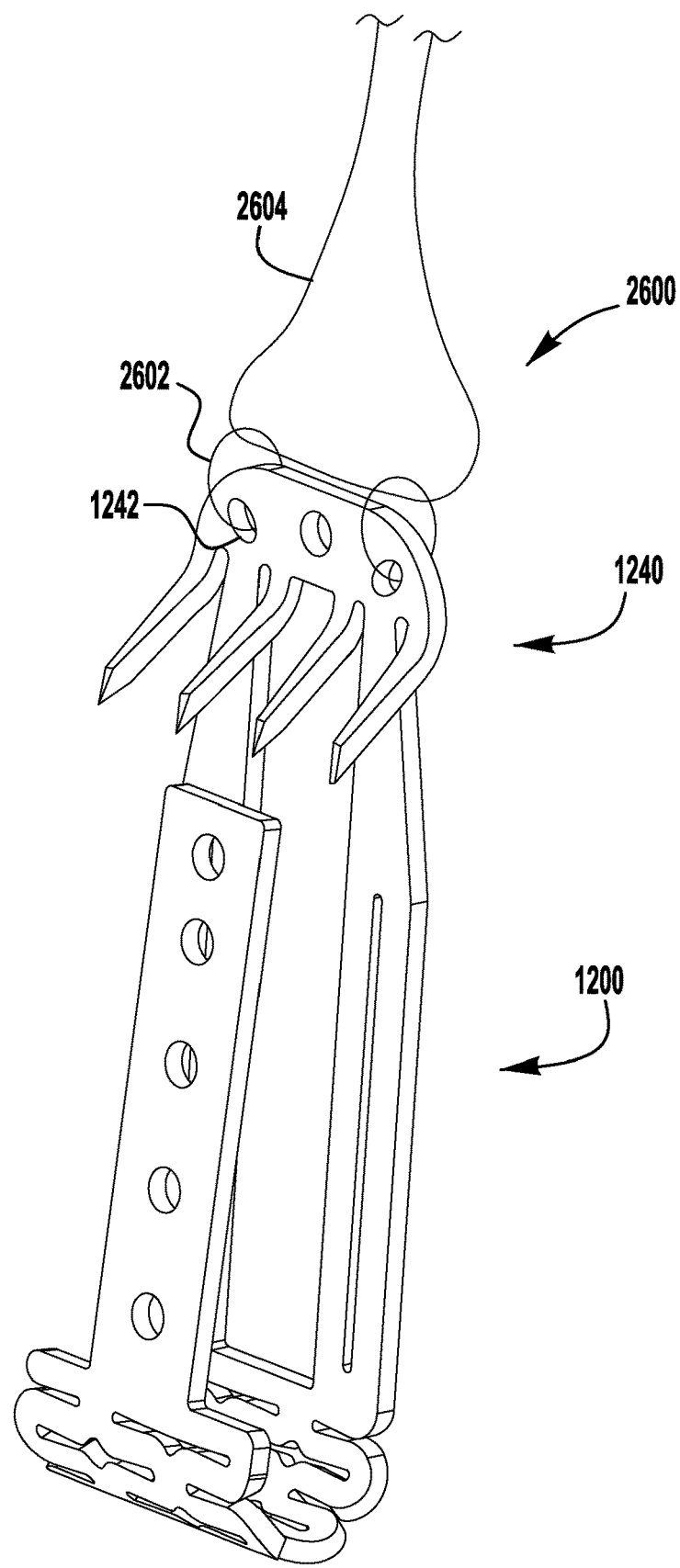
Figure 73B:
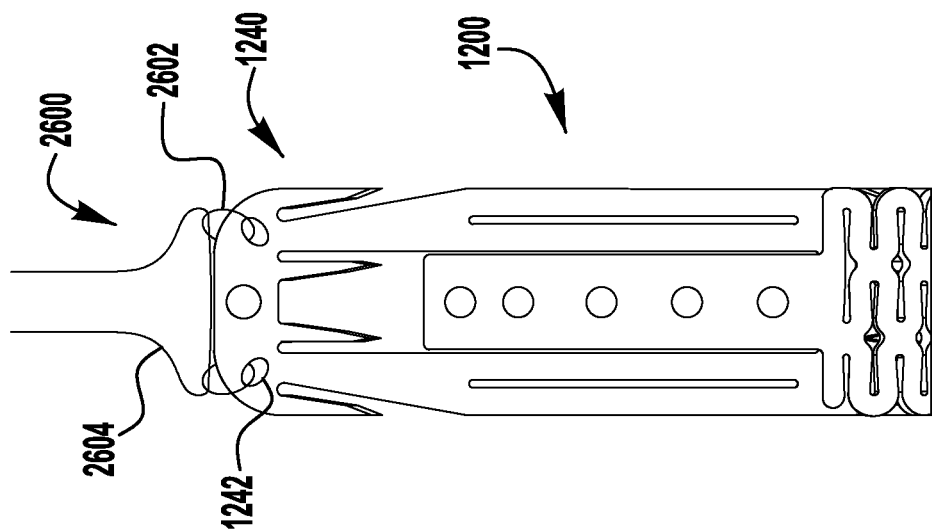
Figure 73A:
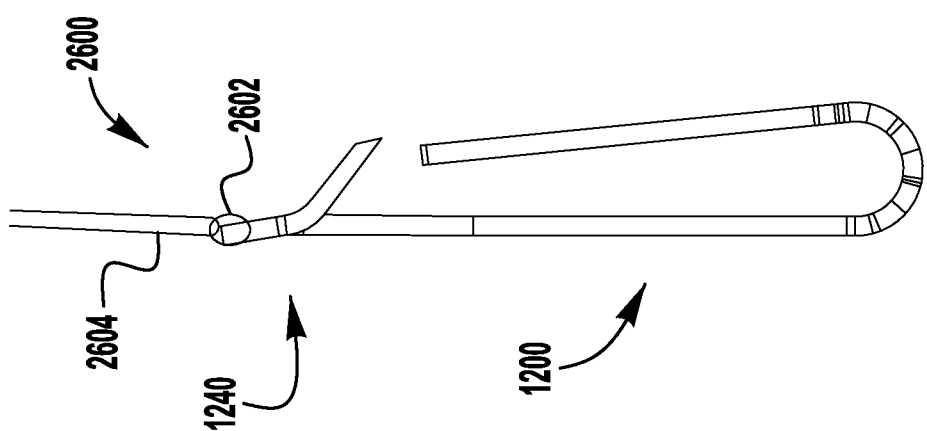

Referring now to FIGS. 72-73B, an exemplary suture arrangement 2600 is shown attached to the barb clasp 1200 described above. The suture arrangement 2600 includes intermediate suture loops 2602 inserted through the eyelets 1242 proximate the sides of the clasp 1200 and around the end of the barbed portion 1240. An actuation suture 2604 is threaded from the delivery sheath through the intermediate suture loops 2602 and back into the delivery sheath. Tension applied to the actuation suture 2604 opens the clasp 1200 when the spring forces keeping the clasp 1200 closed are overcome. Releasing tension on the actuation suture 2604 allows the clasp 1200 to spring shut.

The suture arrangement 2600 reduces or eliminates the gaps shown in FIGS. 70A-71 that can become catch points. Forming the intermediate suture loops 2602 around the end of the barbed portion 1240 eliminates the possibility of a gap, such as the gap 2406 shown in FIG. 70A, from forming between the clasp 1200 and the actuation suture 2604. The suture arrangement 2600 also reduces or eliminates side gaps, such as the side gaps 2508 shown in FIGS. 70B and 71, between the actuation suture 2604 and the sides of the clasp 1200.

Figure 74B:
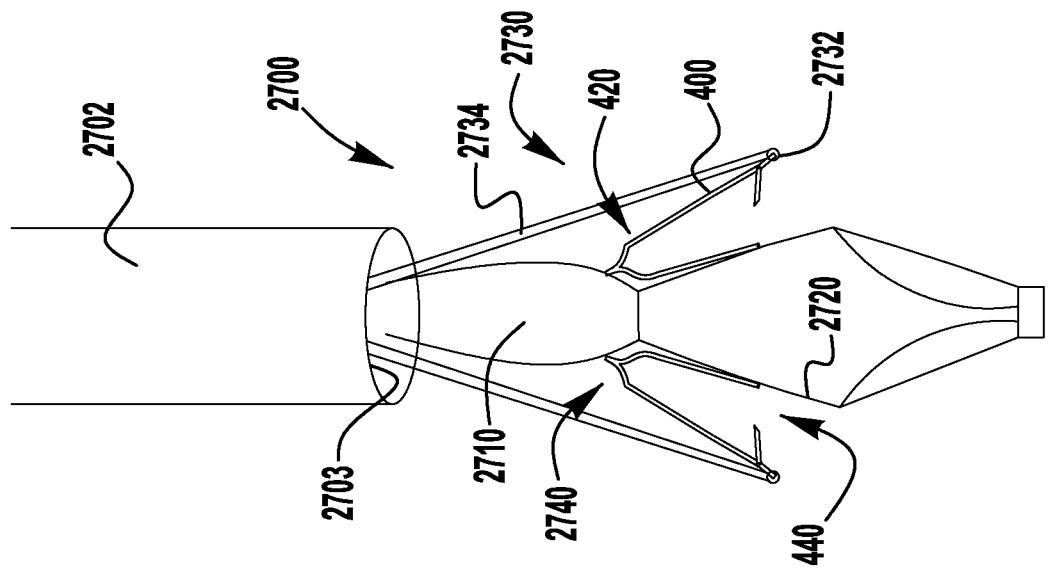
FIGS. 74A-74B show an exemplary barbed clasp being opened with actuating lines.
Figure 74A:
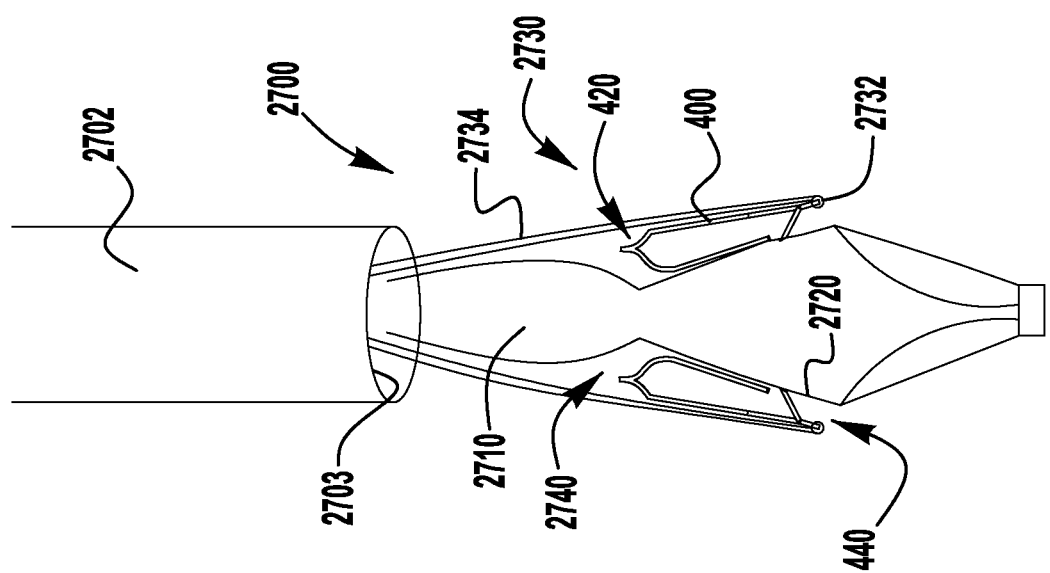
Figure 75:
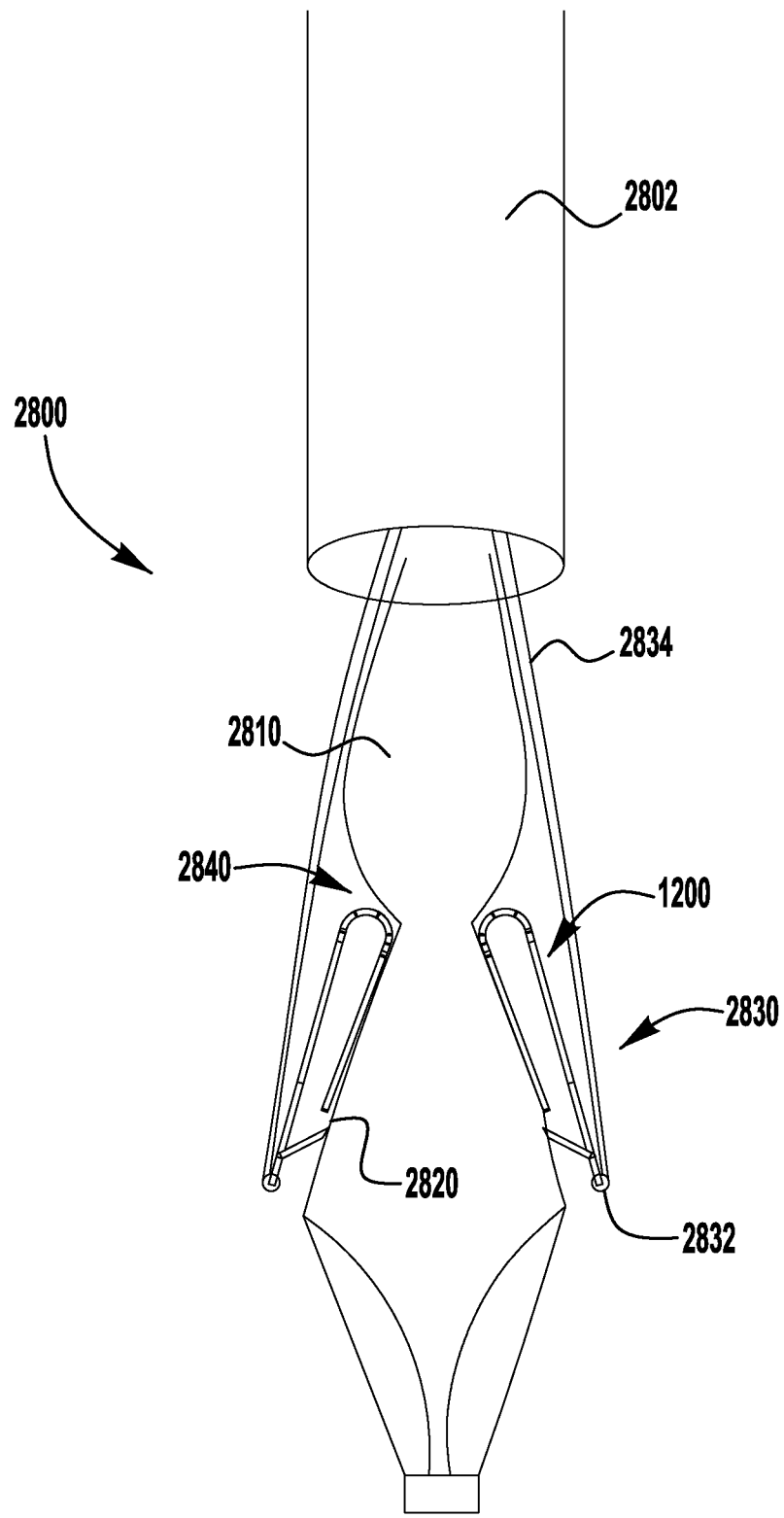
FIG. 75 shows an exemplary barbed clasp of the ninth or tenth embodiments with actuating lines.

Referring now to FIGS. 74A-75, exemplary barb clasps and implantable devices are shown. As noted above, catch points are locations on the implantable device that have a potential to catch or snag native tissue, other portions of the implantable device, and/or delivery catheter during deployment and installation and/or during recapture or retrieval. In addition to catch points that may be formed on individual components of the implantable device, such as the catch points described above, catch points may also be formed by the assembly of two or more components.

Referring now to FIGS. 74A-74B, an exemplary implantable device 2700 is shown assembled with two barb clasps 400. The barb clasps 400 are attached to inner paddles 2720 of the implantable device 2700 that extend from a coaption element 2710. A suture arrangement 2730 includes intermediate suture loops 2732 attached to the barbed portion 440 of the clasps 400, and actuation sutures 2734 extending from a delivery sheath 2702, through the intermediate suture loops 2732, and back into the sheath 2702. When the clasps 400 are in a closed condition, the offset of the hinge portions 420 forms a gap 2740 between the clasps 400 and coaption element 2710 that can become a catch point. As can be seen in FIG. 74B, the gap 2740 is reduced or eliminated when the clasps 400 are opened partially, though the overall width of the device 2700 increases because of the opening of the clasps 400. As such, the catch point can be eliminated during recapture or retrieval by partially opening the clasps 400 as shown in FIG. 74B. Partially opening the clasps when retracting the device into the sheath has an additional benefit of causing the actuation lines or sutures to engage an opening 2703 of the delivery sheath 2702, thereby causing the opening 2703 to flair open and provide a larger opening through which the device 2700 can be withdrawn. Suture configurations like those shown in FIGS. 70B and 71 engage the opening 2703 in two locations as the sutures extend from the clasps in two locations, thereby widening the opening 2703 in a substantially diamond shape. Suture configurations like those shown in FIG. 72 engage the opening 2703 in four locations because the sutures extend from the clasps in four locations, thereby widening the opening 2703 in a substantially rectangular shape. The actuation sutures 2734 can be relaxed after the hinge portions 420 are in the catheter.

Referring now to FIG. 75, an exemplary implantable device 2800 is shown assembled with two barb clasps 1200. The barb clasps 1200 are attached to inner paddles 2820 of the implantable device 2800 that extend from a coaption element 2810. A suture arrangement 2830 includes intermediate suture loops 2832 attached to the barbed portion 1240 of the clasps 1200, and actuation sutures 2834 extending from a delivery sheath 2802, through the intermediate suture loops 2832, and back into the sheath 2802. The round shape of the hinge portion 1220 of the clasp 1200 prevents a catch point from forming at an intersection 2840 between the hinge portion 1220 and the coaption element 2810. Thus, the shape of the clasp 1200 reduces or eliminates gaps, such as the gap 2740 shown in FIG. 74B that may become catch points, without needing to partially open the clasps 1200 during retrieval or recapture.

In certain embodiments, rather than an intermediate suture loop, the actuation line or suture is attached to a portion of a covering surrounding a clasp of an implantable device. For example, the actuation line or suture may be threaded through a loop or openings in the covering. The covering may be formed from a flexible material that may be a mesh, woven, braided, or formed in any other suitable way. The flexible material may be cloth, shape-memory alloy wire—such as Nitinol—to provide shape setting capability, or any other flexible material suitable for implantation in the human body.

Figure 76:
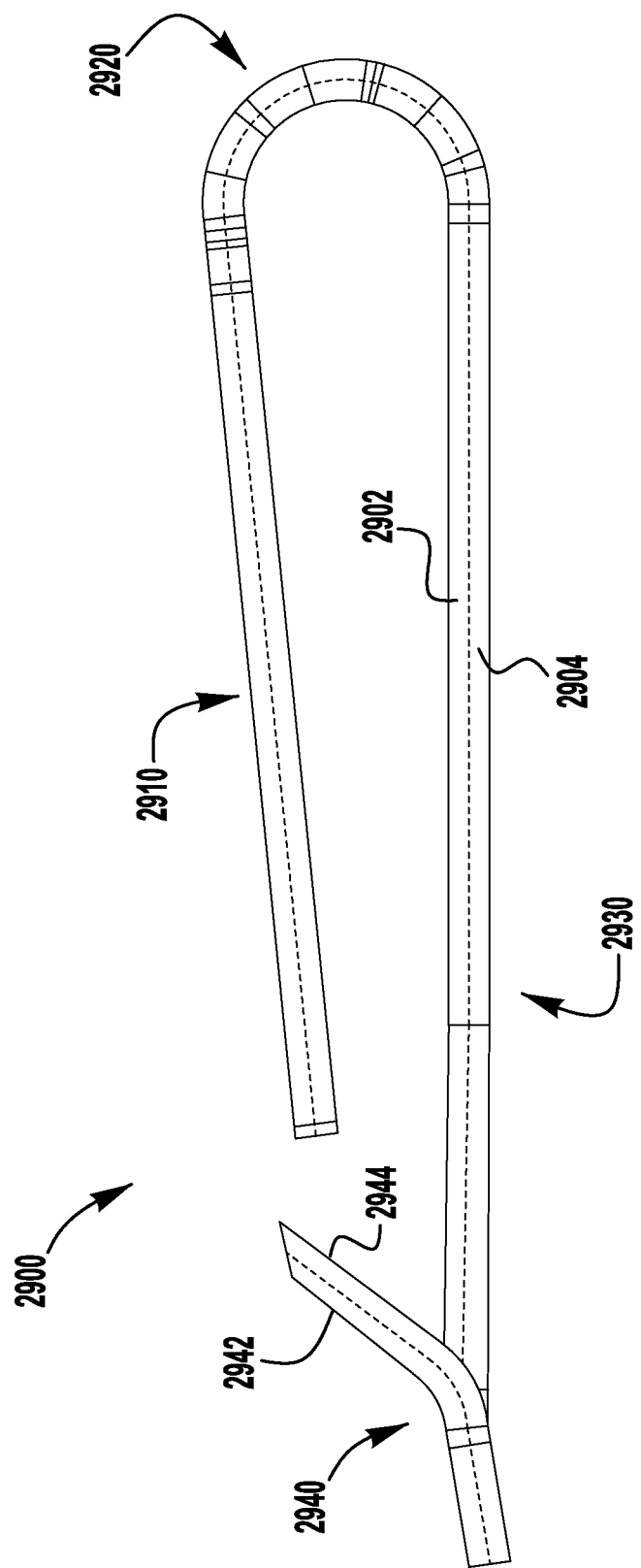
FIG. 76 shows a barbed clasp for an implantable prosthetic device according to a fifteenth embodiment.

Referring now to FIG. 76, a side view of an exemplary barb clasp 2900 is shown. While the clasp 2900 is shown in the shape of the clasp 1200 described above, the clasp 2900 can have any shape suitable for use as a barbed clasp formed from laminated layers of material, such as any of the clasps described above. The clasp 2900 has a fixed arm 2910, hinged portion 2920, moveable arm 2930, and barbed portion 2940. The clasp 2900 is formed from a first layer 2902 and a second layer 2904 of material. The layers 2902, 2904 may be formed from similar or different materials, and may have the same or different thicknesses. In certain embodiments, additional layers of material may also be provided.

Figure 77:
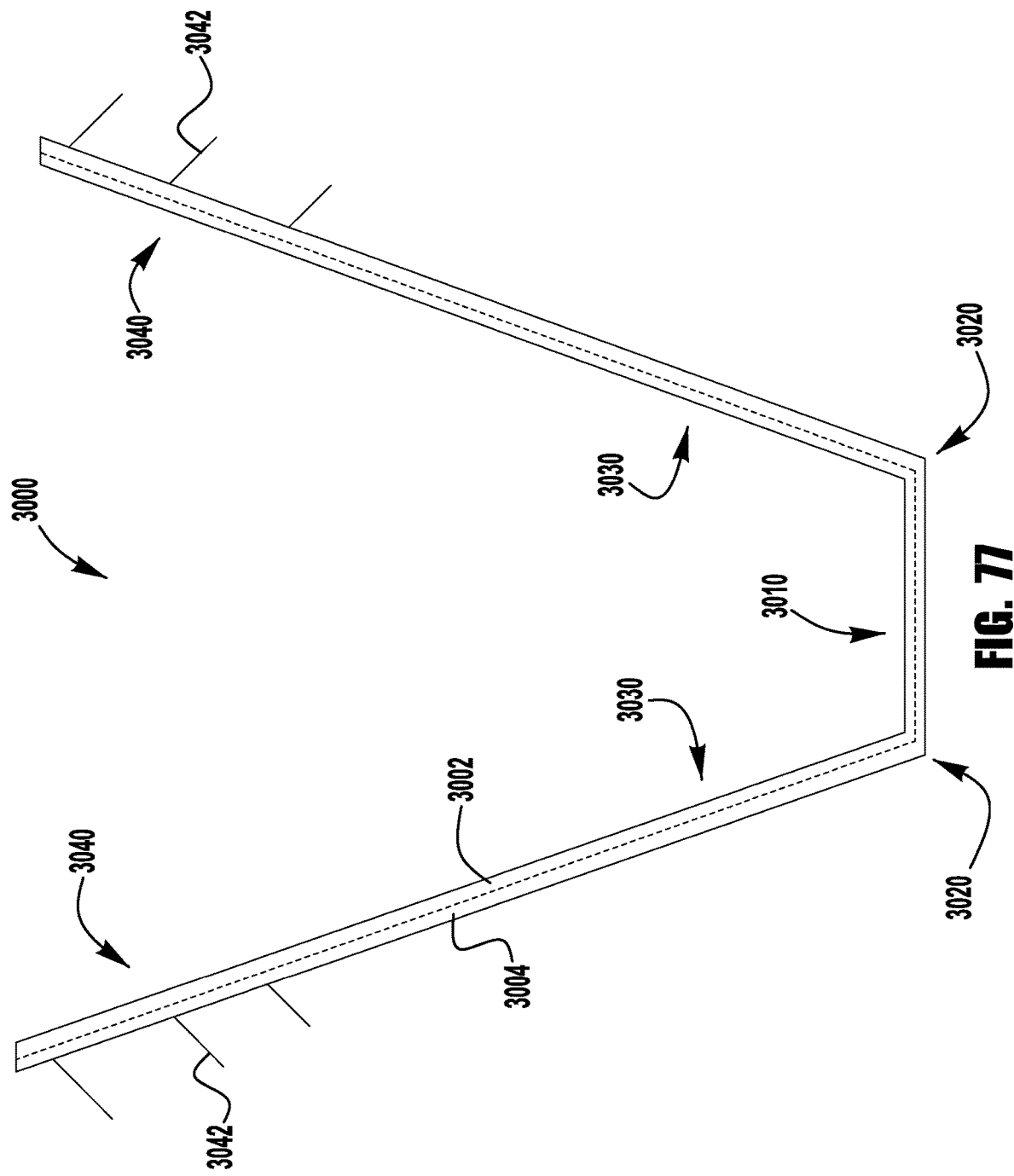
FIG. 77 shows a barbed clasp for an implantable prosthetic device according to a sixteenth embodiment.

Referring now to FIG. 77, a side view of an exemplary double-ended barb clasp 3000 is shown. The double-ended clasp 3000 has a fixed arm 3010 with hinge portions 3020 and moveable arms 3030 extending from both ends. Each moveable arm 3030 includes a barbed portion 3040 including at least one barb 3042. While the barbs 3042 are shown facing outwards, in other embodiments the barbs 3042 face inwards. The clasp 3000 is formed from first and second layers of material 3002, 3004, though, in certain embodiments, the clasp is formed from a single layer, and in certain other embodiments, is formed from more than two layers. The hinge portions 3020, movable arms 3030, and barbed portions 3040 may be formed in the shape of any of the clasps described above.

Figure 78:
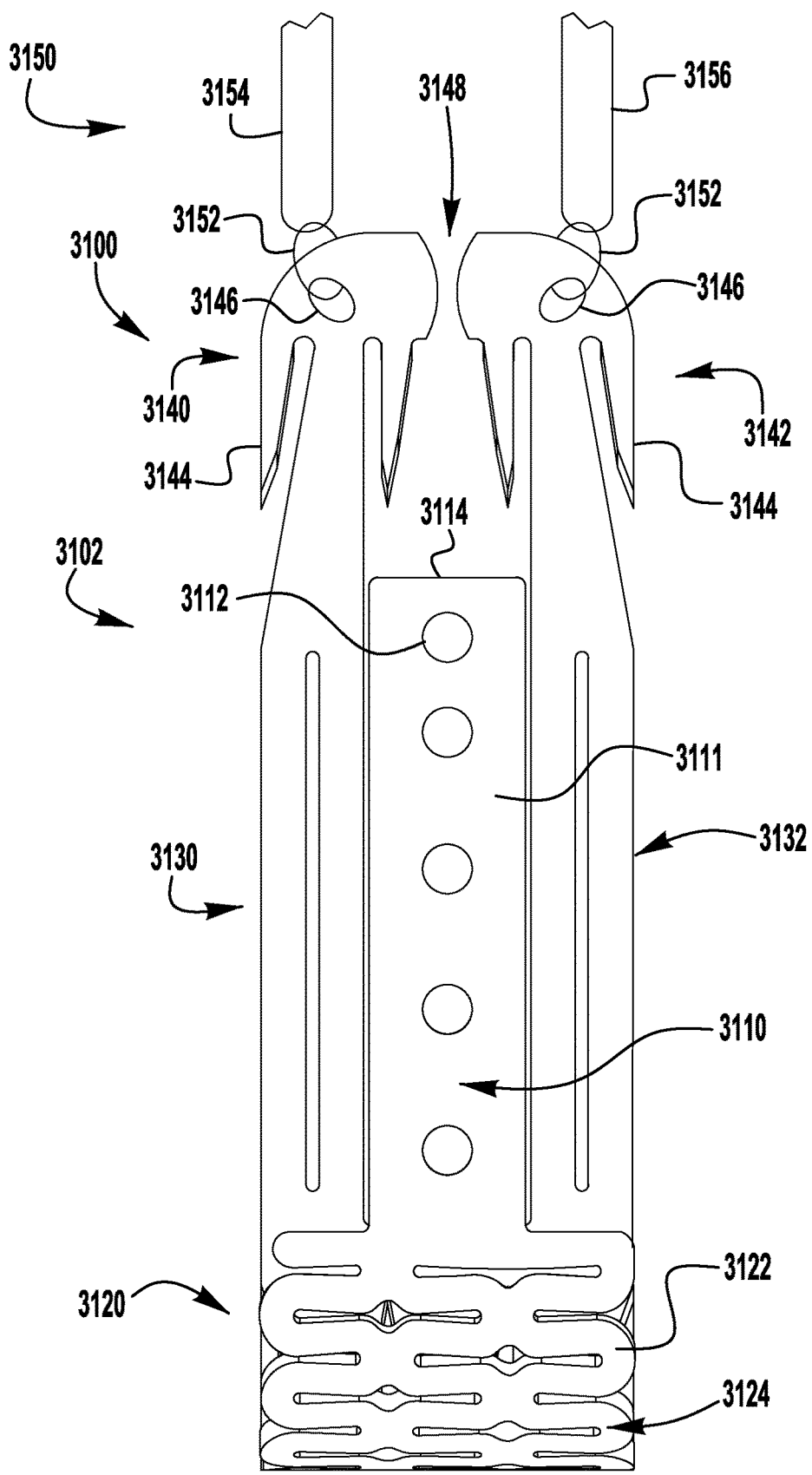
FIGS. 78-79 shows a barbed clasp for an implantable device according to a seventeenth embodiment.
Figure 79:
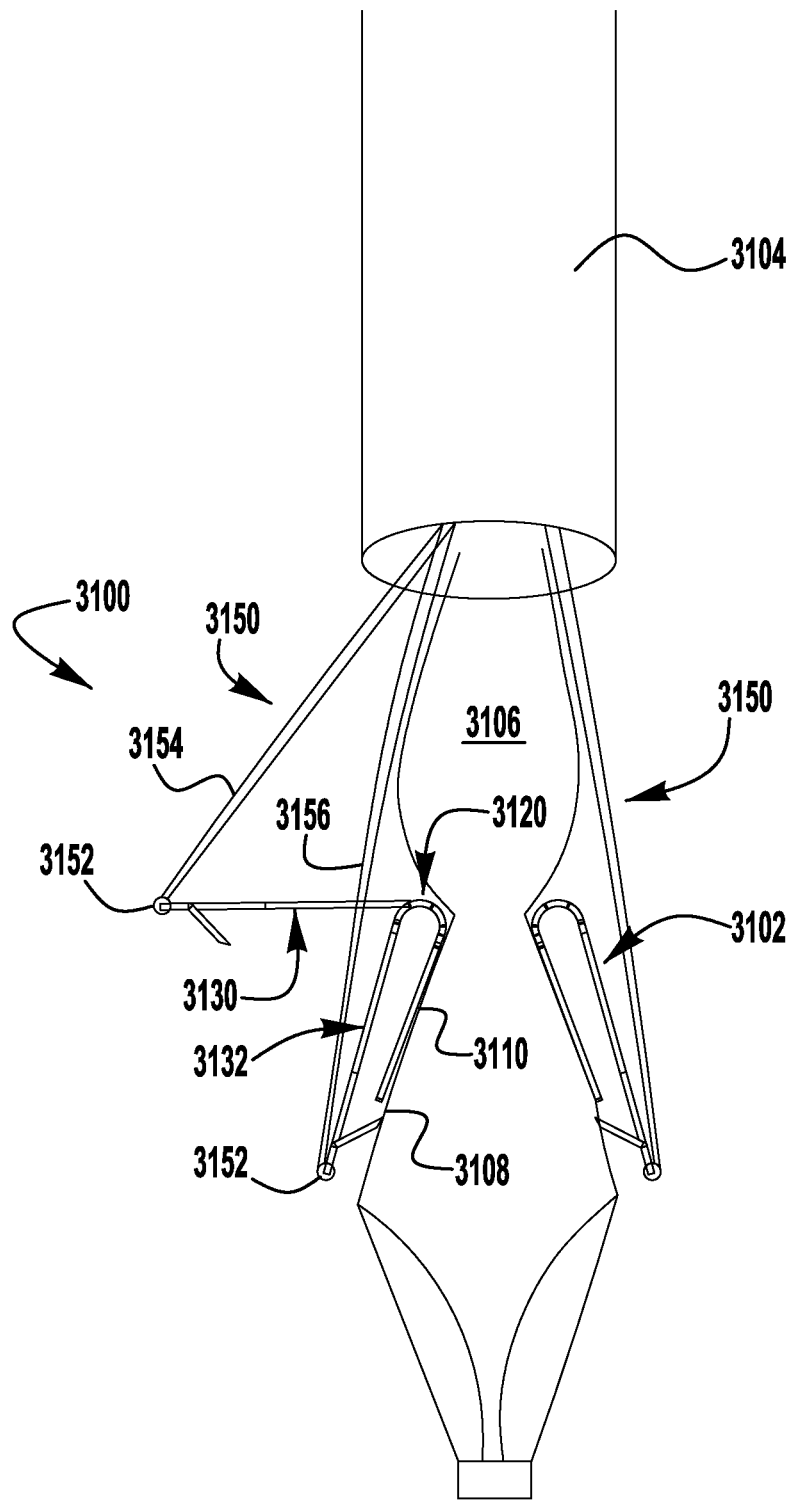

Referring now to FIGS. 78-79, an exemplary barbed clasp 3102 for use in implantable prosthetic devices, such as devices 100, 200, 300 described above, is shown. The barbed clasp 3102 includes elements of clasp 1200 described above. The barbed clasp 3102 includes a fixed arm 3110 that is attached to the implantable device and a hinge portion 3120 that allows the clasp 3102 to open and close. The hinge portion 3120 is formed from a repeating pattern of spring segments 3122 and cutouts 3124, like that of the clasp 1200. The barbed clasp 3102 also includes a pair of independent first and second movable arms 3130, 3132 extending from the hinge portion 3120 to a barbed portion 3140 having barbs 3144.

The fixed arm 3110 is formed from a tongue 3111 extending from the hinge portion 3120 to an end 3114. The tongue 3111 includes holes 3112 for securing the tongue 3111 to the implantable device. In certain embodiments, the tongue 3111 is formed from a wide plate of material to provide a larger lateral area as a pinching location. In certain embodiments, the end 3114 of the tongue 3111 includes a T-shape cross-member like that of clasp 3102.

The moveable arms 3130, 3132 of the clasp 3102 individually pinch the tissue of the native leaflet which allows for improved engagement of tissue that is not uniform in thickness. In some embodiments, the moveable arms 3130, 3132 are formed from a single moveable arm similar to the moveable arm 1230 of clasp 1200 that is separated into first and second moveable arms 3130, 3132 by a cut 3148 so that the first and second moveable arms 3130, 3132 are allowed to open and close independent from each other. In some embodiments, the hinge portion 3120 is also separated into first and second hinge portions (not shown).

Referring now to FIG. 79, an exemplary implantable device 3100 is shown assembled with two barb clasps 3102. The barb clasps 3102 are attached to inner paddles 3108 of the implantable device 3100 that extend from a coaption element 3106. An actuation arrangement 3150 includes intermediate suture loops 3152 attached to holes 3146 in the barbed portion 3140 of the first and second moveable arms 3130, 3132 and first and second actuation sutures 3154, 3156. The first and second actuation sutures 3154, 3156 extend from the delivery sheath 3104, through the intermediate suture loops 3152, and back into the delivery sheath 3104. Each of the moveable arms 3130, 3132 can be separately opened by applying tension to the first and second actuation sutures 3154, 3156, respectively. Opening the first and second moveable arms 3130, 3132 separately allows the grip of the clasp 3102 on native tissue to be adjusted based on the thickness of the tissue and the orientation of the clasp 3100.

Figure 80A:
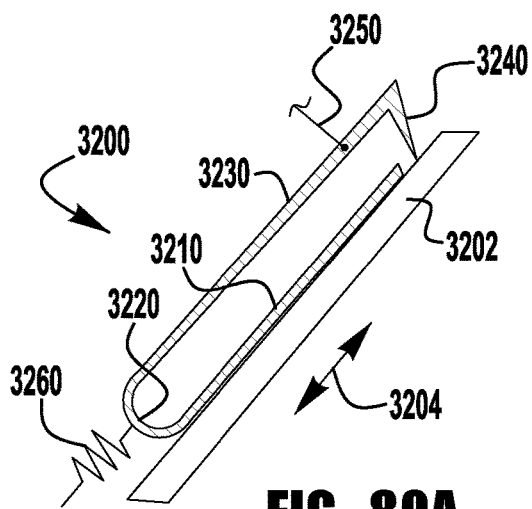
FIG. 80A-80E shows a barbed clasp for an implantable device according to an eighteenth embodiment.
Figure 80B:
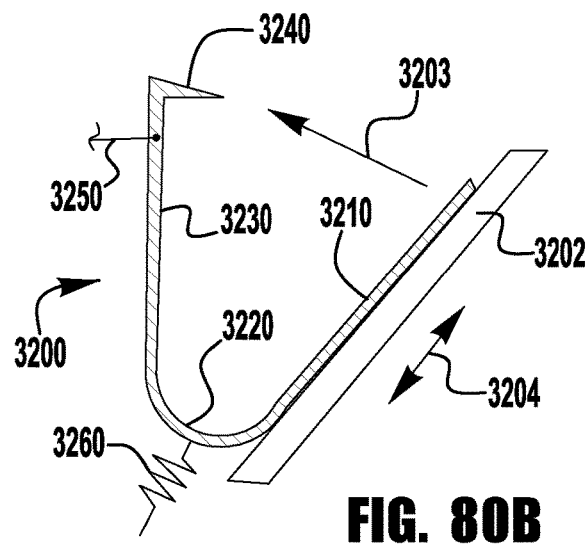

Referring now to FIGS. 80A-80E, an exemplary barbed clasp 3200 for use in implantable prosthetic devices, such as devices 100, 200, 300 described above, is shown. The clasp 3200 is configured to place a tensioning force on the native tissue when the implantable prosthetic device—e.g., any device described in the present application—is attached to the native tissue. Like the barbed clasps described above, the barbed clasp 3200 includes a fixed arm 3210, a hinge portion 3220, and a moveable arm 3230 having a barbed portion 3240. The fixed arm 3210 of the clasp 3200 is slideably connected to a paddle 3202 of an implantable device such that the clasp 3200 can be moved along the paddle 3202 in the direction 3204. For example, an actuation line 3250 can be used to move the clasp 3200 along the paddle 3202 in the direction 3204. The actuation line 3250 can also be used move the moveable arm 3230 between the closed position (as shown in FIG. 80A) and the open position (as shown in FIG. 80B). The actuation line 3250 can take any form described in the present application. In some embodiments, the clasp 3200 includes an optional biasing member 3260 (e.g., a spring) configured to maintain the clasp 3200 in a desired position along the paddle 3202 (e.g., the position shown in FIGS. 80A and 80E).

Figure 80C:
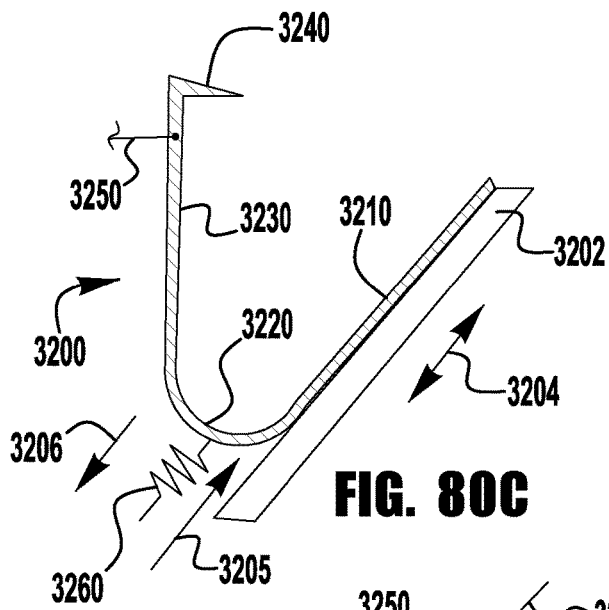
Figure 80D:
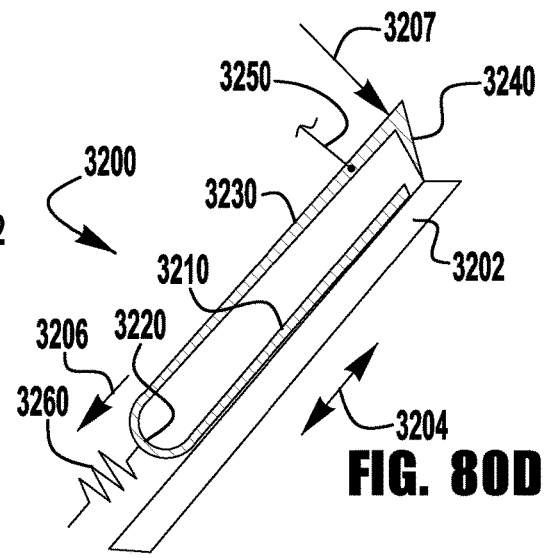
Figure 80E:
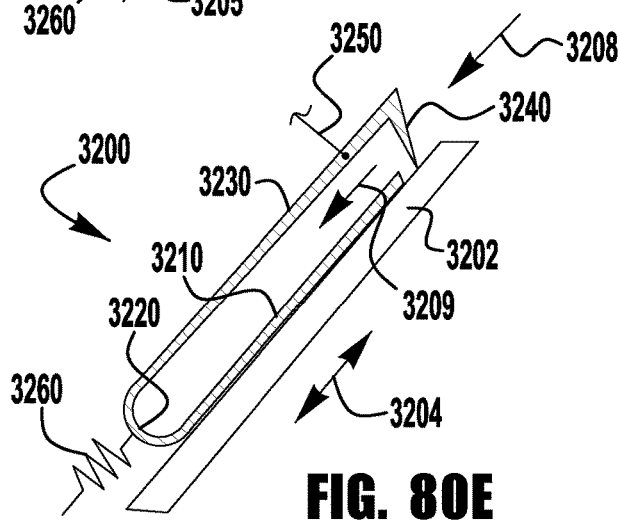

Referring to FIG. 80A, the clasp 3200 is shown in a first position on the paddle 3202 and in a closed position. Referring to FIG. 80B, the clasp 3200 is shown after the moveable arm 3230 has been moved in a direction 3203 to an open position by the actuation line 3250. Referring to FIG. 80C, the clasp 3200 is shown after having been moved along the paddle 3202 in a direction 3205 to a second position. In some embodiments, the clasp 3200 is moved along the paddle 3202 in the direction 3205 by the actuation line 3250 or a separate mechanism. In embodiments that include the biasing member 3260, enough force is applied to the clasp 3200 to move the clasp 3200 in the direction 3205, causing the biasing member 3260 to expand and create a tension force on the clasp 3200 in a direction 3206 opposite to the direction 3205. While the illustrated embodiment shows the clasp 3200 being moved to an open position (as shown in FIG. 80B) prior to the clasp 3200 being moved along the paddle 3202 in the direction 3205 to the second position (as shown in FIG. 80C), it should be understood that clasp 3200 can be moved in the direction 3205 to the second position prior to the moveable arm 3230 of the clasp 3200 being moved in the direction 3203 to an open position or the movements can be simultaneous. Referring to FIG. 80D, the moveable arm 3230 is moved to a closed position in the direction 3207 by the actuation line 3250 to secure the barbed portion 3240 of the clasp 3200 to valve tissue (not shown). In the position shown in FIG. 80D, the biasing member 3260 is being maintained in an extended position (e.g., as a result of the force applied to the clasp 3200 by the actuation line 3250, or another mechanism, to keep the clasp 3200 in the second position), which means the biasing member 3260 is placing a tensioning force on the clasp 3200 in the direction 3206. Referring to FIG. 80E, after the barbed portion 3240 of the clasp 3200 is secured to the native tissue, the force maintaining the clasp 3200 in the second position is released, which causes the tensioning force applied by the biasing member 3260 to move the clasp 3200 along the paddle 3202 in the direction 3208. The movement of the clasp 3200 in the direction 3208 causes the barbed portion 3240 to create a tensioning force on the native tissue in the direction 3209. This tensioning force on the native tissue allows the implantable device to maintain a secure connection to the native tissue.

Referring now to FIGS. 81A-81C, an exemplary barbed clasp 3300 for use in implantable prosthetic devices, such as devices 100, 200, 300 described above, is shown. The clasp 3300 is configured to place a tensioning force on the native tissue when the implantable prosthetic device—e.g., any device described in the present application—is attached to the native tissue. Like the barbed clasps described above, the barbed clasp 3300 includes a fixed arm 3310, a hinge portion 3320, and a moveable arm 3330 having a barbed portion 3340. The moveable arm 3330 includes a flexible portion 3332 arranged between the hinge portion 3320 and the barbed portion 3340. The flexible portion 3332 may comprise, for example, a cutout in the moveable arm 3330, a different material than the remainder of the moveable arm 3330, or can take any other suitable form that allows the flexible portion 3332 to be more flexible than the remainder of the moveable arm 3330. In some embodiments, the flexible portion 3332 is omitted and an actuation mechanism 3350 is still capable of flexing the barbed portion 3340 of the moveable arm 3330 as illustrated by FIGS. 81A-81C.

Figure 82:
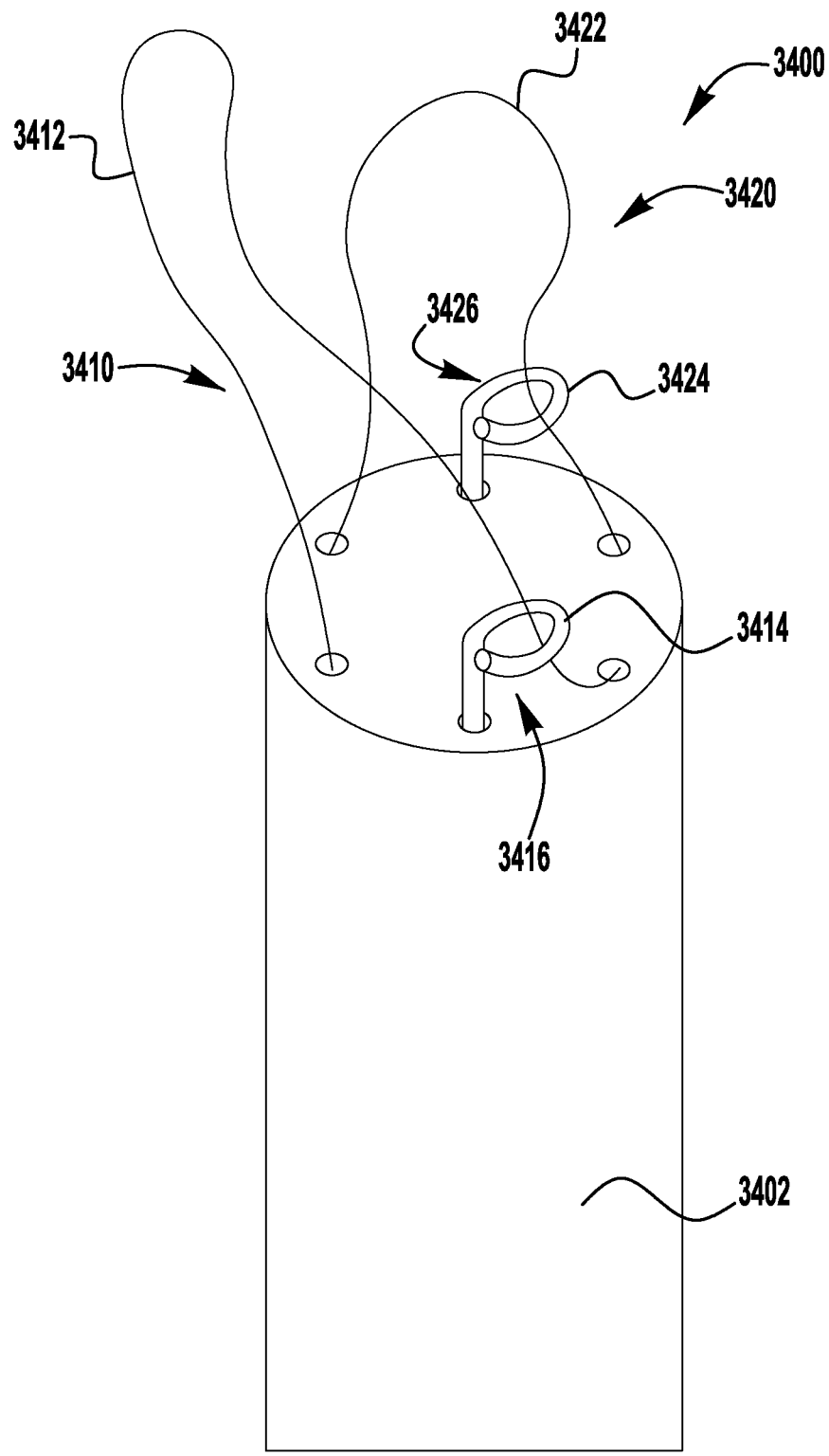
FIG. 82 shows an exemplary actuation mechanism for use with implantable devices described herein.

The actuation mechanism 3350 includes an actuation line 3352 (e.g., a suture) and a push-pull link 3354 configured to receive the line 3352. The push-pull link 3354 can be a catheter, a wire with a loop (as shown in FIG. 82), or any other link that is capable of receiving the line 3352 and pushing or pulling the moveable arm 3330 of the clasp 3300. The actuation line 3352 extends at a first end 3351 from a delivery sheath (not shown) and is removably attached to the moveable arm 3330 at a first connection point 3356 arranged proximate the barbed portion 3340. The actuation line 3352 also extends from the first connection point 3356 and is removably attached to the moveable arm 3330 at a second connection point 3358 arranged between the flexible portion 3332 and the hinge portion 3320. The actuation line 3352 then extends from the second connection point 3358 and through the push-pull link 3354 at a second end 3353.

Referring to FIG. 81A, the clasp 3300 is shown in an open position with native tissue 3302 disposed in an opening 3304 between the moveable arm 3330 and the fixed arm 3310. The clasp 3300 can be moved to the open position by pulling on the line 3352. Referring to FIG. 81B, the link 3354 and the line 3352 of the actuation mechanism 3350 is used to move the moveable arm 3330 in the closing direction 3306 to the closed position and flex the barbed portion 3340 in the opening direction 3308. In doing so, the first end 3351 of the line 3352 is pulled in the opening direction 3308 while the link 3354 is pushed in the closing direction 3306 such that the barbed portion 3340 of the moveable arm 3330 pivots or flexes at the flexible portion 3332 in the upward direction 3303 as it opens. Still referring to FIG. 81B, the link 3354 and the line 3352 are moved such that the barbed portion 3340 engages or pierces the native tissue 3302 as the moveable arm 3330 is moved into the closed position and the barbed portion 3340 is in the flexed position.

Referring now to FIG. 81C, the first end 3351 of the line 3352 is released, allowing the barbed portion 3340 of the moveable arm 3330 to pivot about the flexible portion 3332. As the barbed portion 3340 pivots, the native tissue 3302 is retracted in the downward or inward direction 3305, thereby creating a tensioning force on the native tissue in the inward direction 3305. After the moveable arm 3330 is secured to the native tissue 3302 (as shown in FIG. 81C) the link 3354 and the line 3352 are removed from the clasp 3300.

Referring now to FIG. 82, an actuation mechanism 3400 for use in implantable prosthetic devices, such as devices 100, 200, 300 described above, is shown. The mechanism 3400 includes first and second control members 3410, 3420 that extend from a delivery device 3402. The delivery device 3402 may be any suitable device, such as a sheath or catheter. The first and second control members 3410, 3420 include first and second sutures 3412, 3422 and first and second flexible wires 3414, 3424. The first and second flexible wires 3414, 3424 extend from the delivery device 3402 and each include a loop 3416, 3426 for receiving the first and second sutures 3412, 3422 and for engaging a clasp (e.g., clasp 1200 described above). Each of the first and second sutures 3412, 3422 extends from the delivery device 3402, through a one of the first and second loops 3416, 3426, respectively, and back into the delivery device 3402. In some embodiments, the first and second control members 3412, 3422 extend through separate delivery devices 3402. The sutures 3412, 3422 are removably attached to moveable arms of exemplary barbed clasps described above. The first and second loops 3416, 3426 of the respective wires 3414, 3424 are able to move along the corresponding sutures 3412, 3422 such that the loops 3416, 3426 can engage the corresponding barbed clasps to engage the moveable arms. That is, the sutures 3412, 3422 are used to pull the moveable arms in an opening direction and the wires 3414, 3424 are used to push the moveable arms in a closing direction. The wires 3414, 3424 can be made of, for example, steel alloy, nickel-titanium alloy, or any other metal or plastic material. In certain embodiments, the wires 3414, 3424 can have a diameter between about 0.10 mm and about 0.35 mm, between about 0.15 mm and about 0.30 mm, and between about 0.20 mm and about 0.25 mm.

While various inventive aspects, concepts and features of the disclosures may be described and illustrated herein as embodied in combination in the exemplary embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, alternatives as to form, fit, and function, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein.

Additionally, even though some features, concepts, or aspects of the disclosures may be described herein as being a preferred arrangement or method, such description is not intended to suggest that such feature is required or necessary unless expressly so stated. Still further, exemplary or representative values and ranges may be included to assist in understanding the present application, however, such values and ranges are not to be construed in a limiting sense and are intended to be critical values or ranges only if so expressly stated.\

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of exemplary methods or processes are not limited to inclusion of all steps as being required in all cases, nor is the order that the steps are presented to be construed as required or necessary unless expressly so stated. The words used in the claims have their full ordinary meanings and are not limited in any way by the description of the embodiments in the specification.

What is claimed is:

1. An implantable prosthetic device comprising:
   an anchor portion comprising a plurality of paddles, the paddles having an outer and inner portion and being extendable from a folded closed position to an open position; and
   a clasp attached to each of the plurality of paddles, the clasp comprising:
      a fixed arm fixedly attached to the inner portion of the paddle;
      a moveable arm having a barbed portion and an end that is rounded; and
      a hinge portion directly connecting the fixed arm to the moveable arm.

2. The implantable prosthetic device according to claim 1, wherein edges of the moveable arm are rounded.

3. The implantable prosthetic device according to claim 1, wherein the end of the moveable arm has a semi-elliptical shape.

4. The implantable prosthetic device according to claim 1, wherein the hinge portion comprises a plurality of spring segments, wherein each spring segment is connected to a plurality of spring segments.

5. The implantable prosthetic device according to claim 4, wherein the spring segments are torsional spring segments.

6. The implantable prosthetic device according to claim 1, wherein:
   the spring segments comprise a first end and a second end; and
   the first end of one spring segment is connected to at least one of the first and second end of another spring segment.

7. The implantable prosthetic device according to claim 1, wherein:
   the spring segments comprise a first end, a second end, a first side, and a second side;
   a first side joining location is adjacent the first end;
   a first end joining location is adjacent the first side;
   a second side joining location is adjacent the second end; and
   a second end joining location is adjacent the second side.

8. The implantable prosthetic device according to claim 6, wherein:
   the spring segments are arranged into a plurality of rows and columns;
   the first or second ends of spring segments proximate a side edge of the clasp are joined to one other spring segment; and the first or second ends of spring segments proximate an adjacent column are joined to at least one other spring segment.

9. The implantable prosthetic device according to claim 1, wherein:
the spring segments are arranged in a pattern having three columns and seven rows of spring segments.

10. The implantable prosthetic device according to claim 1, wherein the clasp is formed from shape memory material and the fixed and moveable arms are shape set in a preloading position so that a pinch force exists between the fixed and moveable arms when the fixed arm is approximately parallel with the moveable arm.

11. The implantable prosthetic device according to claim 10, wherein the fixed arm is bent in the closing direction beyond the closed position to the preloading position.

12. The implantable prosthetic device according to claim 11, wherein the fixed arm is bent in the closing direction to about 45 degrees beyond the closed position to the preloading position.

13. The implantable prosthetic device according to claim 11, wherein the fixed arm is bent in the closing direction to about 90 degrees beyond the closed position to the preloading position.

14. The implantable prosthetic device according to claim 11, wherein after shape setting, the fixed arm is prohibited from returning to the preloading position by a cross-member.

15. The implantable prosthetic device according to claim 14, wherein the cross-member is an integral cross-member.

16. The implantable prosthetic device according to claim 1, wherein a plastic limit of the material of the clasp is not exceeded when the moveable arm is opened to a fully open position about 140 degrees from the fixed arm.

17. The implantable prosthetic device according to claim 1, wherein barbs of the barbed portion are tapered in the direction of the length of the clasp.

18. The implantable prosthetic device according to claim 1, wherein the movable arm comprises a plurality of independent arms transitionable between a wide, spread-out configuration and a narrow configuration in which the arms are closer together, and wherein barbs of the barbed portion end in a point.

19. A clasp comprising:
a fixed arm;
a moveable arm;
a hinge portion directly connecting the fixed arm to the moveable arm to enable the clasp to be moved between open and closed positions; and
a barbed portion of the moveable arm comprising a plurality of barbs that extend toward the fixed arm when the clasp is in the closed position.

20. The clasp according to claim 19, wherein edges of the moveable arm are rounded.

21. The clasp according to claim 19, wherein the end of the moveable arm has a semi-elliptical shape.

22. The clasp according to claim 19, wherein the hinge portion comprises a plurality of spring segments, wherein each spring segment is connected to a plurality of spring segments.

23. The clasp according to claim 22, wherein the spring segments are torsional spring segments.

24. The clasp according to claim 22, wherein:
the spring segments comprise a first end and a second end; and
the first end of one spring segment is connected to at least one of the first and second end of another spring segment.

25. The clasp according to claim 22, wherein:
the spring segments comprise a first end, a second end, a first side, and a second side;
a first side joining location is adjacent the first end;
a first end joining location is adjacent the first side;
a second side joining location is adjacent the second end; and
a second end joining location is adjacent the second side.

26. The clasp according to claim 24, wherein:
the spring segments are arranged into a plurality of rows and columns;
the first or second ends of spring segments proximate a side edge of the clasp are joined to one other spring segment; and
the first or second ends of spring segments proximate an adjacent column are joined to at least one other spring segment.

27. The clasp according to claim 22, wherein:
the spring segments are arranged in a pattern having three columns and seven rows of spring segments.

28. The clasp according to claim 19, wherein the clasp is formed from shape memory material and the fixed and moveable arms are shape set in a preloading position so that a pinch force exists between the fixed and moveable arms when the fixed arm is approximately parallel with the moveable arm.

29. The clasp according to claim 28, wherein the fixed arm is bent in the closing direction beyond the closed position to the preloading position.

30. The clasp according to claim 29, wherein the fixed arm is bent in the closing direction to about 45 degrees beyond the closed position to the preloading position.

31. The clasp according to claim 29, wherein the fixed arm is bent in the closing direction to about 90 degrees beyond the closed position to the preloading position.

32. The clasp according to claim 29, wherein after shape setting, the fixed arm is prohibited from returning to the preloading position by a cross-member.

33. The clasp according to claim 32, wherein the cross-member is an integral cross-member.

34. The clasp according to claim 19, wherein a plastic limit of the material of the clasp is not exceeded when the moveable arm is opened to a fully open position about 140 degrees from the fixed arm.

35. The clasp according to claim 19, wherein barbs of the barbed portion are tapered in the direction of the length of the clasp.

36. The clasp according to claim 19, wherein the barbs of the barbed portion end in a point.

37. The clasp according to claim 19, wherein the moveable arm has an end that is rounded.

38. The clasp according to claim 19, wherein the clasp is formed from a single piece.

39. The clasp according to claim 19, wherein the moveable arm comprises a plurality of independent arms transitionable between a wide, spread-out configuration and a narrow configuration in which the arms are closer together.

40. An implantable prosthetic device comprising:
an anchor portion comprising a plurality of paddles; and
a clasp attached to each of the plurality of paddles, the clasp comprising:

a fixed arm fixedly attached to one of the plurality of paddles;
a moveable arm having and an end that is rounded; and
a hinge portion directly connecting the fixed arm to the moveable arm.

\* \* \* \* \*